United States Patent
Chai et al.

(10) Patent No.: US 11,426,375 B2
(45) Date of Patent: *Aug. 30, 2022

(54) SUBSTITUTED BISPHENYL BUTANOIC ESTER DERIVATIVES AS NEP INHIBITORS

(71) Applicant: NOVARTIS AG, Basel (CH)

(72) Inventors: Yongshuai Chai, Shanghai (CN); Sven Erik Godtfredsen, Chatham, NJ (US); Mark Kagan, East Hanover, NJ (US); Yugang Liu, Bridgewater, NJ (US); Mahavir Prashad, Montville, NJ (US); Zhaoyin Wang, Shanghai (CN); Saijie Zhu, Shanghai (CN)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/854,355

(22) Filed: Apr. 21, 2020

(65) Prior Publication Data

US 2020/0246295 A1 Aug. 6, 2020

Related U.S. Application Data

(63) Continuation of application No. 16/388,221, filed on Apr. 18, 2019, now Pat. No. 10,668,035, which is a continuation of application No. PCT/CN2019/074778, filed on Feb. 11, 2019.

(51) Int. Cl.
| | |
|---|---|
| A61K 31/235 | (2006.01) |
| A61K 31/24 | (2006.01) |
| A61K 31/41 | (2006.01) |
| A61K 31/197 | (2006.01) |
| A61P 9/00 | (2006.01) |
| A61K 31/405 | (2006.01) |
| C07C 229/36 | (2006.01) |
| C07C 233/47 | (2006.01) |
| C07C 279/14 | (2006.01) |
| C07D 209/08 | (2006.01) |

(52) U.S. Cl.
CPC .......... *A61K 31/197* (2013.01); *A61K 31/405* (2013.01); *A61K 31/41* (2013.01); *A61P 9/00* (2018.01); *C07C 229/36* (2013.01); *C07C 233/47* (2013.01); *C07C 279/14* (2013.01); *C07D 209/08* (2013.01); *A61K 31/235* (2013.01)

(58) Field of Classification Search
CPC .............................. A61K 31/216; A61K 31/41
USPC ......................................... 514/533, 534, 381
See application file for complete search history.

(56) References Cited

U.S. PATENT DOCUMENTS

| | | | |
|---|---|---|---|
| 5,217,996 A | 6/1993 | Ksander | |
| 5,250,522 A | 10/1993 | De Lombaert | |
| 5,273,990 A | 12/1993 | De Lombaert | |
| 5,294,632 A | 3/1994 | Erion et al. | |
| 5,432,186 A | 7/1995 | Fink | |
| 5,506,244 A | 4/1996 | Fink | |
| 5,508,266 A | 4/1996 | Fink | |
| 5,550,119 A | 8/1996 | De Lombaert et al. | |
| 5,668,158 A | 9/1997 | Fink | |
| 10,668,035 B2* | 6/2020 | Chai | A61K 31/197 |
| 2002/0183260 A1 | 12/2002 | Hoxie | |
| 2004/0266698 A1 | 12/2004 | Fink | |
| 2010/0305131 A1 | 12/2010 | Coppola et al. | |
| 2010/0305145 A1 | 12/2010 | Coppola et al. | |
| 2011/0124695 A1 | 5/2011 | Iwaki et al. | |
| 2012/0122764 A1 | 5/2012 | Karki et al. | |

(Continued)

FOREIGN PATENT DOCUMENTS

| | | |
|---|---|---|
| CN | 105061263 A | 8/2015 |
| CN | 105601524 A | 5/2016 |

(Continued)

OTHER PUBLICATIONS

Stella, V. J., et al., "Prodrugs: Challenges and Rewards. Biotechnology: Pharmaceutical Aspects", 2007.

(Continued)

*Primary Examiner* — Shengjun Wang
(74) *Attorney, Agent, or Firm* — Timothy P. O'Dea

(57) ABSTRACT

The present disclosure provides a compound of Formula (I);

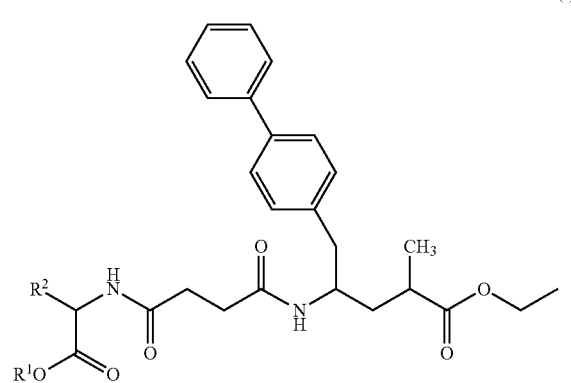

(I)

or a pharmaceutically acceptable salt thereof, wherein $R^1$ and $R^2$ are defined herein. The disclosure also relates to a method for manufacturing the compounds of the disclosure, and its therapeutic uses. The present disclosure further provides pharmaceutical composition of the compounds of the disclosure and a combination of pharmacologically active agents and a compound of the disclosure.

26 Claims, 18 Drawing Sheets

(56) References Cited

U.S. PATENT DOCUMENTS

| | | |
|---|---|---|
| 2012/0122844 A1 | 5/2012 | Foo |
| 2012/0122977 A1 | 5/2012 | Coppola et al. |
| 2012/0213807 A1 | 8/2012 | Fleury et al. |
| 2013/0109639 A1 | 5/2013 | Hughes et al. |
| 2014/0228323 A1 | 8/2014 | Barnes et al. |
| 2014/0228415 A1 | 8/2014 | Barnes et al. |
| 2014/0256702 A1 | 9/2014 | Fenster et al. |
| 2015/0209352 A1 | 7/2015 | Fleury et al. |
| 2015/0210690 A1 | 7/2015 | Fleury et al. |
| 2016/0228395 A1 | 8/2016 | Hughes et al. |

FOREIGN PATENT DOCUMENTS

| | | |
|---|---|---|
| CN | 106467474 A | 8/2016 |
| CN | 107216277 A | 6/2017 |
| EP | 555175 A1 | 8/1993 |
| EP | 655461 A1 | 5/1995 |
| WO | 0359345 A1 | 7/2003 |
| WO | 2005/046575 A2 | 5/2005 |
| WO | 2007/056546 A1 | 5/2007 |
| WO | 2007/089745 A2 | 8/2007 |
| WO | 2008/083967 A2 | 7/2008 |
| WO | 2008/133896 A2 | 11/2008 |
| WO | 10081410 A1 | 7/2010 |
| WO | 2010/136474 A1 | 12/2010 |
| WO | 2010/136493 A1 | 12/2010 |
| WO | 2011/035569 A1 | 3/2011 |
| WO | 2011/061271 A1 | 5/2011 |
| WO | 2012/065956 A1 | 5/2012 |
| WO | 2012/065958 A1 | 5/2012 |
| WO | 2012/082853 A1 | 6/2012 |
| WO | 2012/082857 A1 | 6/2012 |
| WO | 2012/112742 A1 | 8/2012 |
| WO | 2013/067163 A1 | 5/2013 |
| WO | 2013/181332 A1 | 12/2013 |
| WO | 2013/184934 A1 | 12/2013 |
| WO | 2014/025891 A1 | 2/2014 |
| WO | 2014029848 A1 | 2/2014 |
| WO | 2014/126979 A1 | 8/2014 |
| WO | 2014126972 A1 | 8/2014 |
| WO | 2014/198195 A1 | 12/2014 |
| WO | 2015/116760 A1 | 8/2015 |
| WO | 2015/116786 A1 | 8/2015 |
| WO | 2015/154673 A1 | 10/2015 |
| WO | 2016/037552 A1 | 3/2016 |
| WO | 2016/133803 A1 | 8/2016 |
| WO | 2016/180275 A1 | 11/2016 |
| WO | 2017/033128 A1 | 3/2017 |
| WO | 2017033128 A1 | 3/2017 |
| WO | 2017/098430 A1 | 6/2017 |

OTHER PUBLICATIONS

Balvinder, S. V., et al.,"Amino acids as promoieties in prodrug design and development", Advanced Drug Delivery Reviews. 2013; 65:1370-1385.

Vale, N., et al., Amino Acids in the Development of Prodrugs. Molecules. Sep. 11, 2018, 23(2318):1-61.

Huttunen, K. M., "Prodrugs—from Serendipity to Rational Design", Pharmacological Reviews, 2011; 63(3):750-771.

Stella, V. J., et al., "Prodrug strategies to overcome poor water solubility", Advanced Drug Delivery Reviews. 2007; 59 :677-694.

Ksander, G. M., et al., "Dicarboxylic Acid Dipeptide Neutral Endopeptidase Inhibitors", J. Med. Chem. 1995; 38:1689-1700.

Velmourougane, G., et. al., "Synthesis of New (−)-Bestatin-Based Inhibitor Libraries Reveals a Novel Binding Mode in the S1 Pocket of the Essential Malaria M1 Metalloaminopeptidase", J. Med. Chem., (2011), 54(6), 1655-1666.

Wu, Chun, et al., "Synthesis, Pharmacokinetics, and Pharmacodynamics Studies of Valsartan Peptide Derivatives", Arch. Pharm. Chem. Life Sci. 345:393-400, 2012.

International Search Report for PCT/CN2019/074778 dated May 16, 2019.

Gibler, New Drug Evaluation: sacubitril/valsartan tablet, oral, Oregon Health Authority, Sep. 2015, https://www.orpdl.org/durm/meetings/meetingdocs_2015_09_24/archives/2015_09_24_Sacubitril_ValsartanNDEARCHIVED.pdr(Year:2015).

Shi et al., Sacubitril is selectively activated by carboxylesterase 1 (CES1) in the liver and the activation is affected by ES1 genetic variation, Drug Metabolism and Disposition, 2016, 554-559, 44.

\* cited by examiner

SUBSTITUTED BISPHENYL BUTANOIC ESTER DERIVATIVES AS NEP INHIBITORS

RELATED APPLICATIONS

This application is a continuation application of U.S. application Ser. No. 16/388,221, filed on Apr. 18, 2019, now allowed, which is a continuation of International Application No. PCT/CN2019/074778, with an international filing date of Feb. 11, 2019, which claims priority to, and the benefit of, International Application No. PCT/CN2018/075791, filed Feb. 8, 2018, and International Application No. PCT/CN2018/075515, filed on Feb. 7, 2018, the entire contents of each of which are incorporated herein by reference in their entireties.

FIELD OF THE DISCLOSURE

The disclosure provides neutral endopeptidase (EC 3.4.24.11) (NEP) inhibitor compounds, the use thereof for inhibiting peripheral NEP and methods of treating disease using same.

BACKGROUND

Endogenous atrial natriuretic peptides (ANP), also called atrial natriuretic factors (ANF) have diuretic, natriuretic and vasorelaxant functions in mammals. The natural ANF peptides are metabolically inactivated, in particular by a degrading enzyme which has been recognized to correspond to the enzyme neutral endopeptidase EC 3.4.24.11, also responsible for e.g. the metabolic inactivation of enkephalins.

Neutral endopeptidase (also known as NEP, endopeptidase 24.11, EC 3.4.24.11; neprilysin, enkephalinase; atriopeptidase; fibroblast metalloelastase, kidney-brush-border neutral peptidase, membrane metallopeptidase A, MME g.p. (*Homo sapiens*), common acute lymphocytic leukemia antigen (CALLA) or CD antigen (CD10)) is a zinc-containing metalloprotease found in many organs and tissues including brain, kidneys, lungs, gastrointestinal tract, heart and peripheral vasculature. NEP cleaves a variety of peptide substrates on the amino side of hydrophobic residues [see *Pharmacol Rev*, Vol. 45, p. 87 (1993)]. Substrates for this enzyme include, but are not limited to, atrial natriuretic peptide, brain natriuretic peptide (BNP), met- and leu-enkephalin, bradykinin, neurokinin A, endothelin-1, angiotensins, adrenomedullin, glucagon-like peptides, glucagon, insulin B chain, amyloid betas and substance P. Some of these peptides have potent vasodilatory and neurohormone functions, diuretic and natriuretic activity or mediate behavior effects. ANP is a potent vasorelaxant and natriuretic agent [see *J Hypertens*, Vol. 19, p. 1923 (2001)]. Infusion of ANP in normal subjects resulted in a reproducible, marked enhancement of natriuresis and diuresis, including increases in fractional excretion of sodium, urinary flow rate and glomerular filtration rate [see *J Clin Pharmacol*, Vol. 27, p. 927 (1987)]. However, ANP has a short half-life in circulation, and NEP in kidney cortex membranes has been shown to be the major enzyme responsible for degrading this peptide [see *Peptides*, Vol. 9, p. 173 (1988)]. Thus, neutral endopeptidase inhibitors should increase plasma levels of ANP and, hence, are expected to induce natriuretic and diuretic effects.

Furthermore, NEP enzyme plays an important role in blood pressure homeostasis and cardiovascular health.

Recently, the first NEP inhibitor, sacubitril, has been approved in combination with the angiotensin receptor antagonist valsartan for the treatment of heart failure.

In view of the vast opportunities for use of NEP inhibitors as therapeutics a need is emerging for NEP inhibitors with physio-chemical properties amenable for manufacturing of the active compounds and for pharmaceutical compositions comprising such compounds.

SUMMARY OF THE DISCLOSURE

The aim of the present disclosure is to provide novel NEP inhibitor compounds with improved physio-chemical properties and which deliver profiles of NEP inhibition optimal for specific disease and disease stages. In particular, prolonged exposure and reduced potential for Cmax may be desirable in certain disease conditions and for certain patient populations. The NEP inhibitors of the instant disclosure deliver unique profiles of NEP inhibition. In addition, the compounds of the disclosure exhibit favorable physio-chemical properties making them particularly amenable for industrial manufacturing needed to deliver the medicines at affordable prices to patients.

The compounds and crystalline forms, or pharmaceutically acceptable salts thereof, of the present disclosure possess improved stability, hygroscopicity, high aqueous solubility and/or pharmaceutical processability over known NEP inhibitor compounds (i.e., sacubitril (AHU377)). For example, the compounds and crystalline forms, or pharmaceutically acceptable salts thereof, possess powder-like appearance and good flowability, which is favorable for pharmaceutical processing.

The disclosure pertains to the compounds, pharmaceutical compositions and methods of use thereof as described herein. Examples of compounds of the disclosure include the compounds according to Formulae (I) and (II), or a pharmaceutically acceptable salt thereof and the compounds of the examples.

In a first aspect, the present disclosure relates to a compound of the Formula (I):

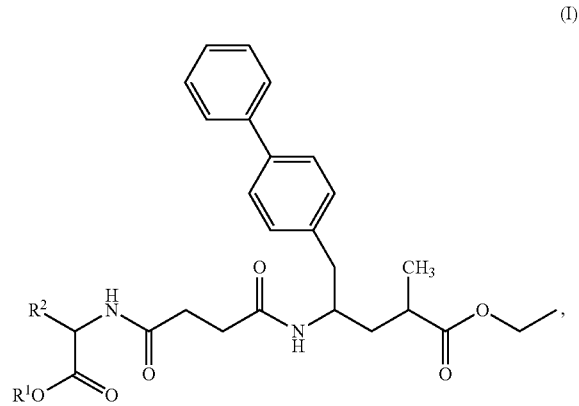

wherein:
$R^1$ is H or $(C_1\text{-}C_4)$alkyl;
$R^2$ is H, $(C_1\text{-}C_4)$alkyl, $(C_6\text{-}C_{10})$ aryl, or 5- or 6-membered heteroaryl comprising 1-3 heteroatoms selected from N, S, and O, wherein the alkyl is optionally substituted with one or more $R^3$, and wherein the aryl and heteroaryl are optionally substituted with one or more $R^4$;
each $R^3$ is independently at each occurrence —$NH_2$, $(C_1\text{-}C_4)$alkylamino, $(C_1\text{-}C_4)$dialkylamino, —OH, —SH, —S$(C_1\text{-}C_4)$alkyl, —$CO_2H$, —$CONH_2$, —NHC(NH)$NH_2$, $(C_6\text{-}C_{10})$ aryl, or 5- to 10-membered monocyclic or bicyclic heteroaryl comprising 1-3 heteroatoms selected from N, O, and S, wherein the aryl and heteroaryl are optionally substituted with one or more $R^5$;

each $R^4$ is independently at each occurrence $(C_1-C_4)$alkyl, $(C_1-C_4)$haloalkyl, $(C_1-C_4)$alkoxy, $(C_1-C_4)$haloalkoxy, halogen, —$NH_2$, —OH or CN; and each $R^5$ is independently at each occurrence $(C_1-C_4)$alkyl, $(C_1-C_4)$haloalkyl, $(C_1-C_4)$alkoxy, $(C_1-C_4)$haloalkoxy, halogen, —$NH_2$, —OH or CN;

or pharmaceutically acceptable salts, hydrates, solvates, prodrugs, stereoisomers, and tautomers thereof.

The compounds of the disclosure, by inhibiting the neutral endopeptidase, can potentiate the biological effects of bioactive peptides. Thus, in particular the compounds have utility in the prevention or treatment of a number of disorders, including hypertension, pulmonary hypertension, pulmonary arterial hypertension, isolated systolic hypertension, resistant hypertension, peripheral vascular disease, heart failure, heart failure with preserved ejection fraction (HF-PEF), heart failure with reduced ejection fraction (HF-REF), coronary artery disease (CAD), ischemic heart disease (IHD), mitral stenosis and regurgitation, left ventricular hypertrophy, angina, renal insufficiency (diabetic or non-diabetic), renal failure (including edema and salt retention), diabetic nephropathy, non-diabetic nephropathy, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, myocardial infarction (MI), heart failure after acute myocardial infarct, renal fibrosis, polycystic kidney disease (PKD), renal failure (including edema and salt retention), cyclical oedema, Menière's disease, hyperaldosteronism (primary and secondary), hypercalciuria and ascites. In addition, because of their ability to potentiate the effects of ANP, the compounds have utility in the treatment of glaucoma. As a further result of their ability to inhibit the neutral endopeptidase E.C.3.4.24.11 the compounds of the disclosure may have activity in other therapeutic areas including for example the treatment of menstrual disorders, preterm labor, pre-eclampsia, endometriosis, and reproductive disorders (especially male and female infertility, polycystic ovarian syndrome, implantation failure). Also the compounds of the disclosure should treat asthma, obstructive sleep apnea, inflammation, leukemia, pain, epilepsy, affective disorders such as depression, obesity and gastrointestinal disorders (especially diarrhea and irritable bowel syndrome), wound healing (especially diabetic and venous ulcers and pressure sores), septic shock, gastric acid secretion dysfunction, hyperreninemia, cystic fibrosis, restenosis, type-2 diabetes, metabolic syndrome, diabetic complications, atherosclerosis, and male and female sexual dysfunction.

In another embodiment, the compounds of the disclosure are useful in the treatment of a disorder or the disease selected from hypertension, pulmonary hypertension, isolated systolic hypertension, resistant hypertension, peripheral vascular disease, heart failure, heart failure with preserved ejection fraction (HF-PEF), heart failure with reduced ejection fraction (HF-REF), and pulmonary arterial hypertension. In a preferred embodiment the compounds of the disclosure are useful in the treatment of cardiovascular disorders.

In another aspect, the present disclosure relates to a method for treating disorders or diseases responsive to the inhibition of neutral endopeptidase, in a subject in need of such treatment, comprising: administering to the subject an effective amount of a compound according to Formula (I) or (II), or a pharmaceutically acceptable salt, hydrate, solvate, prodrug, stereoisomer, or tautomer thereof, such that the disorder or disease responsive to the inhibition of neutral endopeptidase in the subject is treated.

Another aspect of the present disclosure relates to pharmaceutical compositions, comprising a compound according to any one of Formula (I) or (II) or a pharmaceutically acceptable salt, hydrate, solvate, prodrug, stereoisomer, or tautomer thereof, and one or more pharmaceutically acceptable carriers.

In another aspect, the present disclosure relates to combinations including, a compound according to Formula (I) or (II), or a pharmaceutically acceptable salt, hydrate, solvate, prodrug, stereoisomer, or tautomer thereof, and pharmaceutical combinations of one or more therapeutically active agents.

Another aspect of the present disclosure relates to a method for inhibiting neutral endopeptidase in a subject in need thereof. The method comprising: administering to the subject a therapeutically effective amount of a compound according to Formula (I) or (II), or a pharmaceutically acceptable salt, hydrate, solvate, prodrug, stereoisomer, or tautomer thereof, such that neutral endopeptidase is inhibited.

In another aspect, the present disclosure relates to a method of treating a disorder or a disease associated with neutral endopeptidase activity in a subject in need thereof. The method comprising: administering to the subject a therapeutically effective amount of a compound according to Formula (I) or (II), or a pharmaceutically acceptable salt, hydrate, solvate, prodrug, stereoisomer, or tautomer thereof.

Another aspect of the present disclosure relates to a compound according to Formula (I) or (II), or a pharmaceutically acceptable salt, hydrate, solvate, prodrug, stereoisomer, or tautomer thereof, for use as a medicament.

In another aspect, the present disclosure relates to the use of a compound according to Formula (I) or (II), or a pharmaceutically acceptable salt, hydrate, solvate, prodrug, stereoisomer, or tautomer thereof, for the treatment of a disorder or disease associated with neutral endopeptidase activity in a subject in need of such treatment.

In another aspect, the present disclosure relates to a combination comprising: a compound according to Formula (I) or (II), or a pharmaceutically acceptable salt, hydrate, solvate, prodrug, stereoisomer, or tautomer thereof, and one or more therapeutically active agents selected from HMG-Co-A reductase inhibitor, an angiotensin receptor blocker, a calcium channel blocker, an endothelin antagonist, a renin inhibitor, a diuretic, an ApoA-I mimic, an anti-diabetic agent, an obesity-reducing agent, an aldosterone receptor blocker, an endothelin receptor blocker, an aldosterone synthase inhibitor, a CETP inhibitor, and a phosphodiesterase type 5 (PDE5) inhibitor.

Another aspect of the present disclosure relates to a combination comprising: a compound according to Formula (I) or (II), or a pharmaceutically acceptable salt, hydrate, solvate, prodrug, stereoisomer, or tautomer thereof, and an Angiotensin Receptor Blocker selected from valsartan, candesartan, losartan, irbesartan, telmisartan, olmesartan, eprosartan, fimasartan, and azilsartan, or a pharmaceutically acceptable salt thereof.

In another aspect, the present disclosure relates to a combination comprising: a compound according to Formula (I) or (II), or a pharmaceutically acceptable salt, hydrate, solvate, prodrug, stereoisomer, or tautomer thereof, and an Angiotensin Receptor Blocker, or a pharmaceutically acceptable salt thereof. In one embodiment, the Angiotensin Receptor Blocker is selected from valsartan, candesartan, losartan, irbesartan, telmisartan, olmesartan, eprosartan, fimasartan, and azilsartan, or a pharmaceutically acceptable salt thereof. In another embodiment, the Angiotensin Receptor Blocker is valsartan, or a pharmaceutically acceptable salt thereof.

Another aspect of the present disclosure relates to a method of inhibiting neutral endopeptidase activity in a subject in need thereof, comprising: administering to the subject a therapeutically effective amount of a compound according to Formula (I) or (II), or a pharmaceutically acceptable salt thereof, hydrate, solvate, prodrug, stereoisomer, or tautomer thereof.

In another aspect, the present disclosure relates to a method of treating a disorder or a disease associated with neutral endopeptidase activity in a subject in need thereof, comprising: administering to the subject a therapeutically effective amount of a compound according to Formula (I) or (II), or a pharmaceutically acceptable salt, hydrate, solvate, prodrug, stereoisomer, or tautomer thereof, wherein the compound is administered to patients already or concomitantly being treated with an Angiotensin Receptor Blocker.

In another aspect, the present disclosure relates to a method of treating a disorder or a disease associated with neutral endopeptidase activity in a subject in need thereof, comprising: administering to the subject a therapeutically effective amount of a compound according to Formula (I) or (II), or a pharmaceutically acceptable salt, hydrate, solvate, prodrug, stereoisomer, or tautomer thereof, wherein the compound is administered to patients already or concomitantly being treated with the Angiotensin Receptor Blocker valsartan or a pharmaceutically acceptable salt thereof. In one embodiment, the compound according to Formula (I) or (II), is administered together, concomitantly or sequentially with the Angiotensin Receptor Blocker valsartan, or a pharmaceutically acceptable salt thereof.

In another aspect, the present disclosure relates to the use of a compound according to Formula (I) or (II), or a pharmaceutically acceptable salt, hydrate, solvate, prodrug, stereoisomer, or tautomer thereof, for the treatment of a disorder or a disease associated with neutral endopeptidase activity in a subject in need of such treatment, wherein the compound is administered to patients already or concomitantly being treated with an Angiotensin Receptor Blocker.

In another aspect, the present disclosure relates to the use of a compound according to Formula (I) or (II), or a pharmaceutically acceptable salt, hydrate, solvate, prodrug, stereoisomer, or tautomer thereof, for the treatment of a disorder or a disease associated with neutral endopeptidase activity in a subject in need of such treatment, wherein the compound is administered to patients already or concomitantly being treated with the Angiotensin Receptor Blocker valsartan or a pharmaceutically acceptable salt thereof. In one embodiment, the compound according to Formula (I) or (II), is administered together, concomitantly or sequentially with the Angiotensin Receptor Blocker valsartan, or a pharmaceutically acceptable salt, hydrate, solvate, prodrug, stereoisomer, or tautomer thereof.

Another aspect of the present disclosure relates to a crystalline form A of (4-(((2S,4R)-1-([1,1'-biphenyl]-4-yl)-5-ethoxy-4-methyl-5-oxopentan-2-yl)amino)-4-oxobutanoyl)-L-leucine (I-1) having the structure below:

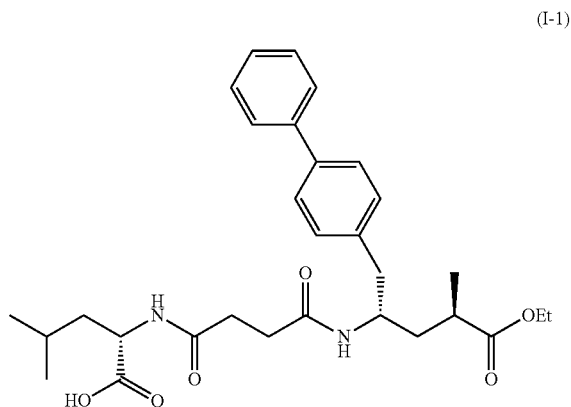 [SMILES: CCOC(=O)[C@H](C)C[C@@H](Cc1ccc(-c2ccccc2)cc1)NC(=O)CCC(=O)N[C@@H](CC(C)C)C(=O)O]

(I-1)

wherein the crystalline form has an X-ray powder diffraction (XPRD) pattern comprising three or more 2-theta peaks selected from 7.1±0.1°, 7.8±0.1°, 8.7±0.1°, 10.7±0.1°, 13.0±0.1°, 15.6±0.1°, 16.0±0.1°, 16.3±0.1°, 17.0±0.1°, 17.3±0.1°, 17.7±0.1°, 18.7±0.1°, 19.2±0.1°, 19.5±0.1°, 20.2±0.1°, 20.9±0.1°, 21.4±0.1°, 21.6±0.1°, 22.4±0.1°, 22.6±0.1°, 22.8±0.1°, 23.4±0.1°, 23.8±0.1°, 24.3±0.1°, 24.9±0.1°, 25.7±0.1°, 26.2±0.1°, 27.2±0.1°, 27.3±0.1°, 27.5±0.1°, 28.5±0.1°, 28.8±0.1°, 29.3±0.1°, 29.8±0.1°, 31.6±0.1°, 32.2±0.1°, 34.1±0.1°, 36.1±0.1°, 36.2±0.1°, 36.9±0.1°, 41.1±0.1°, and 43.8±0.1°.

In another aspect, the present disclosure relates to a crystalline form A of (4-(((2S,4R)-1-([1,1'-biphenyl]-4-yl)-5-ethoxy-4-methyl-5-oxopentan-2-yl)amino)-4-oxobutanoyl)-L-lysine (I-2) having the structure below:

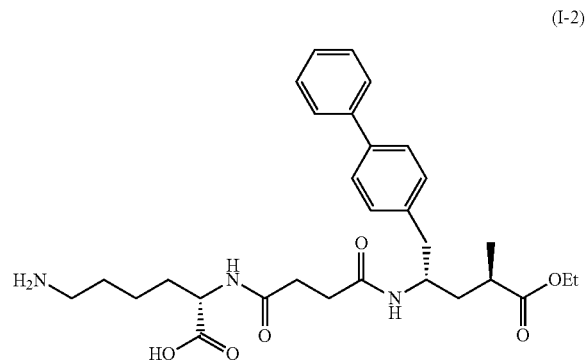 [SMILES: CCOC(=O)[C@H](C)C[C@@H](Cc1ccc(-c2ccccc2)cc1)NC(=O)CCC(=O)N[C@@H](CCCCN)C(=O)O]

(I-2)

wherein the crystalline form has an X-ray powder diffraction (XPRD) pattern comprising three or more 2-theta peaks selected from 10.6±0.1°, 10.8±0.1°, 11.1±0.1°, 12.1±0.1°, 12.2±0.1°, 13.4±0.1°, 13.6±0.1°, 15.1±0.1°, 16.0±0.1°, 16.1±0.1°, 16.7±0.1°, 16.7±0.1°, 17.1±0.1°, 19.2±0.1°, 19.9±0.1°, 20.7±0.1°, 20.8±0.1°, 21.2±0.1°, 21.3±0.1°, 21.6±0.1°, 21.9±0.1°, 22.1±0.1°, 22.5±0.1°, 23.2±0.1°, 23.3±0.1°, 24.0±0.1°, 24.3±0.1°, 25.0±0.1°, 26.9±0.1°, 27.1±0.1°, 27.5±0.1°, 28.8±0.1°, and 29.1±0.1.

In another aspect, the present disclosure relates to a crystalline form B of (4-(((2S,4R)-1-([1,1'-biphenyl]-4-yl)-5-ethoxy-4-methyl-5-oxopentan-2-yl)amino)-4-oxobutanoyl)-L-lysine (I-2) wherein the crystalline form has an X-ray powder diffraction (XPRD) pattern comprising three or more 2-theta peaks selected from 8.7±0.1°, 9.3±0.1°, 12.4±0.1°, 13.5±0.1°, 14.8±0.1°, 15.5±0.1°, 16.2±0.1°, 16.6±0.1°, 16.9±0.1°, 17.5±0.1°, 18.0±0.1°, 18.6±0.1°, 18.9±0.1°, 20.5±0.1°, 21.8±0.1°, 23.3±0.1°, 23.7±0.1°, 24.8±0.1°, 25.0±0.10, 25.7±0.1°, 26.3±0.1°, 28.1±0.1°, 28.6±0.1°, 32.3±0.1°, 32.9±0.1°, 37.3±0.1°, 38.7±0.1°, and 39.9±0.1°.

In another aspect, the present disclosure relates to a crystalline form of a succinate salt of (tert-butyl (4-(((2S, 4R)-1-([1,1'-biphenyl]-4-yl)-5-ethoxy-4-methyl-5-oxopentan-2-yl)amino)-4-oxobutanoyl)-L-lysinate (I-3) having the structure below:

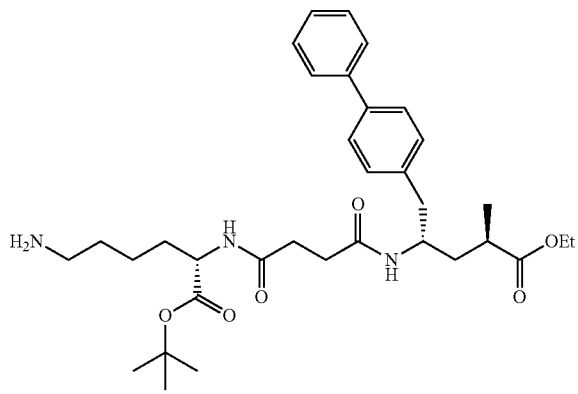

(I-3)

wherein the crystalline form has an X-ray powder diffraction (XPRD) pattern comprising three or more 2-theta peaks selected from 8.5±0.1°, 11.2±0.1°, 12.7±0.1°, 13.4±0.1°, 14.8±0.1°, 16.1±0.1°, 16.9±0.1°, 18.1±0.1°, 19.2±0.1°, 19.6±0.1°, 20.1±0.1°, 20.8±0.1°, 20.9±0.1°, 21.8±0.1°, 22.5±0.1°, 23.6±0.1°, 24.4±0.1°, 25.6±0.1°, 26.4±0.1°, 26.7±0.1°, 27.6±0.1°, 28.5±0.1°, 31.6±0.1°, and 32.4±0.1°.

In another aspect, the present disclosure relates to a crystalline form of a malonate salt of (tert-butyl (4-(((2S, 4R)-1-([1,1'-biphenyl]-4-yl)-5-ethoxy-4-methyl-5-oxopentan-2-yl)amino)-4-oxobutanoyl)-L-lysinate (I-3), wherein the crystalline form has an X-ray powder diffraction (XPRD) pattern comprising three or more 2-theta peaks selected from 8.7±0.1°, 10.8±0.1°, 11.5±0.1°, 13.1±0.1°, 13.7±0.1°, 15.2±0.1°, 15.7±0.1°, 15.8±0.1°, 17.4±0.1°, 18.4±0.1°, 19.1±0.1°, 19.4±0.1°, 19.4±0.1°, 19.7±0.1°, 20.4±0.1°, 21.3±0.1°, 21.7±0.1°, 22.3±0.1°, 23.0±0.1°, 24.1±0.1°, 24.7±0.1°, 26.6±0.1°, 26.8±0.1°, 27.5±0.1°, 28.5±0.1°, 28.6±0.1°, 32.4±0.1°, and 33.3±0.1°.

In another aspect, the present disclosure relates to a crystalline form of a fumarate salt of (tert-butyl (4-(((2S, 4R)-1-([1,1'-biphenyl]-4-yl)-5-ethoxy-4-methyl-5-oxopentan-2-yl)amino)-4-oxobutanoyl)-L-lysinate (I-3), wherein the crystalline form has an X-ray powder diffraction (XPRD) pattern comprising three or more 2-theta peaks selected from 6.6±0.1°, 8.8±0.1°, 13.1±0.1°, 13.2±0.1°, 10.6±0.1°, 15.4±0.1°, 17.7±0.1°, 19.2±0.1°, 20.2±0.1°, 22.1±0.1°, 24.7±0.1°, 26.5±0.1°, and 28.9±0.1°.

Another aspect of the present disclosure relates to a pharmaceutical composition comprising a crystalline form of I-1, I-2, or I-3, or a crystalline form of a pharmaceutically acceptable salt of I-1, I-2, or I-3 and one or more pharmaceutically acceptable carriers.

In another aspect, the present disclosure relates to combination comprising: a crystalline form of I-1, I-2, or I-3, or a crystalline form of a pharmaceutically acceptable salt of I-1, I-2, or I-3 and one or more therapeutically active agents selected from HMG-Co-A reductase inhibitor, an angiotensin receptor blocker, a calcium channel blocker, an endothelin antagonist, a renin inhibitor, a diuretic, an ApoA-I mimic, an anti-diabetic agent, an obesity-reducing agent, an aldosterone receptor blocker, an endothelin receptor blocker, an aldosterone synthase inhibitor, a CETP inhibitor, and a phosphodiesterase type 5 (PDE5) inhibitor.

Another aspect of the present disclosure relates to a method of inhibiting neutral endopeptidase activity in a subject in need thereof, comprising: administering to the subject a therapeutically effective amount of a crystalline form of I-1, I-2) or I-3, or a crystalline form of a pharmaceutically acceptable salt of I-1, I-2, or I-3.

In another aspect, the present disclosure relates to a method of treating a disorder or a disease associated with neutral endopeptidase activity in a subject in need thereof, comprising: administering to the subject a therapeutically effective amount of a crystalline form of I-1, I-2, or I-3, or a crystalline form of a pharmaceutically acceptable salt of I-1, I-2, or I-3.

Another aspect of the present disclosure relates to a crystalline form of I-1, I-2, or I-3, or a crystalline form of a pharmaceutically acceptable salt of I-1, I-2, or I-3 for use as a medicament.

In another aspect, the present disclosure relates to the use of a crystalline form of I-1, I-2, or I-3, or a crystalline form of a pharmaceutically acceptable salt of I-1, I-2, or I-3 for the treatment of a disorder or disease associated with neutral endopeptidase activity in a subject in need of such treatment.

In another aspect, the present disclosure relates to a method of treating a disorder or a disease associated with neutral endopeptidase activity in a subject in need thereof, comprising: administering to the subject a therapeutically effective amount of a crystalline form of I-1, I-2, or I-3, or a crystalline form of a pharmaceutically acceptable salt of I-1, I-2, or I-3, wherein the crystalline form is administered to patients already or concomitantly being treated with an Angiotensin Receptor Blocker.

In another aspect, the present disclosure relates to a method of treating a disorder or a disease associated with neutral endopeptidase activity in a subject in need thereof, comprising: administering to the subject a therapeutically effective amount of a crystalline form of I-1, I-2, or I-3, or a crystalline form of a pharmaceutically acceptable salt of I-1, I-2, or I-3, wherein the crystalline form is administered to patients already or concomitantly being treated with the Angiotensin Receptor Blocker valsartan or a pharmaceutically acceptable salt thereof. In one embodiment, the crystalline form is administered together, concomitantly or sequentially with the Angiotensin Receptor Blocker valsartan, or a pharmaceutically acceptable salt thereof.

In another aspect, the present disclosure relates the use of a crystalline form of I-1, I-2, or I-3, or a crystalline form of a pharmaceutically acceptable salt of I-1, I-2, or I-3, for the treatment of a disorder or a disease associated with neutral endopeptidase activity in a subject in need of such treatment, wherein the crystalline form is administered to patients already or concomitantly being treated with an Angiotensin Receptor Blocker.

In another aspect, the present disclosure relates to the use of a crystalline form of I-1, I-2, or I-3, or a crystalline form of a pharmaceutically acceptable salt of I-1, I-2, or I-3, for the treatment of a disorder or a disease associated with neutral endopeptidase activity in a subject in need of such treatment, wherein the crystalline form is administered to patients already or concomitantly being treated with the Angiotensin Receptor Blocker valsartan or a pharmaceutically acceptable salt thereof. In one embodiment, the crystalline form is administered together, concomitantly or sequentially with the Angiotensin Receptor Blocker valsartan, or a pharmaceutically acceptable salt thereof.

DETAILED DESCRIPTION OF THE DISCLOSURE

Figure 1:
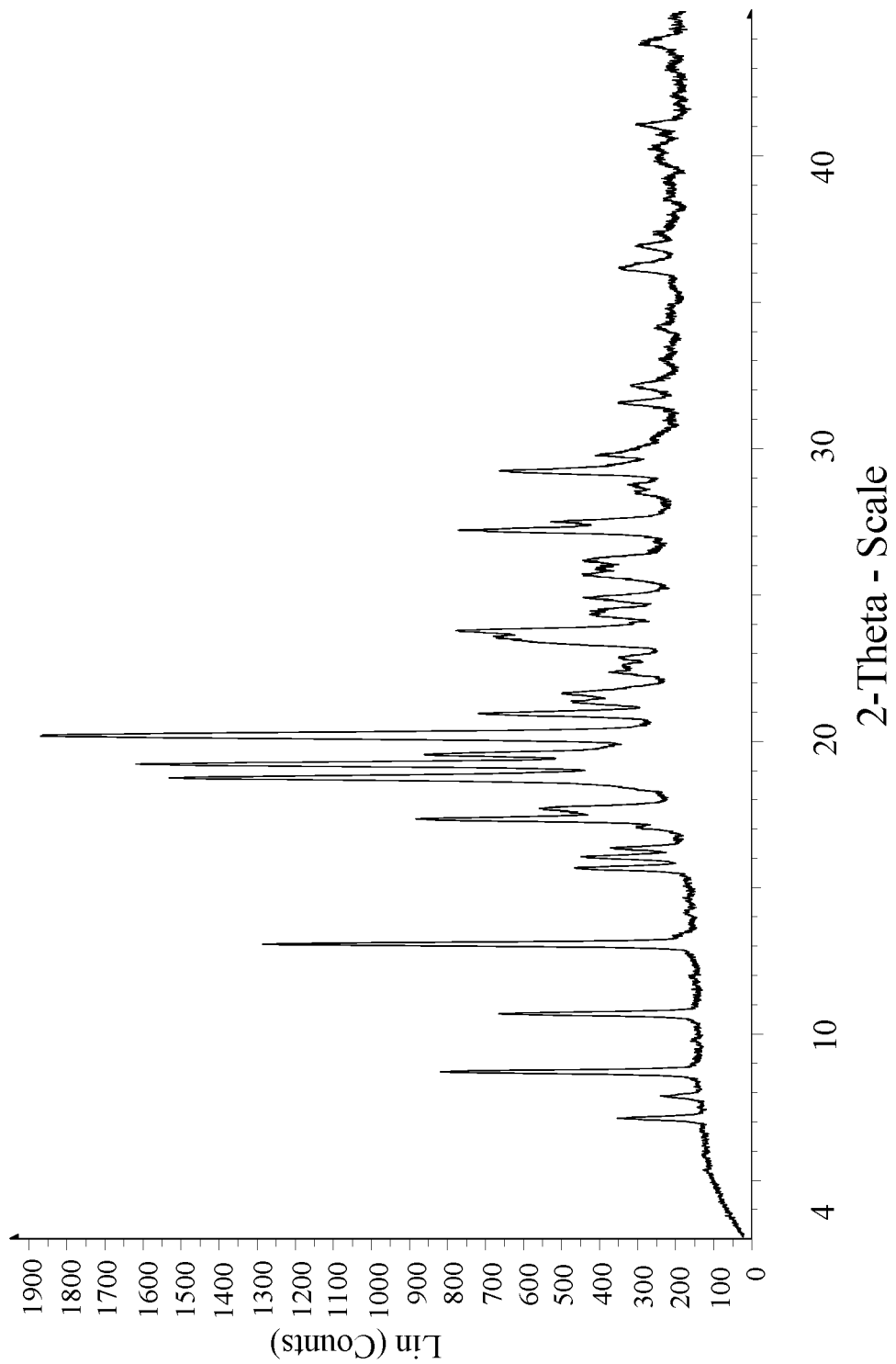
FIG. 1 illustrates the x-ray powder diffraction patterns of a Crystalline Form A of compound I-1 in Example 1.

The present disclosure relates to compounds improved physio-chemical properties and which deliver profiles of NEP inhibition optimal for specific disease stages. In particular, prolonged exposure and reduced potential for Cmax which may be desirable in certain disease conditions and for certain patient populations. The NEP inhibitors of the instant disclosure deliver unique profiles of NEP inhibition. In addition, the compounds of the disclosure exhibit favorable physio-chemical properties making them particularly amenable for industrial manufacturing needed to deliver the medicines at affordable prices to patients. The disclosure also related to compositions that are capable of modulating NEP protein levels with prolonged exposure and reduced potential for Cmax-driving adverse effects. The NEP inhibitors of the instant disclosure favorable physio-chemical properties and have exposure profiles desirable in specific patient populations, for potentially improving the safety profile and for use with less frequent dosing as needed. The disclosure features methods of treating, preventing, or ameliorating a disease or disorder in which NEP plays a role by administering to a patient in need thereof a therapeutically effective amount of a compound of Formula (I) or (II), or a pharmaceutically acceptable salt, hydrate, solvate, prodrug, stereoisomer, or tautomer thereof. The methods of the present disclosure can be used in the treatment of a variety of NEP-dependent diseases and disorders by modulating NEP.

In a first aspect of the disclosure, the compounds of Formula (I) are described:

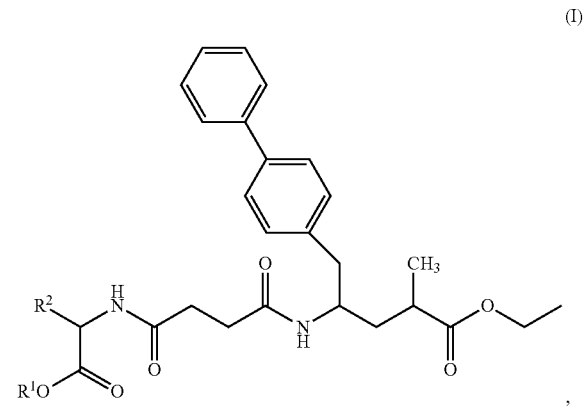

(I)

or pharmaceutically acceptable salts, hydrates, solvates, prodrugs, stereoisomers, and tautomers thereof, wherein $R^1$ and $R^2$ are as described herein.

Definition

For purposes of interpreting this specification, the following definitions will apply unless specified otherwise and whenever appropriate, terms used in the singular will also include the plural and vice versa.

The term "and/or" means either "and" or "or" unless indicated otherwise.

The term "optionally substituted" means that a given chemical moiety (e.g., an alkyl group) can (but is not required to) be bonded to other substituents (e.g., heteroatoms). For instance, an alkyl group that is optionally substituted can be a fully saturated alkyl chain (e.g., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus, the term "optionally substituted" means that a given chemical moiety has the potential to contain other functional groups (e.g., a given chemical moiety substituted or unsubstituted), but does not necessarily have any further functional groups. Suitable substituents used in the optional substitution of the described groups include, without limitation, halogen, oxo, —OH, —CN, —COOH, —CH$_2$CN, —O—($C_1$-$C_6$)alkyl, ($C_1$-$C_6$)alkyl, ($C_1$-$C_6$)alkoxy, ($C_1$-$C_6$)haloalkyl, ($C_1$-$C_6$)haloalkoxy, —O—($C_2$-$C_6$)alkenyl, —O—($C_2$-$C_6$)alkynyl, ($C_2$-$C_6$)alkenyl, ($C_2$-$C_6$)alkynyl, —OH, —OP(O)(OH)$_2$, —OC(O)($C_1$-$C_6$)alkyl, —C(O)($C_1$-$C_6$)alkyl, —OC(O)O($C_1$-$C_6$)alkyl, —NH$_2$, —NH(($C_1$-$C_6$)alkyl), —N(($C_1$-$C_6$)alkyl)$_2$, —NHC(O)($C_1$-$C_6$)alkyl, —C(O)NH($C_1$-$C_6$)alkyl, —S(O)$_2$($C_1$-$C_6$)alkyl, —S(O)NH($C_1$-$C_6$)alkyl, and S(O)N(($C_1$-$C_6$)alkyl)$_2$. The substituents can themselves be optionally substituted. "Optionally substituted" as used herein also refers to substituted or unsubstituted whose meaning is described below.

The term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

The term "unsubstituted" means that the specified group bears no substituents.

As used herein, the term "alkyl" refers to a fully saturated branched or unbranched (or straight chain or linear) hydrocarbon moiety, comprising 1 to 7 carbon atoms. Preferably the alkyl comprises 1 to 4 carbon atoms. Representative examples of alkyl include methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl. The term "($C_1$-$C_7$)alkyl" refers to a hydrocarbon having from one to seven carbon atoms. Similarly, the term "($C_1$-$C_4$)alkyl" refers to a hydrocarbon having from one to four carbon atoms.

The term "aryl" refers to monocyclic or bicyclic aromatic hydrocarbon groups having 6-10 carbon atoms in the ring portion. The term "aryl" also refers to a group in which the aromatic ring is fused to a cycloalkyl ring, where the radical of attachment is on the aromatic ring or on the fused cycloalkyl ring. Representative examples of aryl are phenyl, naphthyl, hexahydroindyl, indanyl or tetrahydronaphthyl. The term "($C_6$-$C_{10}$)aryl" refers to an aromatic hydrocarbon group having 6 to 10 carbon atoms in the ring portion. An aryl moiety may be specified to be unsubstituted or substituted. Examples of substituents are halo, ($C_1$-$C_7$)alkyl, halo-($C_1$-$C_7$)alkyl, ($C_1$-$C_7$)alkoxy.

As used herein, the term "cycloalkyl" refers to saturated or unsaturated but non-aromatic monocyclic, bicyclic or tricyclic hydrocarbon groups of 3-12 carbon atoms, preferably 3-8, or 3-7 carbon atoms. For bicyclic and tricyclic cycloalkyl system, all rings are non-aromatic. Exemplary monocyclic hydrocarbon groups include cyclopropyl, cyclobutyl, cyclopentyl, cyclopentenyl, cyclohexyl and cyclohexenyl. Exemplary bicyclic hydrocarbon groups include bornyl, decahydronaphthyl, bicyclo[2.1.1]hexyl, bicyclo[2.2.1]heptyl, bicyclo[2.2.1]heptenyl, bicyclo[2.2.2]octyl. Exemplary tricyclic hydrocarbon groups include adamantyl. The term "($C_3$-$C_7$)cycloalkyl" refers to a cyclic hydrocarbon group having 3 to 7 carbon atoms.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-6, more preferably about 1-4 carbons. The term "($C_1$-$C_7$)alkoxy" refers to an alkoxy group having from one to seven carbon atoms. The term "($C_1$-$C_4$)alkoxy" refers to an alkoxy group having from one to four carbon atoms.

The term "5- to 10-membered monocyclic or bicyclic heteroaryl comprising 1-3 heteroatoms selected from N, O, and S" refers to a 5-, 6- or 7-membered monocyclic aromatic ring system containing 1, 2 or 3 ring heteroatoms independently selected from O, N and S or an 8-, 9- or 10-membered fused bicyclic ring system containing 1, 2 or 3 ring heteroatoms independently selected from O, N or S. The S and N ring heteroatoms may be oxidized to various oxidation states. For a bicyclic heteroaryl system, the system is fully aromatic (i.e., all rings are aromatic). The term "5- or 6-membered heteroaryl comprising 1-3 heteroatoms selected from N, O, and S" is to be construed accordingly. A heteroaryl moiety may be specified to be unsubstituted or substituted. Examples of substituents are halo, ($C_1$-$C_7$)alkyl, halo-($C_1$-$C_7$)alkyl, ($C_1$-$C_7$)alkoxy, etc.

Halogen or "halo" means fluorine, chlorine, bromine, or iodine.

The term "heteroatom" includes atoms of any element other than carbon or hydrogen. Preferred heteroatoms are nitrogen, oxygen, sulfur and phosphorus. In another embodiment, the heteroatom is nitrogen, oxygen or sulfur.

As used herein, the term "haloalkyl" means an alkyl group substituted with one or more halogens. Examples of haloalkyl groups include, but are not limited to, trifluoromethyl, difluoromethyl, pentafluoroethyl, trichloromethyl, etc.

As used herein, the term "haloalkoxy" means an alkoxy group substituted with one or more halogens. Examples of haloalkoxy groups include, but are not limited to, trifluoromethoxy, difluoromethoxy, pentafluoroethoxy, trichloromethoxy, etc.

As used herein, the term "cyano" means a substituent having a carbon atom joined to a nitrogen atom by a triple bond, i.e., C≡N.

As used herein, the term "amino" means a substituent containing at least one nitrogen atom (e.g., NH$_2$).

As used herein, the term "alkylamino" means an amino or NH$_2$ group where one of the hydrogens is replaced with an alkyl group, e.g., —NH(alkyl). Examples of alkylamino groups include, but are not limited to, methylamino (e.g., —NH(CH$_3$)), ethylamino, propylamino, iso-propylamino, n-butylamino, sec-butylamino, tert-butylamino, etc.

As used herein, the term "dialkylamino" means an amino or NH$_2$ group where both of the hydrogens are replaced with alkyl groups, e.g., —N(alkyl)$_2$. The alkyl groups on the amino group are the same or different alkyl groups. Examples of dialkylamino groups include, but are not limited to, dimethylamino (e.g., —N(CH$_3$)$_2$), diethylamino, dipropylamino, diiso-propylamino, di-n-butylamino, di-sec-butylamino, di-tert-butylamino, methyl(ethyl)amino, methyl (butylamino), etc.

The compound "AHU377" 4-(((2S,4R)-1-([1,1'-biphenyl]-4-yl)-5-ethoxy-4-methyl-5-oxopentan-2-yl)amino)-4- oxobutanoic acid also known as sacubitril is a small molecule NEP inhibitor having the following structure:

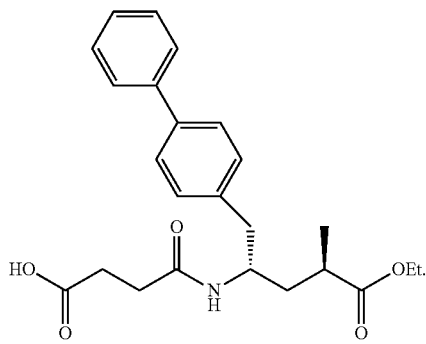

The compound "LBQ657" (2R,4S)-5-([1,1'-biphenyl]-4-yl)-4-(3-carboxypropanamido)-2-methylpentanoic acid also known as Sacubitrilat is a small molecule NEP inhibitor having the following structure:

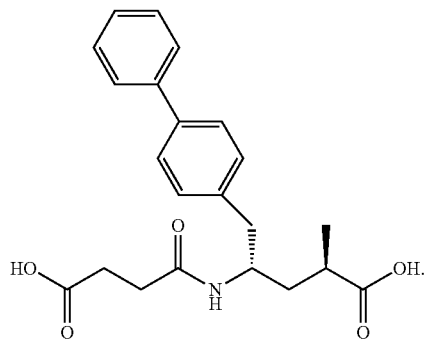 [SMILES: CCOC(=O)[C@H](C)C[C@@H](Cc1ccc(-c2ccccc2)cc1)NC(=O)CCC(=O)O]

"Salt" means an ionic form of the parent compound or the product of the reaction between the parent compound with a suitable acid or base to make the acid salt or base salt of the parent compound. Salts of the compounds of the present disclosure can be synthesized from the parent compounds which contain a basic or acidic moiety by conventional chemical methods. Generally, the salts are prepared by reacting the free base or acid parent compound with stoichiometric amounts or with an excess of the desired salt-forming inorganic or organic acid or base in a suitable solvent or various combinations of solvents.

"Pharmaceutically acceptable salt" means a salt of a compound of the disclosure which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. As the compounds of the present disclosure are useful in both free base and salt form, in practice, the use of the salt form amounts to use of the base form. Lists of suitable salts are found in, e.g., S. M. Birge et al., J. Pharm. Sci., 1977, 66, pp. 1-19, which is hereby incorporated by reference in its entirety.

"Pharmaceutically-acceptable acid addition salt" means those salts which retain the biological effectiveness and properties of the free bases and which are not biologically or otherwise undesirable. Pharmaceutically acceptable acid addition salts can be formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, undecanoic acid, and the like.

"Pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

As used herein, the term "pharmaceutical composition" refers to a compound of the disclosure, or a pharmaceutically acceptable salt, hydrate, solvate, prodrug, stereoisomer, or tautomer thereof, together with at least one pharmaceutically acceptable carrier, in a form suitable for oral or parenteral administration.

As used herein, the term "carrier" or "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

A subject is "in need of" a treatment if such subject would benefit biologically, medically, or in quality of life from such treatment (preferably, a human).

As used herein, the term "inhibit", "inhibition", or "inhibiting" refers to the reduction or suppression of a given condition, symptom, or disorder, or disease, or a significant decrease in the baseline activity of a biological activity or process.

As used herein, the term "treat", "treating", or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing", or "prevention" of any disease or disorder refers to the prophylactic treatment of the disease or disorder; or delaying the onset or progression of the disease or disorder.

The term "a therapeutically effective amount" of a compound of the present disclosure refers to an amount of the compound of the present disclosure that will elicit the biological or medical response of a subject, for example, reduction or inhibition of an enzyme or a protein activity, or amelioration of a symptom, alleviation of a condition, slow or delay disease progression, or prevention of a disease, etc. In one non-limiting embodiment, the term "a therapeutically effective amount" refers to the amount of the compound of the present disclosure that, when administered to a subject, is effective to (1) at least partially alleviate, inhibit, prevent and/or ameliorate a condition, a disorder or a disease or a symptom thereof (i) ameliorated by the inhibition of neutral endopeptidase or (ii) associated with neutral endopeptidase activity, or (iii) characterized by abnormal activity of neutral endopeptidase; or (2) reduce or inhibit the activity of neutral endopeptidase; or (3) reduce or inhibit the expression of neutral endopeptidase. In another non-limiting embodiment, the term "a therapeutically effective amount" refers to the amount of the compound of the present disclosure that, when administered to a cell, or a tissue, or a non-cellular biological material, or a medium, is effective to at least partially reduce or inhibit the activity of neutral endopeptidase; or at least partially reduce or inhibit the expression of neutral endopeptidase.

The terms "patient" include, but are not limited to, humans, dogs, cats, horses, pigs, cows, monkeys, rabbits and mice. The preferred patients are humans.

"Disorder" means, and is used interchangeably with, the terms disease, condition, or illness, unless otherwise indicated.

The terms "administration of" and or "administering a" compound should be understood to mean providing a compound of the disclosure or a pharmaceutically acceptable salt or ester thereof, or a pro-drug thereof to a subject in need of treatment. The administration of the composition of the present disclosure in order to practice the present methods of therapy is carried out by administering a therapeutically effective amount of the compounds in the composition to a subject in need of such treatment or prophylaxis. The need for a prophylactic administration according to the methods of the present disclosure is determined via the use of well-known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgment.

The term "prophylactically effective amount" as used herein means the amount of the active compounds in the composition that will elicit the biological or medical response in a tissue, system, subject, or human that is being sought by the researcher, veterinarian, medical doctor or other clinician, to prevent the onset of a disease characterized and/or manifested by atrial enlargement and/or remodeling.

The term "pharmaceutically acceptable", as used herein, refers to those compounds, materials, compositions and/or dosage forms, which are, within the scope of sound medical judgment, suitable for contact with the tissues of mammals, especially humans, without excessive toxicity, irritation, allergic response and other problem complications commensurate with a reasonable benefit/risk ratio.

"Prodrug" means a compound which is convertible in vivo by metabolic means (e.g., by hydrolysis) to a disclosed compound.

The present disclosure also provides pro-drugs of the compounds of the present disclosure that convert in vivo to the compounds of the present disclosure. A pro-drug is an active or inactive compound that is modified chemically through in vivo physiological action, such as hydrolysis, metabolism and the like, into a compound of this disclosure following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See The Practice of Medicinal Chemistry, Ch. 31-32 (Ed. Wermuth, Academic Press, San Diego, Calif., 2001). Generally, bioprecursor prodrugs are compounds, which are inactive or have low activity compared to the corresponding active drug compound that contain one or more protective groups and are converted to an active form by metabolism or solvolysis. Both the active drug form and any released metabolic products should have acceptably low toxicity. Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug Formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω (amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, J. Med. Chem. 2503 (1989)). Moreover, drugs containing an acidic NH group, such as imidazole, imide, indole and the like, have been masked with N-acyloxymethyl groups (Bundgaard, Design of Prodrugs, Elsevier (1985)). Hydroxy groups have been masked as esters and ethers. EP 039,051 (Sloan and Little) discloses Mannich-base hydroxamic acid prodrugs, their preparation and use.

"Pharmaceutically acceptable prodrug" as used herein means a prodrug of a compound of the disclosure which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

"Salt" means an ionic form of the parent compound or the product of the reaction between the parent compound with a suitable acid or base to make the acid salt or base salt of the parent compound. Salts of the compounds of the present disclosure can be synthesized from the parent compounds which contain a basic or acidic moiety by conventional chemical methods. Generally, the salts are prepared by reacting the free base or acid parent compound with stoichiometric amounts or with an excess of the desired salt-forming inorganic or organic acid or base in a suitable solvent or various combinations of solvents.

"Compounds of the present disclosure", "Compounds of Formula (I)", "compounds of the disclosure", and equivalent expressions (unless specifically identified otherwise) refer to compounds of Formula (I) and (II) as herein described including the tautomers, the prodrugs, salts particularly the pharmaceutically acceptable salts, and the solvates and hydrates thereof, where the context so permits thereof, as well as all stereoisomers (including diastereoisomers and enantiomers), rotamers, tautomers, and isotopically labelled compounds (including deuterium substitutions), as well as inherently formed moieties (e.g., polymorphs, solvates and/or hydrates). For purposes of this disclosure, solvates and hydrates are generally considered compositions. In general and preferably, the compounds of the disclosure and the formulas designating the compounds of the disclosure are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits.

The compounds of the present disclosure, including their salts, may also be obtained in the form of their hydrates, or include other solvents used for their crystallization. The compounds of the present disclosure may inherently or by design form solvates with pharmaceutically acceptable solvents (including water); therefore, it is intended that the both solvated and unsolvated forms are embraced by the disclosure herein. The term "solvate" refers to a molecular complex of a compound of the present disclosure (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

"Stable compound" or "stable structure" means a compound that is sufficiently robust to survive isolation to a useful degree of purity from a reaction mixture, and formulation into an efficacious therapeutic or diagnostic agent. For example, a compound which would have a "dangling valency" or is a carbanion is not a compound contemplated by the disclosure.

In a specific embodiment, the term "about" or "approximately" means within 20%, preferably within 10%, and more preferably within 5% of a given value or range.

The New York Heart Association (NYHA) classification grades the severity of heart failure symptoms as one of four functional classes. The NYHA classification is widely used in clinical practice and in research because it provides a standard description of severity that can be used to assess response to treatment and to guide management. The New York Heart Association functional classification based on severity of symptoms and physical activity:

Class I: No limitation of physical activity. Ordinary physical activity does not cause undue breathlessness, fatigue, or palpitations.

Class II: Slight limitation of physical activity. Comfortable at rest, but ordinary physical activity results in undue breathlessness, fatigue, or palpitations.

Class III: Marked limitation of physical activity. Comfortable at rest, but less than ordinary physical activity results in undue breathlessness, fatigue, or palpitations.

Class IV: Unable to carry on any physical activity without discomfort. Symptoms at rest can be present. If any physical activity is undertaken, discomfort is increased. Choice of endpoints: Cardiovascular death and heart failure hospitalization both reflect disease-specific endpoints related to progressive worsening of the heart failure syndrome, and experienced by patients with systolic heart failure. These endpoints can be modified by treatments improving this condition, which has generally proved to be the case with drugs such as ACEIs, aldosterone antagonists, and β-blockers as well as devices for cardiac resynchronization therapy.

Compounds of the Disclosure:

Various embodiments of the disclosure are described herein. It will be recognized that features specified in each embodiment may be combined with other specified features to provide further embodiments.

In an embodiment, a compound of Formula (I) or Formula (II), or a pharmaceutically acceptable salt thereof, is provided.

In one embodiment, the compounds of Formula (I) have the structure of Formula (II):

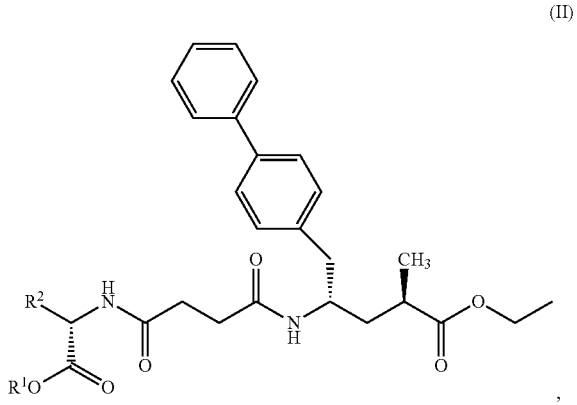

(II)

wherein:

$R^1$ is H or $(C_1\text{-}C_4)$alkyl;

$R^2$ is H, $(C_1\text{-}C_4)$alkyl, $(C_6\text{-}C_{10})$ aryl, or 5- or 6-membered heteroaryl comprising 1-3 heteroatoms selected from N, S, and O, wherein the alkyl is optionally substituted with one or more $R^3$, and wherein the aryl and heteroaryl are optionally substituted with one or more $R^4$;

each $R^3$ is independently at each occurrence —$NH_2$, $(C_1\text{-}C_4)$alkylamino, $(C_1\text{-}C_4)$dialkylamino, —OH, —SH, —S$(C_1\text{-}C_4)$alkyl, —$CO_2H$, —$CONH_2$, —NHC(NH)$NH_2$, $(C_6\text{-}C_{10})$ aryl, or 5- to 10-membered monocyclic or bicyclic heteroaryl comprising 1-3 heteroatoms selected from N, O, and S, wherein the aryl and heteroaryl are optionally substituted with one or more $R^5$;

each $R^4$ is independently at each occurrence $(C_1\text{-}C_4)$alkyl, $(C_1\text{-}C_4)$haloalkyl, $(C_1\text{-}C_4)$alkoxy, $(C_1\text{-}C_4)$haloalkoxy, halogen, —$NH_2$, —OH or CN; and each $R^5$ is independently at each occurrence $(C_1\text{-}C_4)$alkyl, $(C_1\text{-}C_4)$haloalkyl, $(C_1\text{-}C_4)$alkoxy, $(C_1\text{-}C_4)$haloalkoxy, halogen, —$NH_2$, —OH or CN;

or pharmaceutically acceptable salts, hydrates, solvates, prodrugs, stereoisomers, and tautomers thereof.

In an embodiment, with respect to formulae (I) or (II), $R^1$ is H or $(C_1\text{-}C_4)$alkyl;

$R^2$ is $(C_1\text{-}C_4)$alkyl, $(C_6\text{-}C_{10})$ aryl, or 5- or 6-membered heteroaryl comprising 1-3 heteroatoms selected from N, S, and O, wherein the alkyl is optionally substituted with one or more $R^3$, and wherein the aryl and heteroaryl are optionally substituted with one or more $R^4$;

each $R^3$ is independently at each occurrence —$NH_2$, $(C_1\text{-}C_4)$alkylamino, $(C_1\text{-}C_4)$dialkylamino, —OH, —SH, —S$(C_1\text{-}C_4)$alkyl, —$CO_2H$, —$CONH_2$, —NHC(NH)$NH_2$, $(C_6\text{-}C_{10})$ aryl, or 5- to 10-membered monocyclic or bicyclic heteroaryl comprising 1-3 heteroatoms selected from N, O, and S, wherein the aryl and heteroaryl are optionally substituted with one or more $R^5$;

each $R^4$ is independently at each occurrence $(C_1\text{-}C_4)$alkyl, $(C_1\text{-}C_4)$haloalkyl, $(C_1\text{-}C_4)$alkoxy, $(C_1\text{-}C_4)$haloalkoxy, halogen, —$NH_2$, —OH or CN; and each $R^5$ is independently at each occurrence $(C_1\text{-}C_4)$alkyl, $(C_1\text{-}C_4)$haloalkyl, $(C_1\text{-}C_4)$alkoxy, $(C_1\text{-}C_4)$haloalkoxy, halogen, —$NH_2$, —OH or CN;

or pharmaceutically acceptable salts, hydrates, solvates, prodrugs, stereoisomers, and tautomers thereof.

In an embodiment with respect to formulae (I) or (II), $R^1$ is H or $(C_1\text{-}C_4)$alkyl; $R^2$ is $(C_1\text{-}C_4)$alkyl, $(C_6\text{-}C_{10})$ aryl, or 5- or 6-membered heteroaryl comprising 1-3 heteroatoms selected from N, S, and O, wherein the alkyl is optionally substituted with one to four $R^3$, and wherein the aryl and heteroaryl are optionally substituted with one to four $R^4$;

each $R^3$ is independently at each occurrence —$NH_2$, $(C_1\text{-}C_4)$alkylamino, $(C_1\text{-}C_4)$dialkylamino, —OH, —SH, —S$(C_1\text{-}C_4)$alkyl, —$CO_2H$, —$CONH_2$, —NHC(NH)$NH_2$, $(C_6\text{-}C_{10})$ aryl, or 5- to 10-membered monocyclic or bicyclic heteroaryl comprising 1-3 heteroatoms selected from N, O, and S, wherein the aryl and heteroaryl are optionally substituted with one to four $R^5$; each $R^4$ is independently at each occurrence $(C_1\text{-}C_4)$alkyl, $(C_1\text{-}C_4)$haloalkyl, $(C_1\text{-}C_4)$alkoxy, $(C_1\text{-}C_4)$haloalkoxy, halogen, —$NH_2$, —OH or CN; and each $R^5$ is independently at each occurrence $(C_1\text{-}C_4)$alkyl, $(C_1\text{-}C_4)$haloalkyl, $(C_1\text{-}C_4)$alkoxy, $(C_1\text{-}C_4)$haloalkoxy, halogen, —$NH_2$, —OH or CN; or pharmaceutically acceptable salts, hydrates, solvates, prodrugs, stereoisomers, and tautomers thereof.

In an embodiment with respect to formulae (I) or (II), $R^1$ is H or $(C_1\text{-}C_4)$alkyl; $R^2$ is H, $(C_1\text{-}C_4)$alkyl, $(C_6\text{-}C_{10})$ aryl, or 5- or 6-membered heteroaryl comprising 1-3 heteroatoms selected from N, S, and O, wherein the alkyl is optionally substituted with one to four $R^3$, and wherein the aryl and heteroaryl are optionally substituted with one to four $R^4$;

each $R^3$ is independently at each occurrence —$NH_2$, $(C_1\text{-}C_4)$alkylamino, $(C_1\text{-}C_4)$dialkylamino, —OH, —SH, —S$(C_1\text{-}C_4)$alkyl, —$CO_2H$, —$CONH_2$, —NHC(NH)$NH_2$, $(C_6\text{-}C_{10})$ aryl, or 5- to 10-membered monocyclic or bicyclic heteroaryl comprising 1-3 heteroatoms selected from N, O, and S, wherein the aryl and heteroaryl are optionally substituted with one to four $R^5$; each $R^4$ is independently at each occurrence $(C_1\text{-}C_4)$alkyl, $(C_1\text{-}C_4)$haloalkyl, $(C_1\text{-}C_4)$alkoxy, $(C_1\text{-}C_4)$haloalkoxy, halogen, —$NH_2$, —OH or CN; and each $R^5$ is independently at each occurrence $(C_1\text{-}C_4)$alkyl, $(C_1\text{-}C_4)$haloalkyl, $(C_1\text{-}C_4)$alkoxy, $(C_1\text{-}C_4)$haloalkoxy, halogen, —$NH_2$, —OH or CN; or pharmaceutically acceptable salts, hydrates, solvates, prodrugs, stereoisomers, and tautomers thereof.

In an embodiment with respect to formulae (I) or (II), $R^1$ is H or $(C_1\text{-}C_4)$alkyl; $R^2$ is H or $(C_1\text{-}C_4)$alkyl, wherein the alkyl is optionally substituted with one to four $R^3$; each $R^3$ is independently at each occurrence —$NH_2$, $(C_1\text{-}C_4)$alkylamino, $(C_1\text{-}C_4)$dialkylamino, —OH, —SH, —S$(C_1\text{-}C_4)$alkyl, —$CO_2H$, —$CONH_2$, —NHC(NH)$NH_2$, $(C_6\text{-}C_{10})$ aryl, or 5- to 10-membered monocyclic or bicyclic heteroaryl comprising 1-3 heteroatoms selected from N, O, and S, wherein the aryl and heteroaryl are optionally substituted with one to four $R^5$; and each $R^5$ is independently at each occurrence $(C_1\text{-}C_4)$alkyl, $(C_1\text{-}C_4)$haloalkyl, $(C_1\text{-}C_4)$alkoxy, $(C_1\text{-}C_4)$haloalkoxy, halogen, —$NH_2$, —OH or CN; or pharmaceutically acceptable salts, hydrates, solvates, prodrugs, stereoisomers, and tautomers thereof.

In an embodiment with respect to formulae (I) or (II), $R^1$ is H or $(C_1\text{-}C_4)$alkyl; $R^2$ is H or $(C_1\text{-}C_4)$alkyl, wherein the alkyl is optionally substituted with one to four $R^3$; each $R^3$ is independently at each occurrence —$NH_2$, —NHC(NH)$NH_2$, $(C_6\text{-}C_{10})$ aryl, or 5- to 10-membered monocyclic or bicyclic heteroaryl comprising 1-3 heteroatoms selected from N, O, and S, wherein the aryl and heteroaryl are optionally substituted with one to four $R^5$; and each $R^5$ is independently at each occurrence $(C_1\text{-}C_4)$alkyl, $(C_1\text{-}C_4)$haloalkyl, $(C_1\text{-}C_4)$alkoxy, $(C_1\text{-}C_4)$haloalkoxy, halogen, —$NH_2$, —OH or CN; or pharmaceutically acceptable salts, hydrates, solvates, prodrugs, stereoisomers, and tautomers thereof.

In an embodiment with respect to formulae (I) or (II), $R^1$ is H or $(C_1\text{-}C_4)$alkyl; $R^2$ is H or $(C_1\text{-}C_4)$alkyl, wherein the alkyl is optionally substituted with one to four $R^3$; each $R^3$ is independently at each occurrence —$NH_2$, —NHC(NH)$NH_2$, unsubstituted ($C_6$-$C_{10}$) aryl, or unsubstituted 5- to 10-membered monocyclic or bicyclic heteroaryl comprising 1-3 heteroatoms selected from N, O, and S, or pharmaceutically acceptable salts, hydrates, solvates, prodrugs, stereoisomers, and tautomers thereof.

In an embodiment with respect to formulae (I) or (II), $R^1$ is H or ($C_1$-$C_4$)alkyl; $R^2$ is H or ($C_1$-$C_4$)alkyl, wherein the alkyl is optionally substituted with one $R^3$; each $R^3$ is —$NH_2$, —NHC(NH)$NH_2$, phenyl, imidazole or indole, or pharmaceutically acceptable salts, hydrates, solvates, prodrugs, stereoisomers, and tautomers thereof.

In an embodiment with respect to formulae (I) or (II), $R^1$ is H. In another embodiment, $R^1$ is ($C_1$-$C_4$)alkyl. In another embodiment, $R^1$ is methyl, ethyl, n-propyl, i-propyl, n-butyl, i-butyl, or t-butyl. In yet another embodiment, $R^1$ is H, methyl, ethyl, n-propyl, i-propyl, n-butyl, i-butyl, or t-butyl. In another embodiment, $R^1$ is H, ethyl or t-butyl. In another embodiment, $R^1$ is H or t-butyl.

In an embodiment with respect to formulae (I) or (II), $R^2$ is ($C_1$-$C_4$)alkyl optionally substituted with one or more $R^3$. In another embodiment, $R^2$ is ($C_1$-$C_4$)alkyl optionally substituted with one to three $R^3$. In yet another embodiment, $R^2$ is ($C_6$-$C_{10}$) aryl or 5- or 6-membered heteroaryl comprising 1-3 heteroatoms selected from N, S, and O, wherein the aryl and heteroaryl are optionally substituted with one or more $R^4$. In another embodiment, $R^2$ is ($C_6$-$C_{10}$) aryl or 5- or 6-membered heteroaryl comprising 1-3 heteroatoms selected from N, S, and O, wherein the aryl and heteroaryl are optionally substituted with one to three $R^4$. In yet another embodiment, $R^2$ is ($C_1$-$C_4$)alkyl optionally substituted with one to two $R^3$. In another embodiment, $R^2$ is ($C_1$-$C_4$)alkyl optionally substituted with one $R^3$. In another embodiment, $R^2$ is ($C_1$-$C_4$)alkyl optionally substituted with —$NH_2$. In another embodiment, $R^2$ is ($C_1$-$C_4$)alkyl. In another embodiment, $R^2$ is ($C_1$-$C_4$)alkyl substituted with —$NH_2$. In another embodiment, $R^2$ is H. In another embodiment, $R^2$ is H or ($C_1$-$C_4$)alkyl optionally substituted with one $R^3$. In another embodiment, $R^2$ is H or ($C_1$-$C_4$)alkyl optionally substituted with —$NH_2$. In another embodiment, $R^2$ is H or ($C_1$-$C_4$)alkyl. In another embodiment, $R^2$ is H or ($C_1$-$C_4$)alkyl substituted with —$NH_2$.

In an embodiment with respect to formulae (I) or (II), each $R^3$ is independently at each occurrence —$NH_2$, ($C_1$-$C_4$)alkylamino, ($C_1$-$C_4$)dialkylamino, —OH, —SH, —S($C_1$-$C_4$)alkyl, —$CO_2H$, —$CONH_2$, or —NHC(NH)$NH_2$. In another embodiment, each $R^3$ is independently at each occurrence —$NH_2$, —OH, —SH, —S($C_1$-$C_3$)alkyl, —$CO_2H$, —$CONH_2$, —NHC(NH)$NH_2$, ($C_6$-$C_{10}$) aryl, or 5- to 10-membered monocyclic or bicyclic heteroaryl comprising 1-3 heteroatoms selected from N, O, and S, wherein the aryl and heteroaryl are optionally substituted with one to two $R^5$. In another embodiment, each $R^3$ is independently at each occurrence —$NH_2$, ($C_1$-$C_4$)alkylamino, or ($C_1$-$C_4$)dialkylamino.

In another embodiment, each $R^3$ is independently at each occurrence —$NH_2$, —OH, —SH, —S($C_1$-$C_3$)alkyl, —$CO_2H$, —$CONH_2$, —NHC(NH)$NH_2$, ($C_6$-$C_{10}$) aryl, or 5- or 10-membered monocyclic or bicyclic heteroaryl comprising 1-3 heteroatoms selected from N, O, and S, wherein the aryl and heteroaryl are optionally substituted with one to two $R^5$.

In another embodiment, each $R^3$ is independently at each occurrence ($C_6$-$C_{10}$) aryl or 5- or 6-membered heteroaryl comprising 1-3 heteroatoms selected from N, O, and S, wherein the aryl and heteroaryl are optionally substituted with one to two $R^5$. In yet another embodiment, each $R^3$ is independently at each occurrence —$NH_2$, ($C_6$-$C_{10}$) aryl, or 5- or 6-membered heteroaryl comprising 1-3 heteroatoms selected from N, O, and S, wherein the aryl and heteroaryl are optionally substituted with one to two $R^5$. In another embodiment, each $R^3$ is independently at each occurrence —$NH_2$ or ($C_6$-$C_{10}$) aryl optionally substituted with one to two $R^5$. In yet another embodiment, each $R^3$ is independently at each occurrence —$NH_2$.

In another embodiment, each $R^3$ is independently at each occurrence —$NH_2$, —NHC(NH)$NH_2$, ($C_6$-$C_{10}$) aryl, or 5- to 10-membered monocyclic or bicyclic heteroaryl comprising 1-3 heteroatoms selected from N, O, and S, wherein the aryl and heteroaryl are optionally substituted with one to four $R^5$; and each $R^5$ is independently at each occurrence ($C_1$-$C_4$)alkyl, ($C_1$-$C_4$)haloalkyl, ($C_1$-$C_4$)alkoxy, ($C_1$-$C_4$)haloalkoxy, halogen, —$NH_2$, —OH or CN; or pharmaceutically acceptable salts, hydrates, solvates, prodrugs, stereoisomers, and tautomers thereof. In an embodiment $R^3$ is —$NH_2$, —NHC(NH)$NH_2$, unsubstituted ($C_6$-$C_{10}$) aryl, or unsubstituted 5- to 10-membered monocyclic or bicyclic heteroaryl comprising 1-3 heteroatoms selected from N, O, and S. In an embodiment $R^3$ is —$NH_2$, —NHC(NH)$NH_2$, phenyl, imidazole or indole.

In an embodiment with respect to formulae (I) or (II), each $R^4$ is independently at each occurrence ($C_1$-$C_4$)alkyl, ($C_1$-$C_4$)haloalkyl, ($C_1$-$C_4$)alkoxy, or ($C_1$-$C_4$)haloalkoxy. In another embodiment, each $R^4$ is independently at each occurrence ($C_1$-$C_4$)alkyl, ($C_1$-$C_4$)haloalkyl, ($C_1$-$C_4$)alkoxy, ($C_1$-$C_4$)haloalkoxy, or halogen. In yet another embodiment, each $R^4$ is independently at each occurrence halogen, —$NH_2$, —OH or CN. In another embodiment, each $R^4$ is independently at each occurrence —$NH_2$, —OH or CN. In yet another embodiment, each $R^4$ is independently at each occurrence ($C_1$-$C_4$)alkyl, ($C_1$-$C_4$)haloalkyl, ($C_1$-$C_4$)alkoxy, ($C_1$-$C_4$)haloalkoxy, —$NH_2$, or —OH. In yet another embodiment, each $R^4$ is independently at each occurrence ($C_1$-$C_4$)alkyl, ($C_1$-$C_4$)alkoxy, —$NH_2$, or —OH. In another embodiment, each $R^4$ is independently at each occurrence —$NH_2$ or —OH. In another embodiment, each $R^4$ is independently at each occurrence —OH.

In an embodiment with respect to formulae (I) or (II), each $R^5$ is independently at each occurrence ($C_1$-$C_4$)alkyl, ($C_1$-$C_4$)haloalkyl, ($C_1$-$C_4$)alkoxy, or ($C_1$-$C_4$)haloalkoxy. In another embodiment, each $R^5$ is independently at each occurrence ($C_1$-$C_4$)alkyl, ($C_1$-$C_4$)haloalkyl, ($C_1$-$C_4$)alkoxy, ($C_1$-$C_4$)haloalkoxy, or halogen. In another embodiment, each $R^5$ is independently at each occurrence halogen, —$NH_2$, —OH or CN. In another embodiment, each $R^5$ is independently at each occurrence —$NH_2$, —OH or CN. In yet another embodiment, each $R^5$ is independently at each occurrence ($C_1$-$C_4$)alkyl, ($C_1$-$C_4$)haloalkyl, ($C_1$-$C_4$)alkoxy, ($C_1$-$C_4$)haloalkoxy, —$NH_2$, or —OH. In yet another embodiment, each $R^5$ is independently at each occurrence ($C_1$-$C_4$)alkyl, ($C_1$-$C_4$)alkoxy, —$NH_2$, or —OH. In another embodiment, each $R^5$ is independently at each occurrence —$NH_2$ or —OH. In another embodiment, each $R^5$ is independently at each occurrence —OH.

In an embodiment with respect to formulae (I) or (II), $R^1$ is H or ($C_1$-$C_4$)alkyl; $R^2$ is ($C_1$-$C_4$)alkyl, ($C_6$-$C_{10}$) aryl, 5- or 6-membered heteroaryl comprising 1-3 heteroatoms selected from N, S, and O, wherein the alkyl is optionally substituted with one or more $R^3$, and wherein the aryl and heteroaryl are optionally substituted with one or more $R^4$; each $R^3$ is independently at each occurrence —$NH_2$, ($C_1$-$C_4$)alkylamino, ($C_1$-$C_4$)dialkylamino, ($C_6$-$C_{10}$) aryl, or 5- or 6-membered heteroaryl comprising 1-3 heteroatoms selected from N, O, and S; and each $R^4$ is independently at each occurrence $(C_1-C_4)$alkyl, $(C_1-C_4)$haloalkyl, $(C_1-C_4)$alkoxy, $(C_1-C_4)$haloalkoxy, —$NH_2$, —OH or CN.

In an embodiment with respect to formulae (I) or (II), $R^1$ is H or $(C_1-C_4)$alkyl; $R^2$ is $(C_1-C_4)$alkyl, $(C_6-C_{10})$ aryl, 5- or 6-membered heteroaryl comprising 1-3 heteroatoms selected from N, S, and O, wherein the alkyl is optionally substituted with one to three $R^3$, and wherein the aryl and heteroaryl are optionally substituted with one to three $R^4$; each $R^3$ is independently at each occurrence —$NH_2$, $(C_1-C_4)$alkylamino, $(C_1-C_4)$dialkylamino, $(C_6-C_{10})$ aryl, or 5- or 6-membered heteroaryl comprising 1-3 heteroatoms selected from N, O, and S; and each $R^4$ is independently at each occurrence $(C_1-C_4)$alkyl, $(C_1-C_4)$haloalkyl, $(C_1-C_4)$alkoxy, $(C_1-C_4)$haloalkoxy, —$NH_2$, —OH or CN.

In an embodiment with respect to formulae (I) or (II), $R^1$ is H or $(C_1-C_4)$alkyl. In another embodiment, $R^1$ is H or $(C_1-C_4)$alkyl and $R^2$ is $(C_1-C_4)$alkyl optionally substituted with one to three $R^3$.

In an embodiment with respect to formulae (I) or (II), $R^1$ is H or t-butyl, and $R^2$ is $(C_4)$alkyl optionally substituted with —$NH_2$.

In another embodiment, individual compounds according to the disclosure are those listed in the Examples section below or a pharmaceutically acceptable salt thereof.

Various (enumerated) embodiments of the invention are described herein. It will be recognized that features specified in each embodiment may be combined with other specified features to provide further embodiments of the present invention.

Embodiment 1. A compound of the Formula (I):

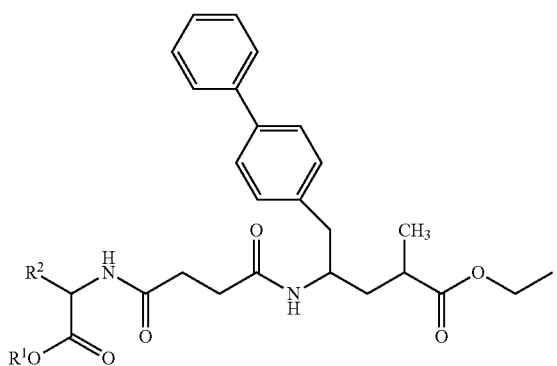

(I)

wherein:
$R^1$ is H or $(C_1-C_4)$alkyl;
$R^2$ is H, $(C_1-C_4)$alkyl, $(C_6-C_{10})$ aryl, or 5- or 6-membered heteroaryl comprising 1-3 heteroatoms selected from N, S, and O, wherein the alkyl is optionally substituted with one or more $R^3$, and wherein the aryl and heteroaryl are optionally substituted with one or more $R^4$;
each $R^3$ is independently at each occurrence —$NH_2$, $(C_1-C_4)$alkylamino, $(C_1-C_4)$dialkylamino, —OH, —SH, —S$(C_1-C_4)$alkyl, —$CO_2H$, —$CONH_2$, —$NHC(NH)NH_2$, $(C_6-C_{10})$ aryl, or 5- to 10-membered monocyclic or bicyclic heteroaryl comprising 1-3 heteroatoms selected from N, O, and S, wherein the aryl and heteroaryl are optionally substituted with one or more $R^5$;
each $R^4$ is independently at each occurrence $(C_1-C_4)$alkyl, $(C_1-C_4)$haloalkyl, $(C_1-C_4)$alkoxy, $(C_1-C_4)$haloalkoxy, halogen, —$NH_2$, —OH or CN; and each $R^5$ is independently at each occurrence $(C_1-C_4)$alkyl, $(C_1-C_4)$haloalkyl, $(C_1-C_4)$alkoxy, $(C_1-C_4)$haloalkoxy, halogen, —$NH_2$, —OH or CN;
or a pharmaceutically acceptable salt thereof.

Embodiment 2. The compound according to embodiment 1, having a Formula (II):

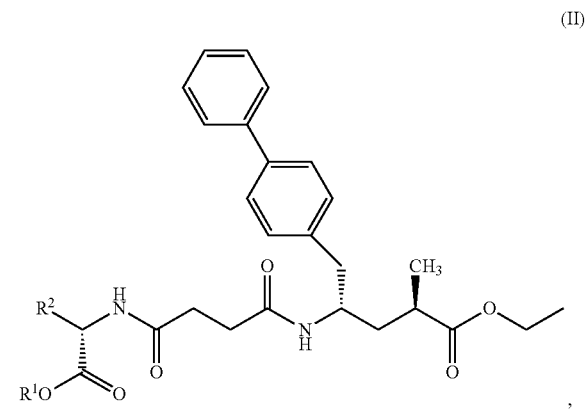

(II)

or a pharmaceutically acceptable salt thereof.

Embodiment 3. The compound, or a pharmaceutically acceptable salt thereof, according to embodiment 1 or 2, wherein $R^1$ is H, ethyl or t-butyl.

Embodiment 4. The compound, or a pharmaceutically acceptable salt thereof, according to any one of embodiments 1 to 3, wherein $R^1$ is H or t-butyl.

Embodiment 5. The compound, or a pharmaceutically acceptable salt thereof, according to any one of embodiments 1 to 4, wherein $R^1$ is H.

Embodiment 6. The compound, or a pharmaceutically acceptable salt thereof, according to any one of embodiments 1 to 5, wherein $R^2$ is H or $(C_1-C_4)$alkyl optionally substituted with one to two $R^3$.

Embodiment 7. The compound, or a pharmaceutically acceptable salt thereof, according to any one of embodiments 1 to 6, wherein $R^2$ is H or $(C_1-C_4)$alkyl optionally substituted with —$NH_2$.

Embodiment 8. The compound, or a pharmaceutically acceptable salt thereof, according to any one of embodiments 1 to 3, wherein $R^1$ is H, ethyl or t-butyl, and $R^2$ is H or $(C_4)$alkyl optionally substituted with —$NH_2$.

Embodiment 9. A compound selected from:
(4-(((2S,4R)-1-([1,1'-biphenyl]-4-yl)-5-ethoxy-4-methyl-5-oxopentan-2-yl)amino)-4-oxobutanoyl)-L-leucine;
(4-(((2S,4R)-1-([1,1'-biphenyl]-4-yl)-5-ethoxy-4-methyl-5-oxopentan-2-yl)amino)-4-oxobutanoyl)-L-lysine; and
tert-butyl (4-(((2S,4R)-1-([1,1'-biphenyl]-4-yl)-5-ethoxy-4-methyl-5-oxopentan-2-yl)amino)-4-oxobutanoyl)-L-lysinate;
ethyl (2R,4S)-5-([1,1'-biphenyl]-4-yl)-4-(4-(((S)-1-ethoxy-4-methyl-1-oxopentan-2-yl)amino)-4-oxobutanamido)-2-methylpentanoate;
(4-(((2S,4R)-1-([1,1'-biphenyl]-4-yl)-5-ethoxy-4-methyl-5-oxopentan-2-yl)amino)-4-oxobutanoyl)-L-arginine;
(4-(((2S,4R)-1-([1,1'-biphenyl]-4-yl)-5-ethoxy-4-methyl-5-oxopentan-2-yl)amino)-4-oxobutanoyl)-L-histidine;
(4-(((2S,4R)-1-([1,1'-biphenyl]-4-yl)-5-ethoxy-4-methyl-5-oxopentan-2-yl)amino)-4-oxobutanoyl)glycine;
(4-(((2S,4R)-1-([1,1'-biphenyl]-4-yl)-5-ethoxy-4-methyl-5-oxopentan-2-yl)amino)-4-oxobutanoyl)-L-alanine;

(4-(((2S,4R)-1-([1,1'-biphenyl]-4-yl)-5-ethoxy-4-methyl-5-oxopentan-2-yl)amino)-4-oxobutanoyl)-L-valine;

(4-(((2S, 4R)-1-([1,1'-biphenyl]-4-yl)-5-ethoxy-4-methyl-5-oxopentan-2-yl)amino)-4-oxobutanoyl)-L-phenylalanine;

(4-(((2S,4R)-1-([1,1'-biphenyl]-4-yl)-5-ethoxy-4-methyl-5-oxopentan-2-yl)amino)-4-oxobutanoyl)-L-tryptophan; and (4-(((2S,4R)-1-([1,1'-biphenyl]-4-yl)-5-ethoxy-4-methyl-5-oxopentan-2-yl)amino)-4-oxobutanoyl)-L-isoleucine;

or a pharmaceutically acceptable salt thereof.

Embodiment 10. The compound of embodiment 9 which is (4-(((2S,4R)-1-([1,1'-biphenyl]-4-yl)-5-ethoxy-4-methyl-5-oxopentan-2-yl)amino)-4-oxobutanoyl)-L-leucine or a pharmaceutically acceptable salt thereof.

Embodiment 11. The compound of embodiment 9 which is (4-(((2S,4R)-1-([1,1'-biphenyl]-4-yl)-5-ethoxy-4-methyl-5-oxopentan-2-yl)amino)-4-oxobutanoyl)-L-histidine or a pharmaceutically acceptable salt thereof.

In another embodiment, the disclosure relates to (4-(((2S, 4R)-1-([1,1'-biphenyl]-4-yl)-5-ethoxy-4-methyl-5-oxopentan-2-yl)amino)-4-oxobutanoyl)-L-leucine (compound I-1 of Example 1) in sodium salt form.

In another embodiment, the disclosure relates to a crystalline form A of compound I-1 of Example 1.

In yet another embodiment, the disclosure relates to a crystalline free acid form A of compound I-1 of Example 1 characterized by a x-ray powder diffraction pattern comprising three or more theta (2θ) peaks selected from the group consisting of 7.1±0.1°, 7.8±0.1°, 8.7±0.1°, 10.7±0.1°, 13.0±0.1°, 15.6±0.1°, 16.0±0.1°, 16.3±0.1°, 17.0±0.1°, 17.3±0.1°, 17.7±0.1°, 18.7±0.1°, 19.2±0.1°, 19.5±0.1°, 20.2±0.1°, 20.9±0.1°, 21.4±0.1°, 21.6±0.1°, 22.4±0.1°, 22.6±0.1°, 22.8±0.1°, 23.4±0.1°, 23.8±0.1°, 24.3±0.1°, 24.9±0.10, 25.7±0.1°, 26.2±0.1°, 27.2±0.1°, 27.3±0.1°, 27.5±0.1°, 28.5±0.1°, 28.8±0.1°, 29.3±0.1°, 29.8±0.1°, 31.6±0.1°, 32.2±0.1°, 34.1±0.1°, 36.1±0.1°, 36.2±0.1°, 36.9±0.1°, 41.1±0.1°, and 43.8±0.10 measured at a temperature of about 22° C. and an x-ray wavelength, λ, of 1.5418 Å.

In another embodiment, the disclosure relates to a crystalline free acid form A of compound I-1 of Example 1 characterized by a x-ray powder diffraction pattern comprising four or more 2θpeaks selected from the group consisting of 7.1±0.1°, 7.8±0.1°, 8.7±0.1°, 10.7±0.1°, 13.0±0.1°, 15.6±0.1°, 16.0±0.1°, 16.3±0.1°, 17.0±0.1°, 17.3±0.1°, 17.7±0.1°, 18.7±0.1°, 19.2±0.1°, 19.5±0.1°, 20.2±0.1°, 20.9±0.1°, 21.4±0.1°, 21.6±0.1°, 22.4±0.1°, 22.6±0.1°, 22.8±0.1°, 23.4±0.1°, 23.8±0.1°, 24.3±0.1°, 24.9±0.1°, 25.7±0.1°, 26.2±0.1°, 27.2±0.1°, 27.3±0.1°, 27.5±0.1°, 28.5±0.1°, 28.8±0.1°, 29.3±0.1°, 29.8±0.1°, 31.6±0.1°, 32.2±0.1°, 34.1±0.1°, 36.1±0.1°, 36.2±0.1°, 36.9±0.1°, 41.1±0.10, and 43.8±0.1° measured at a temperature of about 22° C. and an x-ray wavelength, λ, of 1.5418 Å.

In yet another embodiment, the disclosure relates to a crystalline free acid form A of compound I-1 of Example 1 characterized by a x-ray powder diffraction pattern comprising five or more 2θpeaks selected from the group consisting of 7.1±0.1°, 7.8±0.1°, 8.7±0.1°, 10.7±0.1°, 13.0±0.1°, 15.6±0.1°, 16.0±0.1°, 16.3±0.1°, 17.0±0.1°, 17.3±0.1°, 17.7±0.1°, 18.7±0.1°, 19.2±0.1°, 19.5±0.1°, 20.2±0.1°, 20.9±0.1°, 21.4±0.1°, 21.6±0.1°, 22.4±0.1°, 22.6±0.1°, 22.8±0.1°, 23.4±0.1°, 23.8±0.1°, 24.3±0.1°, 24.9±0.1°, 25.7±0.1°, 26.2±0.1°, 27.2±0.1°, 27.3±0.1°, 27.5±0.1°, 28.5±0.1°, 28.8±0.1°, 29.3±0.1°, 29.8±0.1°, 31.6±0.1°, 32.2±0.1°, 34.1±0.1°, 36.1±0.1°, 36.2±0.1°, 36.9±0.1°, 41.1±0.10, and 43.8±0.1 measured at a temperature of about 22° C. and an x-ray wavelength, λ, of 1.5418 Å.

In another embodiment, the disclosure relates to a crystalline free acid form A of compound I-1 of Example 1 characterized by a x-ray powder diffraction pattern comprising 2-theta peaks at 13.0±0.1°, 17.3±0.1°, 18.7±0.1°, 19.2±0.1°, and 20.2±0.1°. In yet another embodiment, the crystalline free acid form A of compound I-1 of Example 1 further comprises a 2-theta peak at 19.2±0.1 measured at a temperature of about 22° C. and an x-ray wavelength, λ, of 1.5418 Å. In another embodiment, the crystalline free acid form A of compound I-1 of Example 1 further comprises a 2-theta peak at 8.7±0.1°. In yet another embodiment, the crystalline free acid form A of compound I-1 of Example 1 further comprises a 2-theta peak at 19.2±0.10 and 8.7±0.1°.

In another embodiment, the disclosure relates to a crystalline free acid form A of compound I-1 of Example 1 having an X-ray diffraction spectrum substantially the same as the X-ray powder diffraction spectrum shown in FIG. 1.

Figure 2:
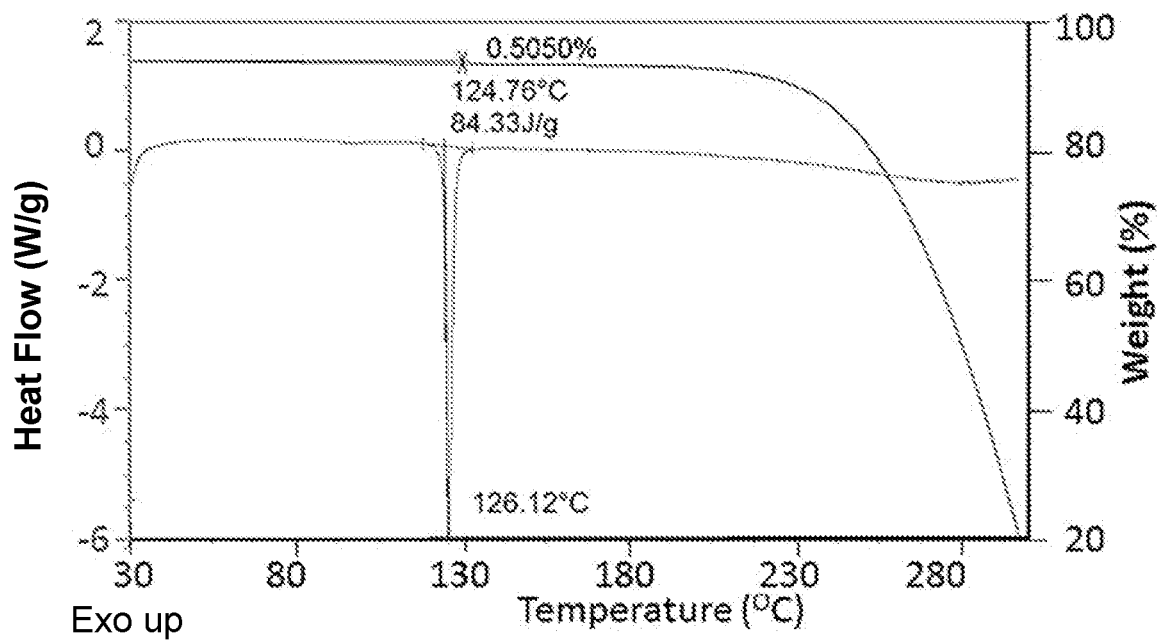
FIG. 2 illustrates the differential scanning calorimetry (DSC) and thermogravimetric analysis (TGA) of a Crystalline Form A of compound I-1 in Example 1.

In yet another embodiment, the disclosure relates to a crystalline free acid form A of compound I-1 of Example 1 having a differential scanning calorimetry (DSC) thermogram/thermo gravimetric analysis (TGA) diagram substantially the same as that shown in shown in FIG. 2.

In yet another embodiment, the disclosure relates to a crystalline free acid form A of compound I-1 of Example 1 having a differential scanning calorimetry (DSC) thermogram substantially the same as that shown in shown in FIG. 2.

In yet another embodiment, the disclosure relates to a crystalline free acid form A of compound I-1 of Example 1 having a thermo gravimetric analysis (TGA) diagram substantially the same as that shown in shown in FIG. 2.

In another embodiment, the disclosure relates to a crystalline form A of compound I-2 of Example 3.

In yet another embodiment, the disclosure relates to a crystalline free acid form A of compound I-2 of Example 3 characterized by a x-ray powder diffraction pattern comprising three or more 2θpeaks selected from the group consisting of 10.6±0.1°, 10.8±0.1°, 11.1±0.1°, 12.1±0.1°, 12.2±0.1°, 13.4±0.1°, 13.6±0.1°, 15.1±0.1°, 16.0±0.1°, 16.1±0.1°, 16.7±0.1°, 16.7±0.1°, 17.1±0.1°, 19.2±0.1°, 19.9±0.1°, 20.7±0.1°, 20.8±0.1°, 21.2±0.1°, 21.3±0.1°, 21.6±0.1°, 21.9±0.1°, 22.1±0.1°, 22.5±0.1°, 23.2±0.1°, 23.3±0.1°, 24.0±0.1°, 24.3±0.1°, 25.0±0.1°, 26.9±0.1°, 27.1±0.1°, 27.5±0.1°, 28.8±0.1°, and 29.1±0.1° measured at a temperature of about 22° C. and an x-ray wavelength, λ, of 1.5418 Å.

In another embodiment, the disclosure relates to a crystalline free acid form A of compound I-2 of Example 3 characterized by a x-ray powder diffraction pattern comprising four or more 2θpeaks selected from the group consisting of 10.6±0.1°, 10.8±0.1°, 11.1±0.1°, 12.1±0.1°, 12.2±0.1°, 13.4±0.1°, 13.6±0.1°, 15.1±0.1°, 16.0±0.1°, 16.1±0.1°, 16.7±0.1°, 16.7±0.1°, 17.1±0.1°, 19.2±0.1°, 19.9±0.1°, 20.7±0.1°, 20.8±0.1°, 21.2±0.1°, 21.3±0.1°, 21.6±0.1°, 21.9±0.1°, 22.1±0.1°, 22.5±0.1°, 23.2±0.1°, 23.3±0.1°, 24.0±0.1°, 24.3±0.1°, 25.0±0.1°, 26.9±0.1°, 27.1±0.1°, 27.5±0.1°, 28.8±0.1°, and 29.1±0.1° measured at a temperature of about 22° C. and an x-ray wavelength, λ, of 1.5418 Å.

In another embodiment, the disclosure relates to a crystalline free acid form A of compound I-2 of Example 3 characterized by a x-ray powder diffraction pattern comprising five or more 2θpeaks selected from the group consisting of 10.6±0.1°, 10.8±0.1°, 11.1±0.1°, 12.1±0.1°, 12.2±0.1°, 13.4±0.1°, 13.6±0.1°, 15.1±0.1°, 16.0±0.1°, 16.1±0.1°, 16.7±0.1°, 16.7±0.1°, 17.1±0.1°, 19.2±0.1°, 19.9±0.1°, 20.7±0.1°, 20.8±0.1°, 21.2±0.1°, 21.3±0.1°, 21.6±0.1°, 21.9±0.1°, 22.1±0.1°, 22.5±0.1°, 23.2±0.1°, 23.3±0.1°, 24.0±0.1°, 24.3±0.1°, 25.0±0.1°, 26.9±0.1°, 27.1±0.1°, 27.5±0.1°, 28.8±0.1°, and 29.1±0.1° measured at a temperature of about 22° C. and an x-ray wavelength, λ, of 1.5418 Å.

In yet another embodiment, the disclosure relates to a crystalline free acid form A of compound I-2 of Example 3 characterized by a x-ray powder diffraction pattern comprising 2-theta peaks (2θ) at 12.1±0.1°, 16.0±0.1°, 16.1±0.1°, 19.2±0.1°, and 22.5±0.1°. In another embodiment, the crystalline free acid form A of Compound I-2 of Example 3 further comprises a 2-theta peak at 13.4±0.1°. In yet another embodiment, the crystalline free acid form A of compound I-2 of Example 3 further comprises a 2-theta peak at 19.9±0.1°. In another embodiment, the crystalline free acid form A of Compound I-2 of Example 3 further comprises a 2-theta peak at 13.4±0.1° and 19.9±0.1°.

Figure 3:
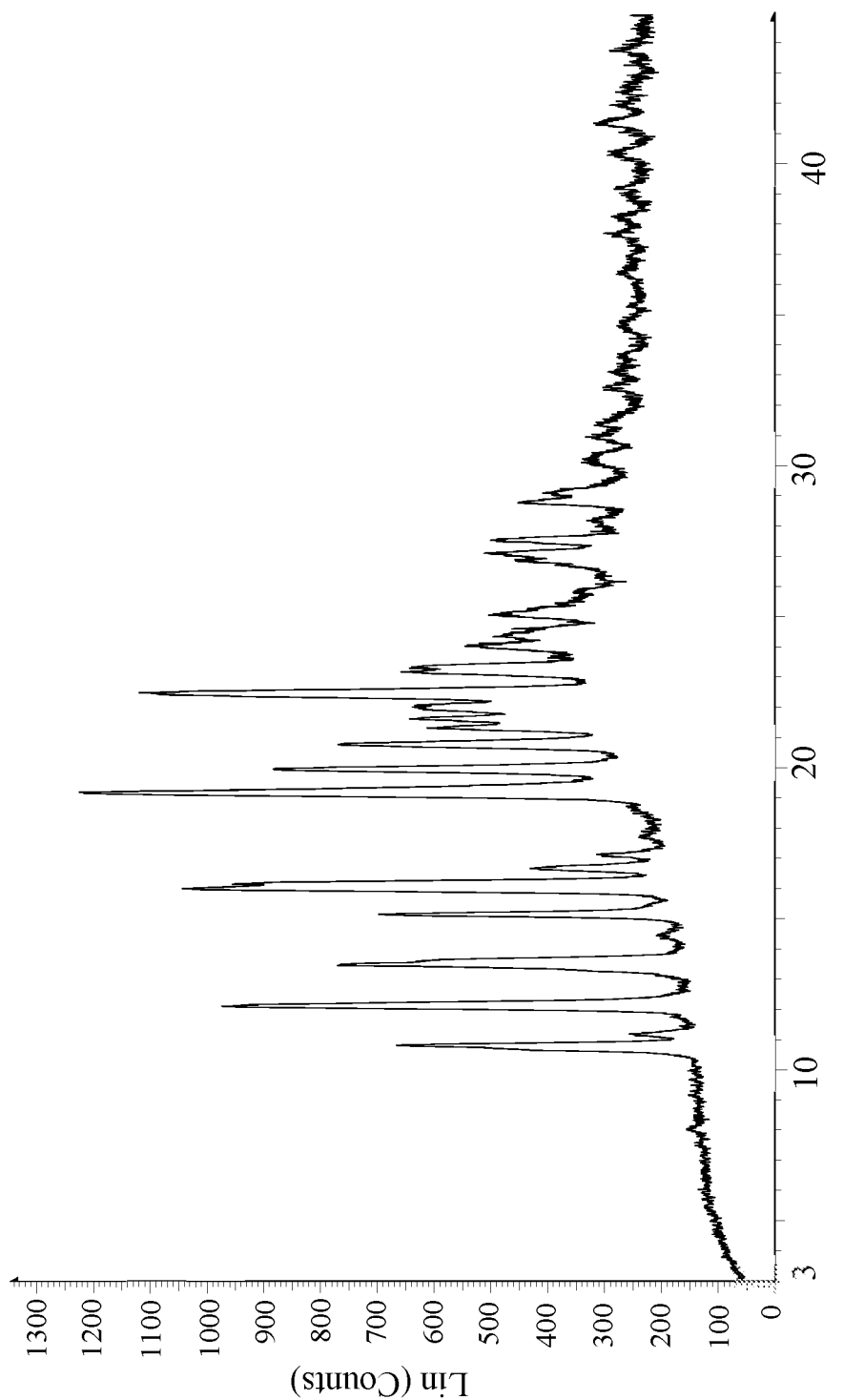
FIG. 3 illustrates the x-ray powder diffraction patterns of the crystalline form A of compound I-2 in Example 3.

In another embodiment, the disclosure relates to a crystalline free acid form A of compound I-2 of Example 3 having an X-ray diffraction spectrum substantially the same as the X-ray powder diffraction spectrum shown in FIG. 3.

Figure 4:
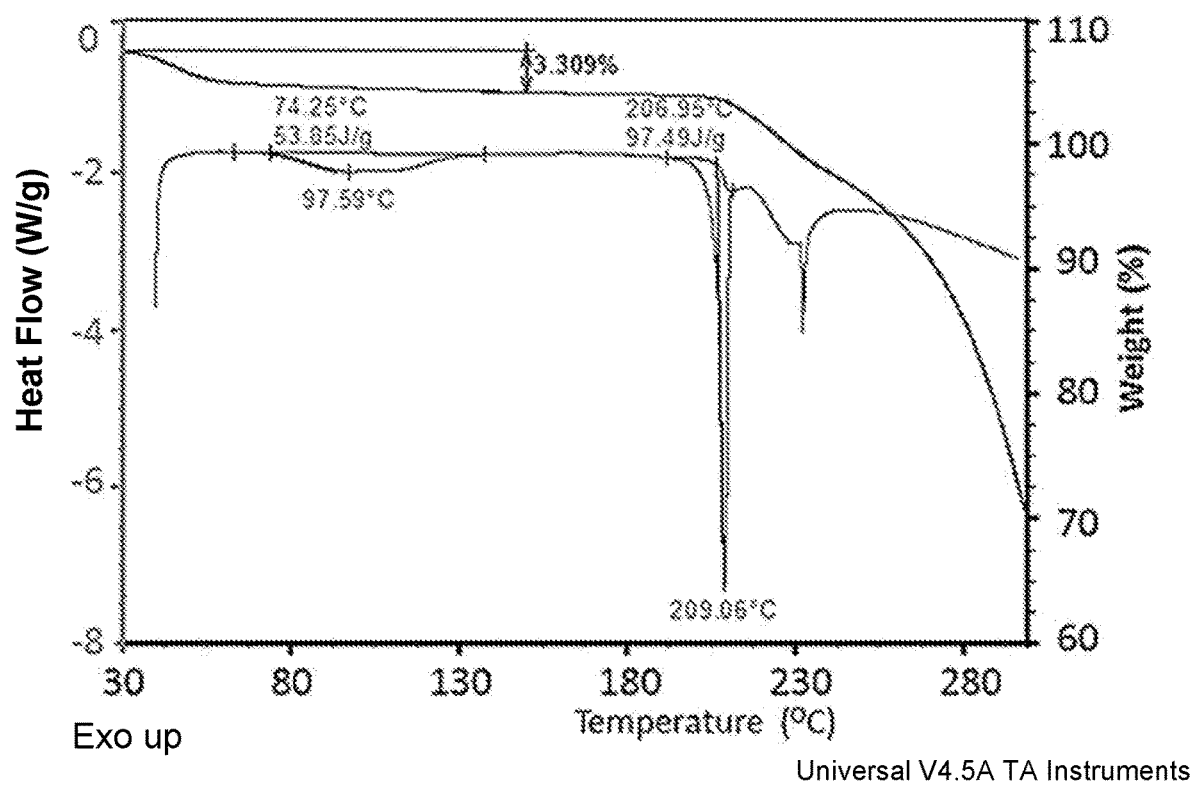
FIG. 4 illustrates the differential scanning calorimetry (DSC) and thermogravimetric analysis (TGA) of a Crystalline Form A of compound I-2 in Example 3.

In yet another embodiment, the disclosure relates to a crystalline free acid form A of compound I-2 of Example 3 having a differential scanning calorimetry (DSC) thermogram/thermo gravimetric analysis (TGA) diagram substantially the same as that shown in shown in FIG. 4.

In another embodiment, the disclosure relates to a crystalline free acid form A of compound I-2 of Example 3 having a differential scanning calorimetry (DSC) thermogram substantially the same as that shown in shown in FIG. 4.

In yet another embodiment, the disclosure relates to a crystalline free acid form A of compound I-2 of Example 3 having a thermo gravimetric analysis (TGA) diagram substantially the same as that shown in shown in FIG. 4.

In another embodiment, the disclosure relates to a crystalline form B of compound I-2 of Example 3.

In yet another embodiment, the disclosure relates to a crystalline free acid form B of compound I-2 of Example 3 characterized by a x-ray powder diffraction pattern comprising three or more 2θpeaks selected from the group consisting of 8.7±0.1°, 9.3±0.1°, 12.4±0.1°, 13.5±0.1°, 14.8±0.1°, 15.5±0.1°, 16.2±0.1°, 16.6±0.1°, 16.9±0.1°, 17.5±0.1°, 18.0±0.1°, 18.6±0.1°, 18.9±0.1°, 20.5±0.1°, 21.8±0.1°, 23.3±0.1°, 23.7±0.1°, 24.8±0.10, 25.0±0.1°, 25.7±0.1°, 26.3±0.1°, 28.1±0.1°, 28.6±0.1°, 32.3±0.1°, 32.9±0.1°, 37.3±0.1°, 38.7±0.1°, and 39.9±0.1°.

In another embodiment, the disclosure relates to a crystalline free acid form B of compound I-2 of Example 3 characterized by a x-ray powder diffraction pattern comprising four or more 2θpeaks selected from the group consisting of 8.7±0.1°, 9.3±0.1°, 12.4±0.1°, 13.5±0.1°, 14.8±0.1°, 15.5±0.1°, 16.2±0.1°, 16.6±0.1°, 16.9±0.1°, 17.5±0.1°, 18.0±0.1°, 18.6±0.1°, 18.9±0.1°, 20.5±0.1°, 21.8±0.1°, 23.3±0.1°, 23.7±0.1°, 24.8±0.10, 25.0±0.1°, 25.7±0.1°, 26.3±0.1°, 28.1±0.1°, 28.6±0.1°, 32.3±0.1°, 32.9±0.1°, 37.3±0.1°, 38.7±0.1°, and 39.9±0.1°.

In yet another embodiment, the disclosure relates to a crystalline free acid form B of compound I-2 of Example 3 characterized by a x-ray powder diffraction pattern comprising five or more 2θpeaks selected from the group consisting of 8.7±0.1°, 9.3±0.1°, 12.4±0.1°, 13.5±0.1°, 14.8±0.1°, 15.5±0.1°, 16.2±0.1°, 16.6±0.1°, 16.9±0.1°, 17.5±0.1°, 18.0±0.1°, 18.6±0.1°, 18.9±0.1°, 20.5±0.1°, 21.8±0.1°, 23.3±0.1°, 23.7±0.1°, 24.8±0.1°, 25.0±0.1°, 25.7±0.1°, 26.3±0.1°, 28.1±0.1°, 28.6±0.1°, 32.3±0.1°, 32.9±0.1°, 37.3±0.10, 38.7±0.1°, and 39.9±0.1°.

In yet another embodiment, the disclosure relates to a crystalline free acid form B of compound I-2 of Example 3 characterized by a x-ray powder diffraction pattern comprising 2-theta peaks (2θ) at 9.3±0.1°, 13.5±0.1°, 16.1±0.1°, 17.5±0.1°, and 25.0±0.1°. In another embodiment, the crystalline free acid form B of compound I-2 of Example 3 further comprises a 2-theta peak at 21.8±0.1°. In yet another embodiment, the crystalline free acid form B of compound I-2 of Example 3 further comprises a 2-theta peak at 24.8±0.1°. In another embodiment, the crystalline free acid form B of compound I-2 of Example 3 further comprises a 2-theta peak at 21.8±0.1° and 24.8±0.1°.

Figure 5:
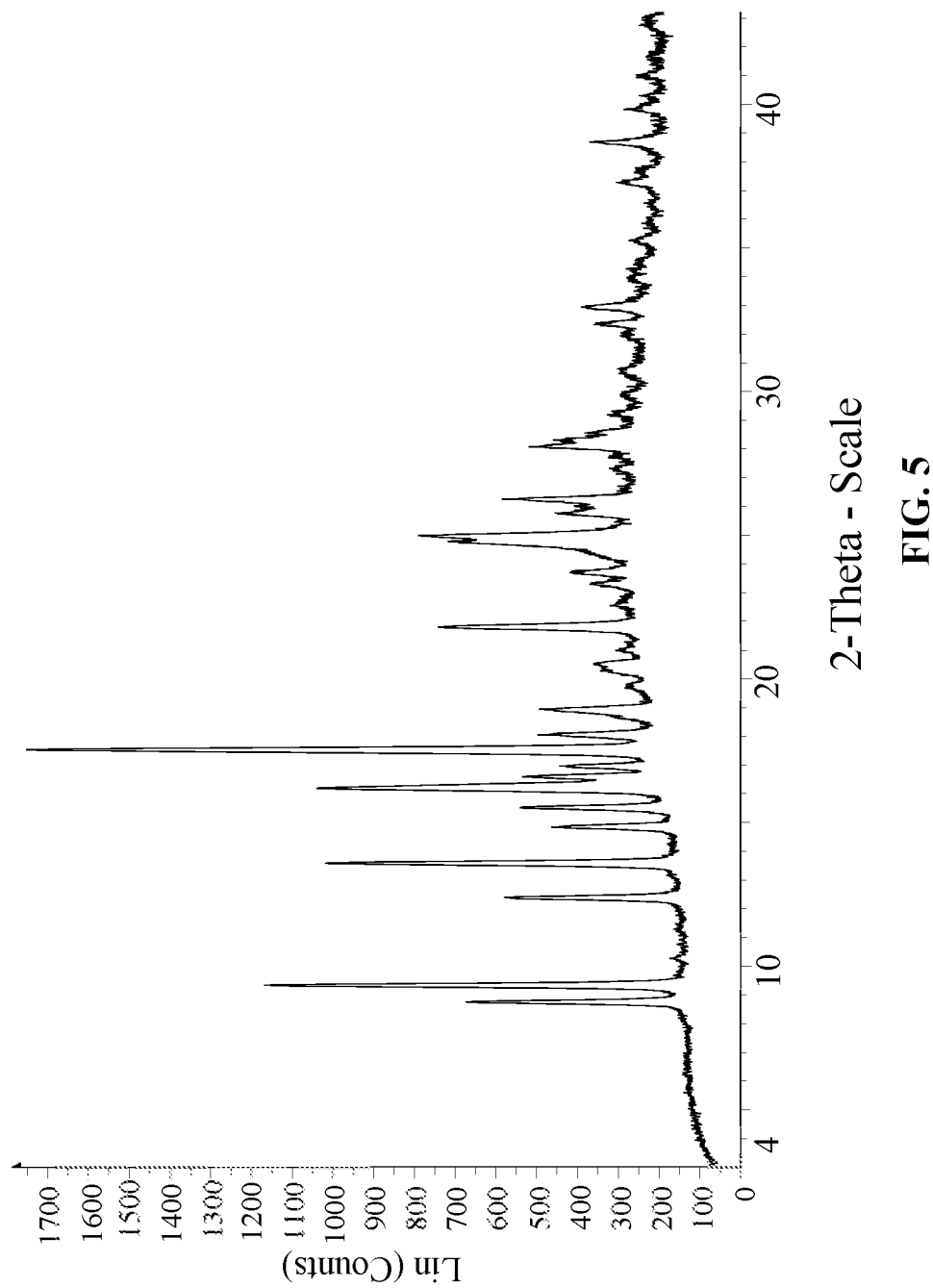
FIG. 5 illustrates the x-ray powder diffraction patterns of a Crystalline Form B of compound I-2 in Example 3.

In another embodiment, the disclosure relates to a crystalline free acid form B of compound I-2 of Example 3 having an X-ray diffraction spectrum substantially the same as the X-ray powder diffraction spectrum shown in FIG. 5.

Figure 6:
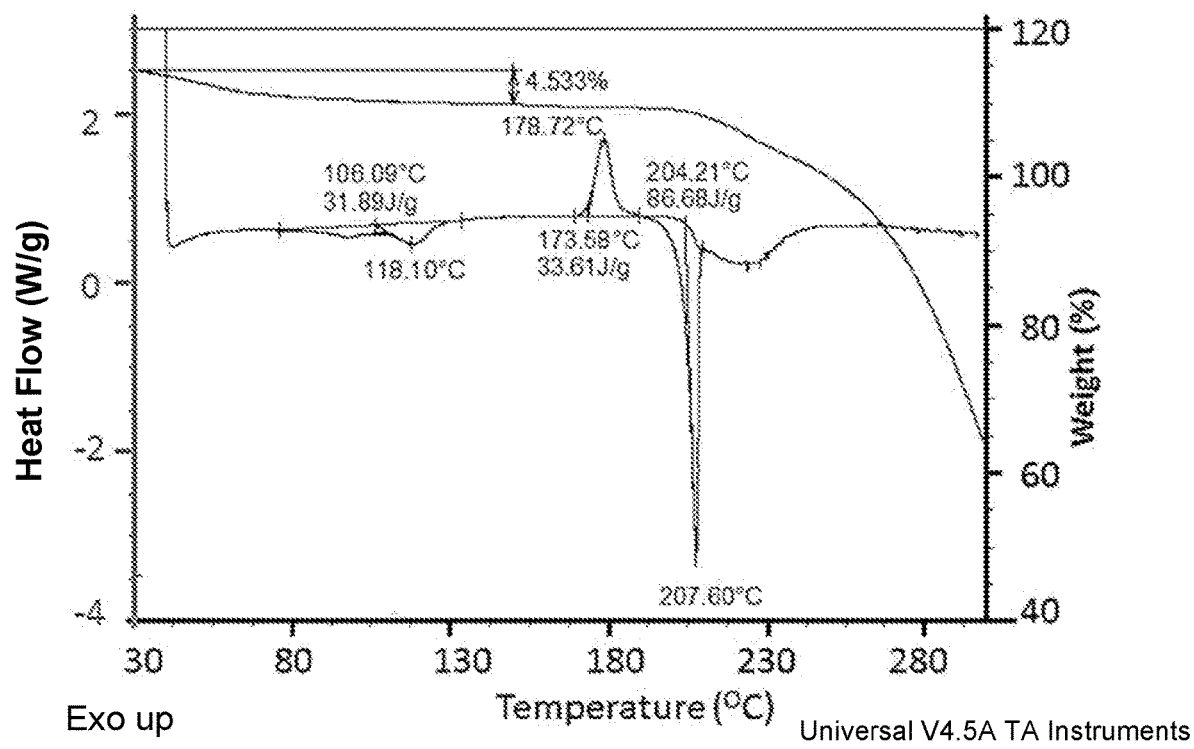
FIG. 6 illustrates the differential scanning calorimetry (DSC) and thermogravimetric analysis (TGA) of a Crystalline Form B of compound I-2 in Example 3.

In yet another embodiment, the disclosure relates to a crystalline free acid form B of compound I-2 of Example 3 having a differential scanning calorimetry (DSC) thermogram/thermo gravimetric analysis (TGA) diagram substantially the same as that shown in shown in FIG. 6.

In another embodiment, the disclosure relates to a crystalline free acid form B of compound I-2 of Example 3 having a differential scanning calorimetry (DSC) thermogram substantially the same as that shown in shown in FIG. 6.

In yet another embodiment, the disclosure relates to a crystalline free acid form B of compound I-2 of Example 3 having a thermo gravimetric analysis (TGA) diagram substantially the same as that shown in shown in FIG. 6.

In another embodiment, the disclosure relates to compound I-3 of Example 2 in succinate salt form, malonate salt form or fumarate salt form.

In another embodiment, the disclosure relates to a crystalline form of a succinate salt of compound I-3 of Example 2.

In yet another embodiment, the disclosure relates to a crystalline form of a succinate salt of compound I-3 of Example 2 characterized by a x-ray powder diffraction pattern comprising three or more 2θpeaks selected from the group consisting of 8.5±0.1°, 11.2±0.1°, 12.7±0.1°, 13.4±0.1°, 14.8±0.1°, 16.1±0.1°, 16.9±0.1°, 18.1±0.1°, 19.2±0.1°, 19.6±0.1°, 20.1±0.1°, 20.8±0.1°, 20.9±0.1°, 21.8±0.1°, 22.5±0.1°, 23.6±0.1°, 24.4±0.1°, 25.6±0.1°, 26.4±0.1°, 26.7±0.1°, 27.6±0.1°, 28.5±0.1°, 31.6±0.1°, and 32.4±0.1°.

In another embodiment, the disclosure relates to a crystalline form of a succinate salt of compound I-3 of Example 2 characterized by a x-ray powder diffraction pattern comprising four or more 2θpeaks selected from the group consisting of 8.5±0.1°, 11.2±0.1°, 12.7±0.1°, 13.4±0.1°, 14.8±0.1°, 16.1±0.1°, 16.9±0.1°, 18.1±0.1°, 19.2±0.1°, 19.6±0.1°, 20.1±0.1°, 20.8±0.1°, 20.9±0.1°, 21.8±0.1°, 22.5±0.1°, 23.6±0.1°, 24.4±0.1°, 25.6±0.10, 26.4±0.1°, 26.7±0.1°, 27.6±0.1°, 28.5±0.1°, 31.6±0.1°, and 32.4±0.1°.

In yet another embodiment, the disclosure relates to a crystalline form of a succinate salt of compound I-3 of Example 2 characterized by a x-ray powder diffraction pattern comprising five or more 2θpeaks selected from the group consisting of 8.5±0.1°, 11.2±0.1°, 12.7±0.1°, 13.4±0.1°, 14.8±0.1°, 16.1±0.1°, 16.9±0.1°, 18.1±0.1°, 19.2±0.1°, 19.6±0.1°, 20.1±0.1°, 20.8±0.1°, 20.9±0.1°, 21.8±0.1°, 22.5±0.1°, 23.6±0.1°, 24.4±0.1°, 25.6±0.1°, 26.4±0.1°, 26.7±0.1°, 27.6±0.1°, 28.5±0.1°, 31.6±0.1°, and 32.4±0.1°.

In yet another embodiment, the disclosure relates to a crystalline form of a succinate salt of compound I-3 of Example 2 characterized by a x-ray powder diffraction pattern comprising 2-theta peaks (2θ) at 12.7±0.1°, 19.6±0.1°, 20.8±0.1°, 20.9±0.1°, and 21.8±0.1°. In another embodiment, the crystalline form of a succinate salt of compound I-3 of Example 2 further comprises a 2-theta peak at 11.2±0.1°. In yet another embodiment, the crystalline form of a succinate salt of compound I-3 of Example 2 further comprises a 2-theta peak at 19.2±0.1°. In another embodiment, the crystalline form of a succinate salt of compound I-3 of Example 2 further comprises a 2-theta peak at 11.2±0.1° and 19.2±0.1°.

Figure 7:
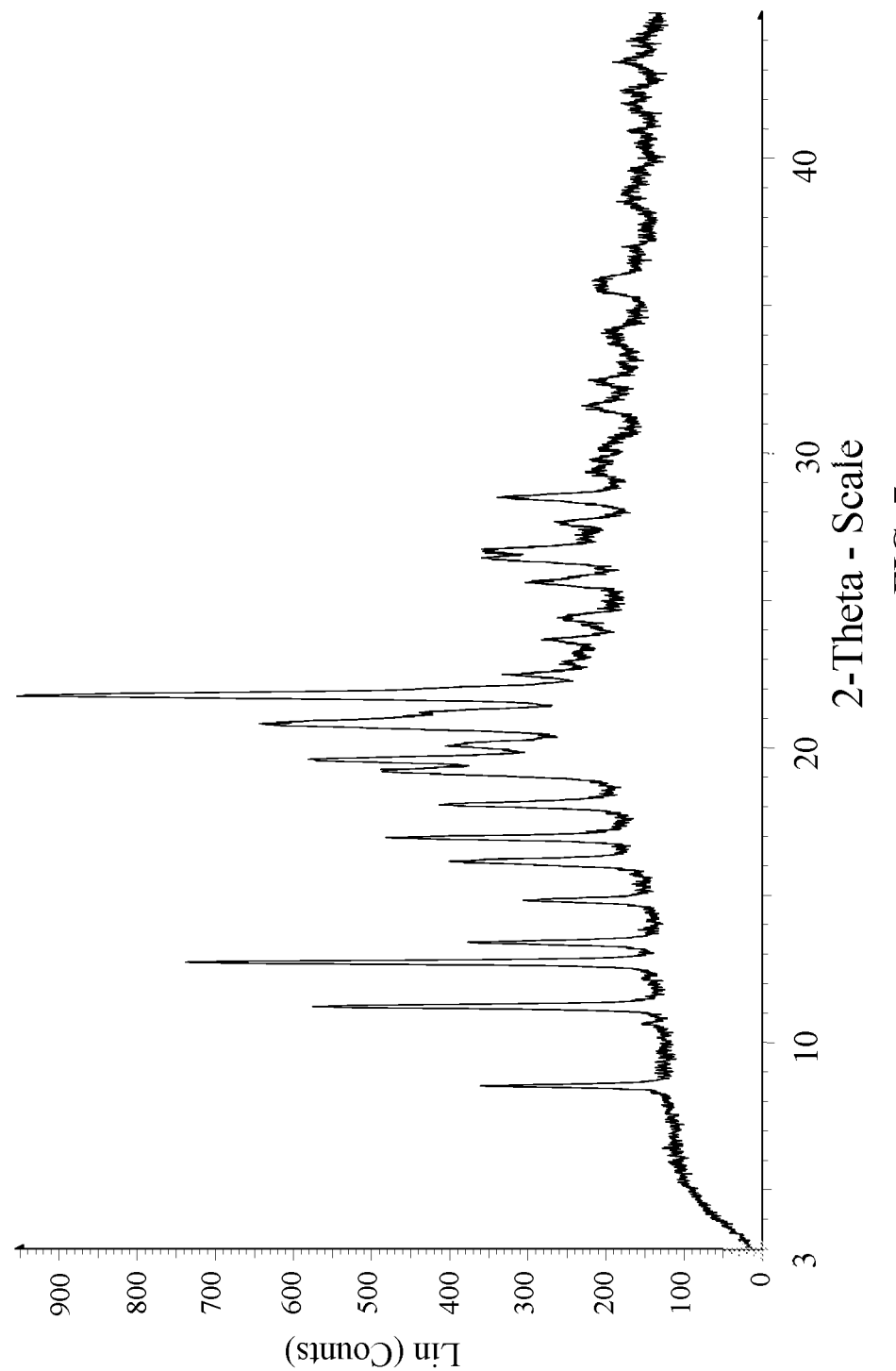
FIG. 7 illustrates the x-ray powder diffraction patterns of a Crystalline Form of a succinate salt of compound I-3 in Example 2.

In another embodiment, the disclosure relates to a crystalline form of a succinate salt of compound I-3 of Example 2 having an X-ray diffraction spectrum substantially the same as the X-ray powder diffraction spectrum shown in FIG. 7.

Figure 8:
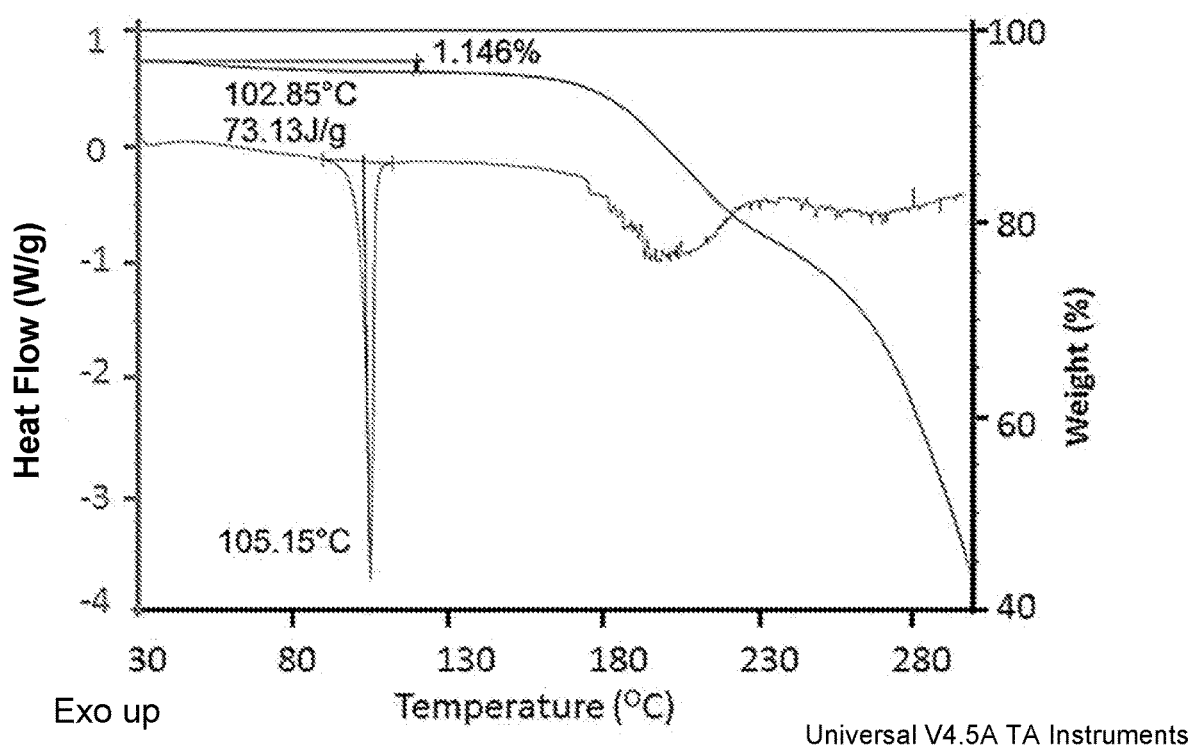
FIG. 8 illustrates the differential scanning calorimetry (DSC) and thermogravimetric analysis (TGA) of a Crystalline Form A of a succinate salt of compound I-3 in Example 2.

In yet another embodiment, the disclosure relates to a crystalline form of a succinate salt of compound I-3 of Example 2 having a differential scanning calorimetry (DSC) thermogram/thermo gravimetric analysis (TGA) diagram substantially the same as that shown in shown in FIG. 8.

In another embodiment, the disclosure relates to a crystalline form of a succinate salt of compound I-3 of Example 2 having a differential scanning calorimetry (DSC) thermogram substantially the same as that shown in shown in FIG. 8.

In yet another embodiment, the disclosure relates to a crystalline form of a succinate salt of compound I-3 of Example 2 having a thermo gravimetric analysis (TGA) diagram substantially the same as that shown in shown in FIG. 8.

In another embodiment, the disclosure relates to a crystalline form of a malonate salt of compound I-3 of Example 2.

In yet another embodiment, the disclosure relates to a crystalline form of a malonate salt of compound I-3 of Example 2 characterized by a x-ray powder diffraction pattern comprising three or more 2θpeaks selected from the group consisting of 8.7±0.1°, 10.8±0.1°, 11.5±0.1°, 13.1±0.1°, 13.7±0.1°, 15.2±0.1°, 15.7±0.1°, 15.8±0.1°, 17.4±0.1°, 18.4±0.1°, 19.1±0.1°, 19.4±0.1°, 19.4±0.1°, 19.7±0.1°, 20.4±0.1°, 21.3±0.1°, 21.7±0.10, 22.3±0.1°, 23.0±0.1°, 24.1±0.1°, 24.7±0.1°, 26.6±0.1°, 26.8±0.1°, 27.5±0.1°, 28.5±0.1°, 28.6±0.1°, 32.4±0.1°, and 33.3±0.1°.

In another embodiment, the disclosure relates to a crystalline form of a malonate salt of compound I-3 of Example 2 characterized by a x-ray powder diffraction pattern comprising four or more 2θpeaks selected from the group consisting of 8.7±0.1°, 10.8±0.1°, 11.5±0.1°, 13.1±0.1°, 13.7±0.1°, 15.2±0.1°, 15.7±0.1°, 15.8±0.1°, 17.4±0.1°, 18.4±0.1°, 19.1±0.1°, 19.4±0.1°, 19.4±0.1°, 19.7±0.1°, 20.4±0.1°, 21.3±0.1°, 21.7±0.1°, 22.3±0.1°, 23.0±0.1°, 24.1±0.1°, 24.7±0.1°, 26.6±0.1°, 26.8±0.1°, 27.5±0.1°, 28.5±0.1°, 28.6±0.1°, 32.4±0.1°, and 33.3±0.1°.

In yet another embodiment, the disclosure relates to a crystalline form of a malonate salt of compound I-3 of Example 2 characterized by a x-ray powder diffraction pattern comprising five or more 2θpeaks selected from the group consisting of 8.7±0.1°, 10.8±0.1°, 11.5±0.1°, 13.1±0.1°, 13.7±0.1°, 15.2±0.1°, 15.7±0.1°, 15.8±0.1°, 17.4±0.1°, 18.4±0.1°, 19.1±0.1°, 19.4±0.1°, 19.4±0.1°, 19.7±0.1°, 20.4±0.1°, 21.3±0.1°, 21.7±0.1°, 22.3±0.1°, 23.0±0.1°, 24.1±0.1°, 24.7±0.1°, 26.6±0.1°, 26.8±0.1°, 27.5±0.1°, 28.5±0.1°, 28.6±0.1°, 32.4±0.1°, and 33.3±0.1°.

In yet another embodiment, the disclosure relates to a crystalline form of a malonate salt of compound I-3 of Example 2 characterized by a x-ray powder diffraction pattern comprising 2-theta peaks (2θ) at 11.5±0.1°, 19.4±0.1°, 20.4±0.1°, 21.3±0.1°, and 21.7±0.1°. In another embodiment, the crystalline form of a malonate salt of compound I-3 of Example 2 further comprises a 2-theta peak at 19.1±0.1. In yet another embodiment, the crystalline form of a malonate salt of compound I-3 of Example 2 further comprises a 2-theta peak at 19.4±0.1°. In another embodiment, the crystalline form of a malonate salt of compound I-3 of Example 2 further comprises a 2-theta peak at 19.1±0.1° and 19.4±0.1°.

Figure 9:
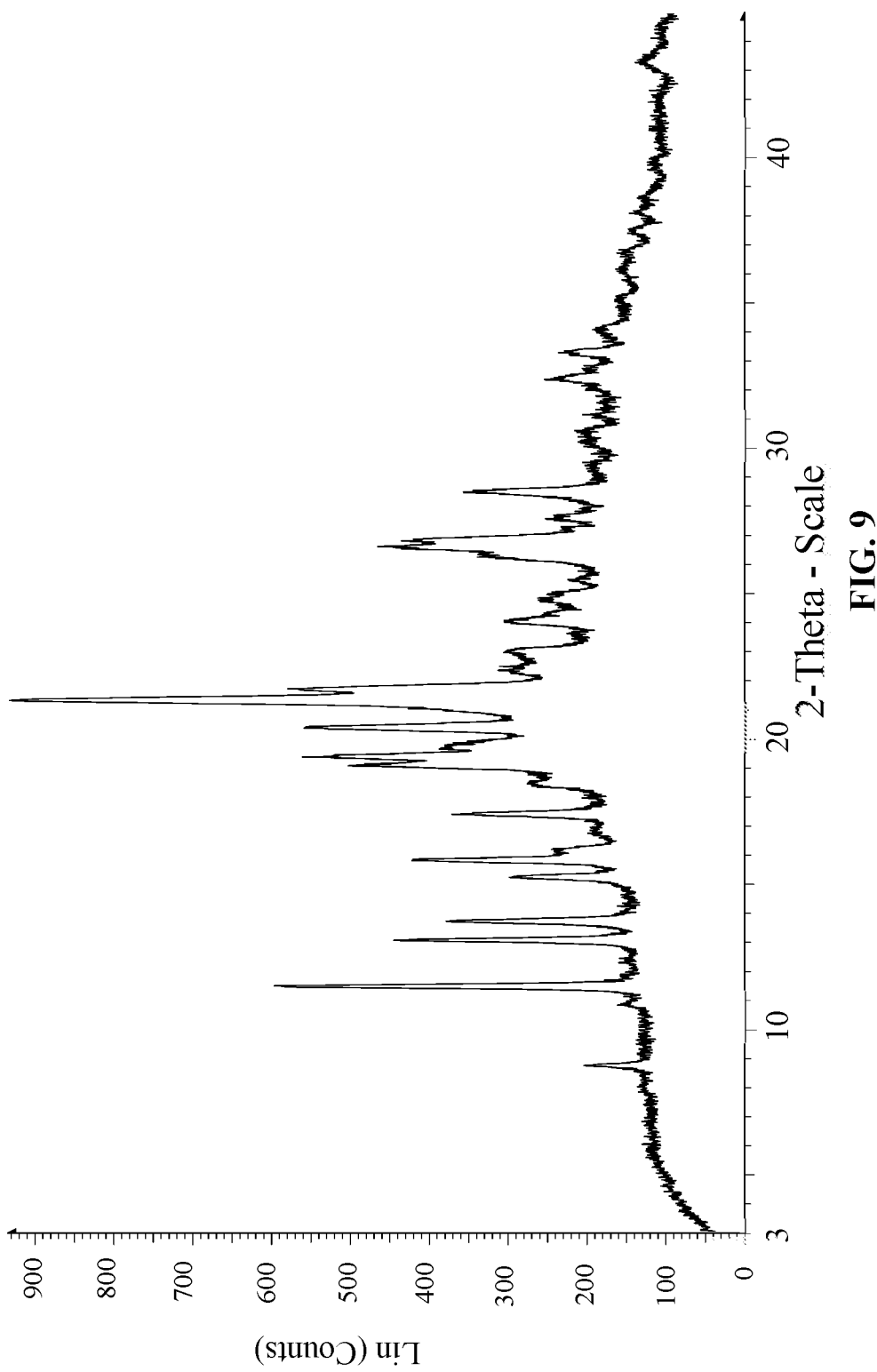
FIG. 9 illustrates the x-ray powder diffraction patterns of a Crystalline Form of a malonate salt of compound I-3 in Example 2.

In another embodiment, the disclosure relates to a crystalline form of a malonate salt of compound I-3 of Example 2 having an X-ray diffraction spectrum substantially the same as the X-ray powder diffraction spectrum shown in FIG. 9.

Figure 10:
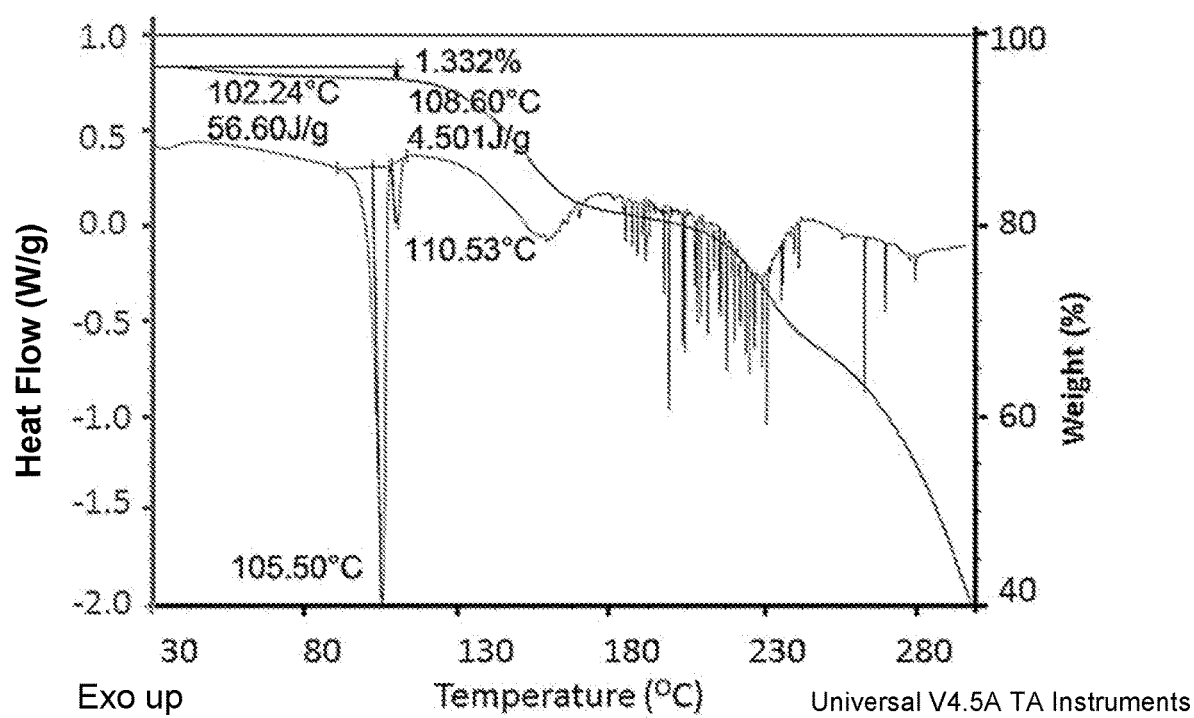
FIG. 10 illustrates the differential scanning calorimetry (DSC) and thermogravimetric analysis (TGA) of a Crystalline Form of a malonate salt of compound I-3 in Example 2.

In yet another embodiment, the disclosure relates to a crystalline form of a malonate salt of compound I-3 of Example 2 having a differential scanning calorimetry (DSC) thermogram/thermo gravimetric analysis (TGA) diagram substantially the same as that shown in shown in FIG. 10.

In another embodiment, the disclosure relates to a crystalline form of a malonate salt of compound I-3 of Example 2 having a differential scanning calorimetry (DSC) thermogram substantially the same as that shown in shown in FIG. 10.

In yet another embodiment, the disclosure relates to a crystalline form of a malonate salt of compound I-3 of Example 2 having a thermo gravimetric analysis (TGA) diagram substantially the same as that shown in shown in FIG. 10.

In another embodiment, the disclosure relates to a crystalline form of a fumarate salt of compound I-3 of Example 2.

In yet another embodiment, the disclosure relates to a crystalline form of a fumarate salt of compound I-3 of Example 2 characterized by a x-ray powder diffraction pattern comprising three or more 2θpeaks selected from the group consisting of 6.6±0.1°, 8.8±0.1°, 13.1±0.1°, 13.2±0.1°, 10.6±0.1°, 15.4±0.1°, 17.7±0.1°, 19.2±0.1°, 20.2±0.1°, 22.1±0.1°, 24.7±0.1°, 26.5±0.1°, and 28.9±0.1°.

In another embodiment, the disclosure relates to a crystalline form of a fumarate salt of compound I-3 of Example 2 characterized by a x-ray powder diffraction pattern comprising four or more 2θpeaks selected from the group consisting of 6.6±0.1°, 8.8±0.1°, 13.1±0.1°, 13.2±0.1°, 10.6±0.1°, 15.4±0.1°, 17.7±0.1°, 19.2±0.1°, 20.2±0.1°, 22.1±0.1°, 24.7±0.1°, 26.5±0.1°, and 28.9±0.1°.

In yet another embodiment, the disclosure relates to a crystalline form of a fumarate salt of compound I-3 of Example 2 characterized by a x-ray powder diffraction pattern comprising five or more 2θpeaks selected from the group consisting of 6.6±0.1°, 8.8±0.1°, 13.1±0.1°, 13.2±0.1°, 10.6±0.1°, 15.4±0.1°, 17.7±0.1°, 19.2±0.1°, 20.2±0.1°, 22.1±0.1°, 24.7±0.1°, 26.5±0.1°, and 28.9±0.1°.

In yet another embodiment, the disclosure relates to a crystalline form of a fumarate salt of compound I-3 of Example 2 characterized by a x-ray powder diffraction pattern comprising 2-theta peaks (2θ) at 8.8±0.1°, 13.1±0.1°, 13.2±0.1°, 19.2±0.1°, and 22.1±0.1°. In another embodiment, the crystalline form of a fumarate salt of compound I-3 of Example 2 further comprises a 2-theta peak at 20.2±0.1. In yet another embodiment, the crystalline form of a fumarate salt of compound I-3 of Example 2 further comprises a 2-theta peak at 24.7±0.1°. In another embodiment, the crystalline form of a fumarate salt of compound I-3 of Example 2 further comprises a 2-theta peak at 20.2±0.1° and 24.7±0.1°.

Figure 11:
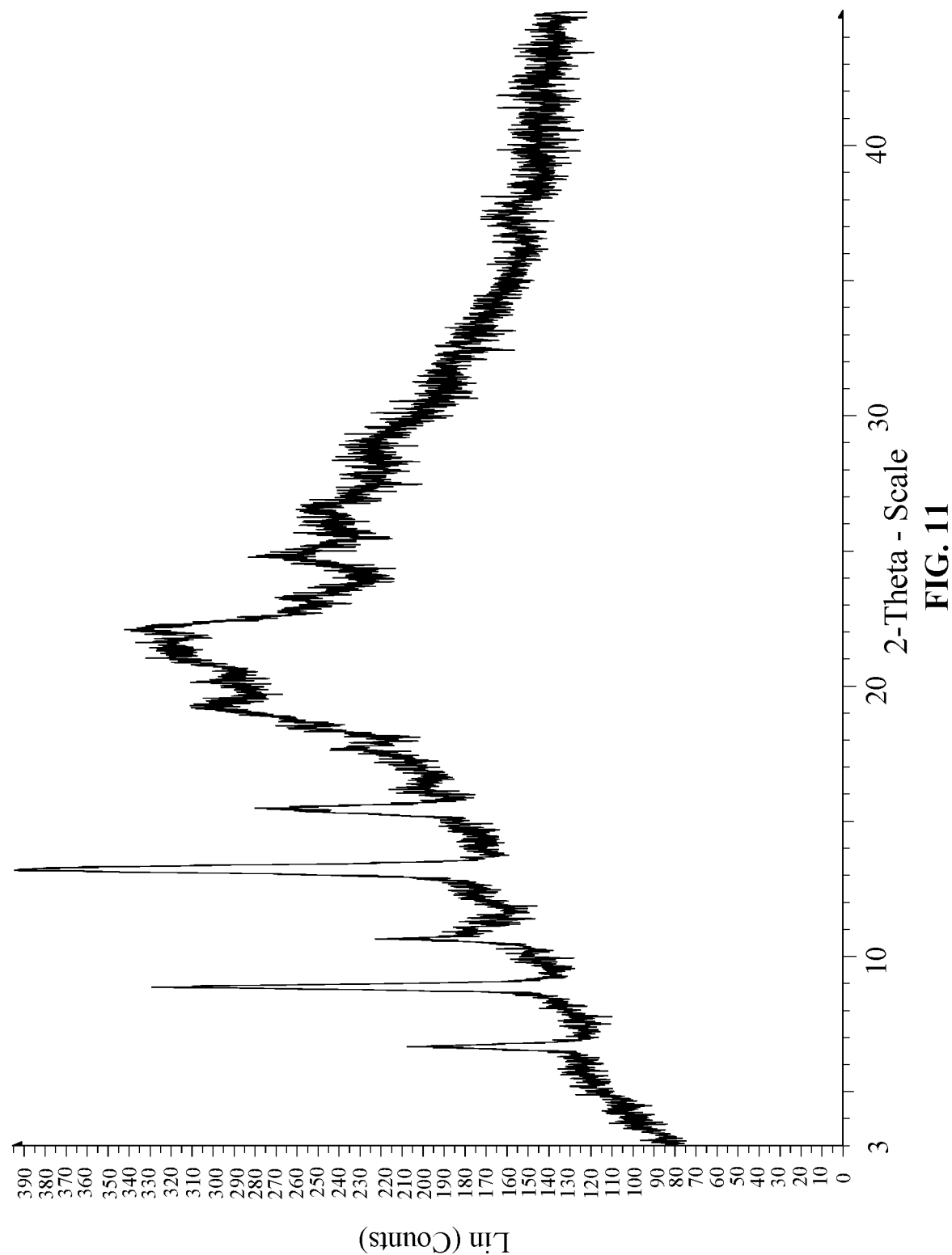
FIG. 11 illustrates the x-ray powder diffraction patterns of a Crystalline Form of a fumarate salt of compound I-3 in Example 2.

In another embodiment, the disclosure relates to a crystalline form of a fumarate salt of compound I-3 of Example 2 having an X-ray diffraction spectrum substantially the same as the X-ray powder diffraction spectrum shown in FIG. 11.

Figure 12:
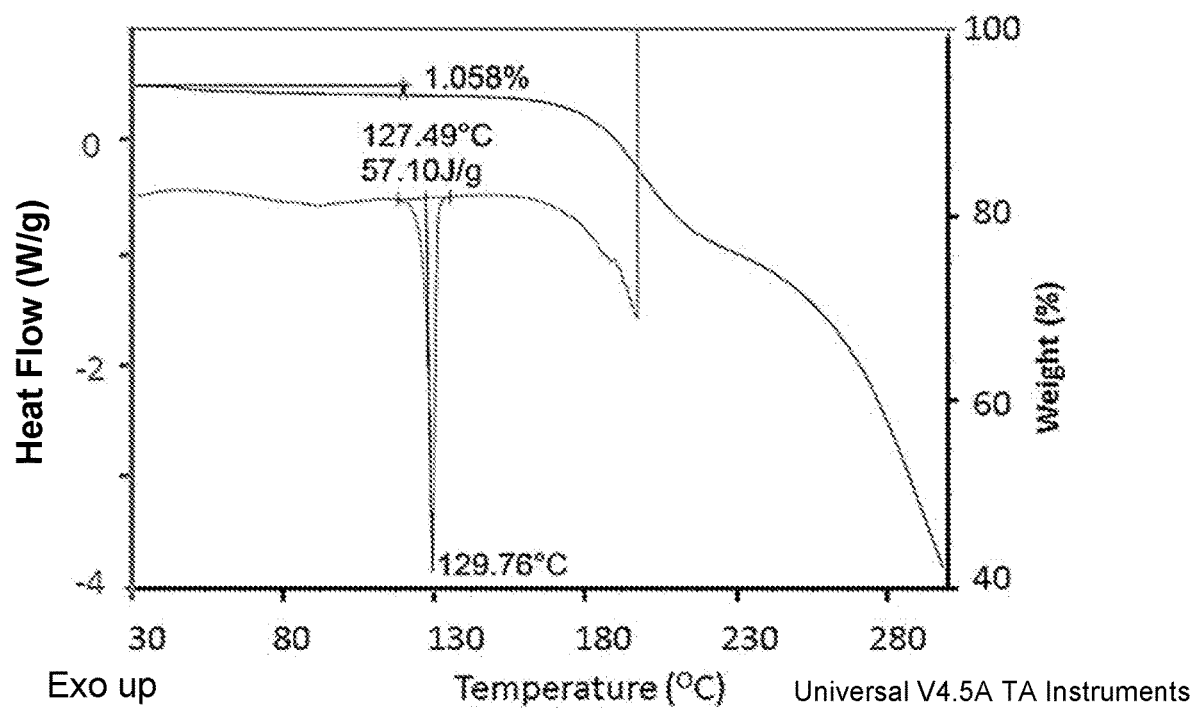
FIG. 12 illustrates the differential scanning calorimetry (DSC) and thermogravimetric analysis (TGA) of a Crystalline Form of a fumarate salt of compound I-3 in Example 2.

In yet another embodiment, the disclosure relates to a crystalline form of a fumarate salt of compound I-3 of Example 2 having a differential scanning calorimetry (DSC) thermogram/thermo gravimetric analysis (TGA) diagram substantially the same as that shown in shown in FIG. 12.

In another embodiment, the disclosure relates to a crystalline form of a fumarate salt of compound I-3 of Example 2 having a differential scanning calorimetry (DSC) thermogram substantially the same as that shown in shown in FIG. 12.

In yet another embodiment, the disclosure relates to a crystalline form of a fumarate salt of compound I-3 of Example 2 having a thermo gravimetric analysis (TGA) diagram substantially the same as that shown in shown in FIG. 12.

The term "substantially the same" with reference to X-ray diffraction peak positions means that typical peak position and intensity variability are taken into account. For example, one skilled in the art will appreciate that the peak positions (2Θ) will show some inter-apparatus variability, typically as much as 0.2°. Occasionally, the variability could be higher than 0.2° depending on apparatus calibration differences. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measure only.

The compounds and/or crystalline forms, or pharmaceutically acceptable salts thereof, of the present disclosure may possess improved stability, hygroscopicity, high aqueous solubility and/or pharmaceutical processability over known NEP inhibitor compounds (i.e., sacubitril (AHU377)). For example, the compounds and/or crystalline forms, or pharmaceutically acceptable salts thereof, may possess powder-like appearance and good flowability, which is favorable for pharmaceutical processing.

Non-limiting illustrative compounds of the disclosure include:

| Compound No. | Structure | Compound Name |
|---|---|---|
| I-1 | 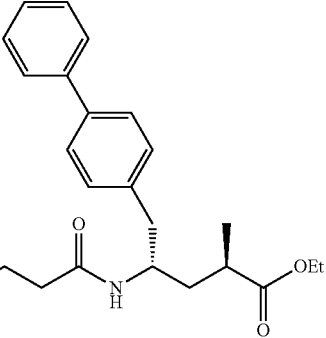 | (4-(((2S,4R)-1-([1,1'-biphenyl]-4-yl)-5-ethoxy-4-methyl-5-oxopentan-2-yl)amino)-4-oxobutanoyl)-L-leucine |
| I-2 | 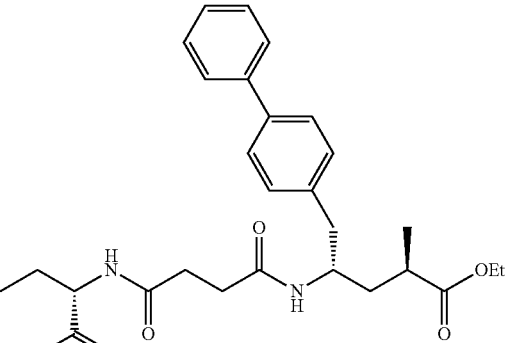 | (4-(((2S,4R)-1-([1,1'-biphenyl]-4-yl)-5-ethoxy-4-methyl-5-oxopentan-2-yl)amino)-4-oxobutanoyl)-L-lysine |

-continued

| Compound No. | Structure | Compound Name |
|---|---|---|
| I-3 | 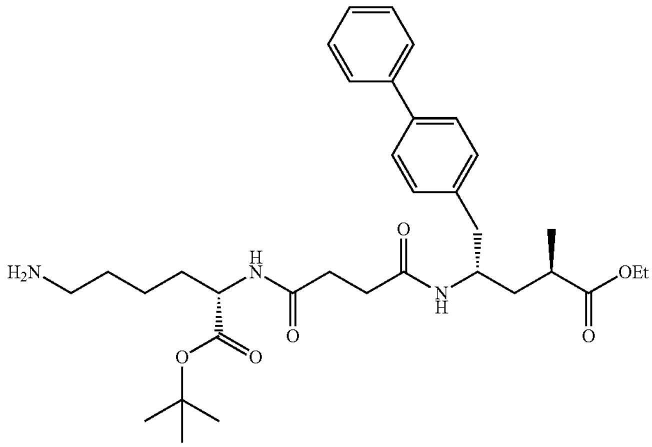 | tert-butyl (4-(((2S,4R)-1-([1,1'-biphenyl]-4-yl)-5-ethoxy-4-methyl-5-oxopentan-2-yl)amino)-4-oxobutanoyl)-L-lysinate |
| I-4 | 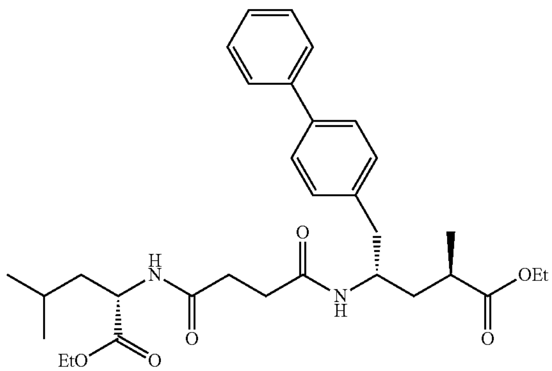 [SMILES: CCOC(=O)[C@H](C)C[C@@H](Cc1ccc(-c2ccccc2)cc1)NC(=O)CCC(=O)N[C@@H](CC(C)C)C(=O)O] | ethyl (2R,4S)-5-([1,1'-biphenyl]-4-yl)-4-(4-(((S)-1-ethoxy-4-methyl-1-oxopentan-2-yl)amino)-4-oxobutanamido)-2-methylpentanoate |
| I-5 | 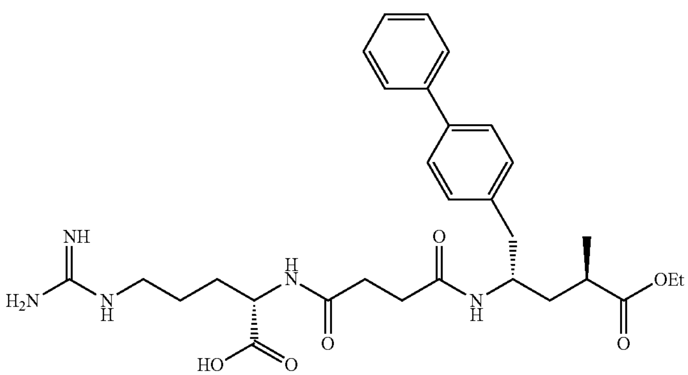 [SMILES: CCOC(=O)[C@H](C)C[C@@H](Cc1ccc(-c2ccccc2)cc1)NC(=O)CCC(=O)N[C@@H](CCCNC(=N)N)C(=O)O] | (4-(((2S,4R)-1-([1,1'-biphenyl]-4-yl)-5-ethoxy-4-methyl-5-oxopentan-2-yl)amino)-4-oxobutanoyl)-L-arginine |
| I-6 | 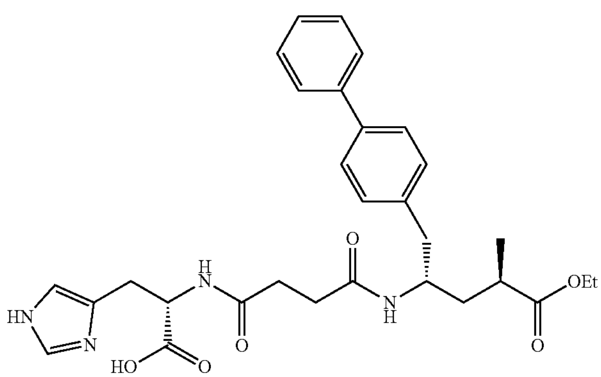 [SMILES: CCOC(=O)[C@H](C)C[C@@H](Cc1ccc(-c2ccccc2)cc1)NC(=O)CCC(=O)N[C@@H](Cc1c[nH]cn1)C(=O)O] | (4-(((2S,4R)-1-([1,1'-biphenyl]-4-yl)-5-ethoxy-4-methyl-5-oxopentan-2-yl)amino)-4-oxobutanoyl)-L-histidine |

-continued

| Compound No. | Structure | Compound Name |
|---|---|---|
| I-7 | 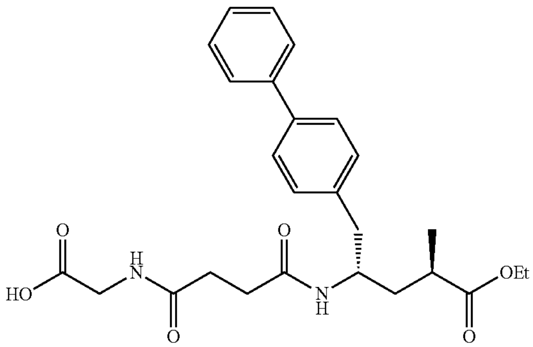 [SMILES: CCOC(=O)[C@H](C)C[C@@H](Cc1ccc(-c2ccccc2)cc1)NC(=O)CCC(=O)NCC(=O)O] | (4-(((2S,4R)-1-([1,1'-biphenyl]-4-yl)-5-ethoxy-4-methyl-5-oxopentan-2-yl)amino)-4-oxobutanoyl)glycine |
| I-8 | 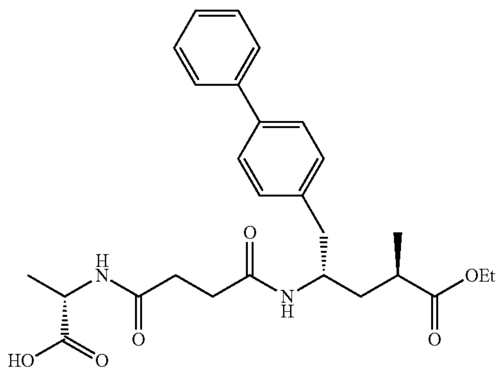 [SMILES: CCOC(=O)[C@H](C)C[C@@H](Cc1ccc(-c2ccccc2)cc1)NC(=O)CCC(=O)N[C@@H](C)C(=O)O] | (4-(((2S,4R)-1-([1,1'-biphenyl]-4-yl)-5-ethoxy-4-methyl-5-oxopentan-2-yl)amino)-4-oxobutanoyl)-L-alanine |
| I-9 | 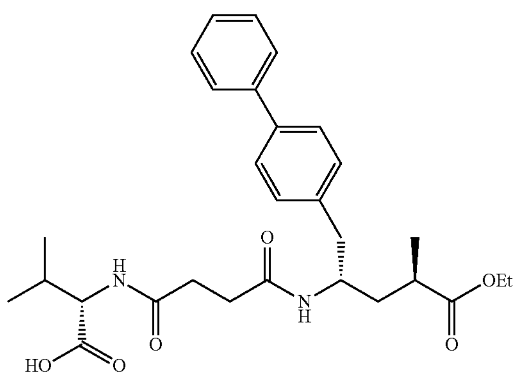 [SMILES: CCOC(=O)[C@H](C)C[C@@H](Cc1ccc(-c2ccccc2)cc1)NC(=O)CCC(=O)N[C@H](C(=O)O)C(C)C] | (4-(((2S,4R)-1-([1,1'-biphenyl]-4-yl)-5-ethoxy-4-methyl-5-oxopentan-2-yl)amino)-4-oxobutanoyl)-L-valine |
| I-10 | 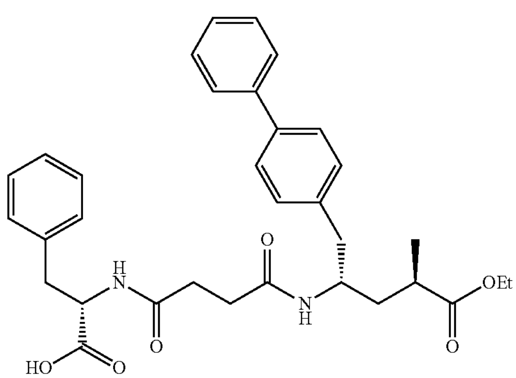 [SMILES: CCOC(=O)[C@H](C)C[C@@H](Cc1ccc(-c2ccccc2)cc1)NC(=O)CCC(=O)N[C@@H](Cc1ccccc1)C(=O)O] | (4-(((2S,4R)-1-([1,1'-biphenyl]-4-yl)-5-ethoxy-4-methyl-5-oxopentan-2-yl)amino)-4-oxobutanoyl)-L-phenylalanine |

| Compound No. | Structure | Compound Name |
|---|---|---|
| I-11 | 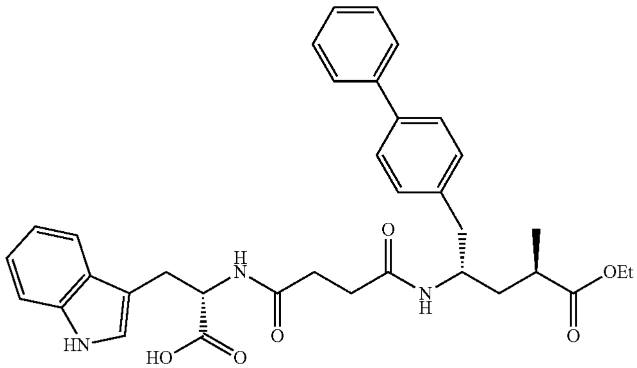 [SMILES: CCOC(=O)[C@H](C)C[C@@H](Cc1ccc(-c2ccccc2)cc1)NC(=O)CCC(=O)N[C@@H](Cc1c[nH]c2ccccc12)C(=O)O] | (4-(((2S,4R)-1-([1,1'-biphenyl]-4-yl)-5-ethoxy-4-methyl-5-oxopentan-2-yl)amino)-4-oxobutanoyl)-L-tryptophan |
| I-12 | 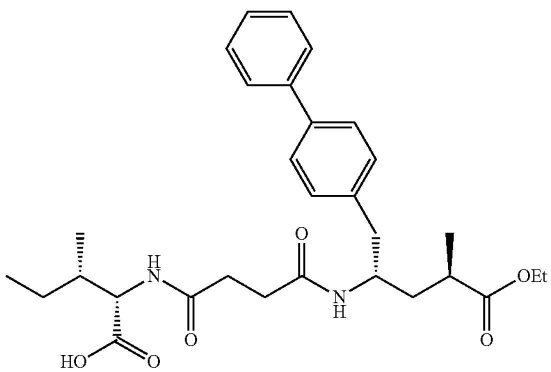 [SMILES: CCOC(=O)[C@H](C)C[C@@H](Cc1ccc(-c2ccccc2)cc1)NC(=O)CCC(=O)N[C@H](C(=O)O)[C@@H](C)CC] | (4-(((2S,4R)-1-([1,1'-biphenyl]-4-yl)-5-ethoxy-4-methyl-5-oxopentan-2-yl)amino)-4-oxobutanoyl)-L-isoleucine |

It will be noted that the structure of some of the compounds of this disclosure includes asymmetric carbon atoms. It is to be understood accordingly that the isomers arising from such asymmetry (e.g., all enantiomers and diastereomers) are included within the scope of this disclosure, unless indicated otherwise. Such isomers can be obtained in substantially pure form by classical separation techniques and by stereochemically controlled synthesis. Furthermore, the structures and other compounds and moieties discussed in this application also include all tautomers thereof.

As used herein, the term "isomers" refers to different compounds that have the same molecular Formula but differ in arrangement and configuration of the atoms. Also as used herein, the term "an optical isomer" or "a stereoisomer" refers to any of the various stereoisomeric configurations which may exist for a given compound of the present disclosure and includes geometric isomers. It is understood that a substituent may be attached at a chiral center of a carbon atom. Therefore, the disclosure includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" and "diastereomers" can be used interchangeably and are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present disclosure is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

"Stereoisomer" or "optical isomer" mean a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the disclosure which may give rise to stereoisomerism, the disclosure contemplates stereoisomers and mixtures thereof. The compounds of the disclosure and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures. As discussed in more detail below, individual stereoisomers of compounds are prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

"Enantiomers" means a pair of stereoisomers that are non-superimposable mirror images of each other.

"Diastereoisomers" or "diastereomers" mean optical isomers which are not mirror images of each other.

"Racemic mixture" or "racemate" mean a mixture containing equal parts of individual enantiomers.

"Non-racemic mixture" means a mixture containing unequal parts of individual enantiomers.

"Geometrical isomer" means a stable isomer which results from restricted freedom of rotation about double bonds (e.g., cis-2-butene and trans-2-butene) or in a cyclic structure (e.g., cis-1,3-dichlorocyclobutane and trans-1,3-dichlorocyclobutane). Because carbon-carbon double (olefinic) bonds, C=N double bonds, cyclic structures, and the like may be present in the compounds of the disclosure, the disclosure contemplates each of the various stable geometric isomers and mixtures thereof resulting from the arrangement of substituents around these double bonds and in these cyclic structures. The substituents and the isomers are designated using the cis/trans convention or using the E or Z system, wherein the term "E" means higher order substituents on opposite sides of the double bond, and the term "Z" means higher order substituents on the same side of the double bond. A thorough discussion of E and Z isomerism is provided in J. March, Advanced Organic Chemistry: Reactions, Mechanisms, and Structure, 4th ed., John Wiley & Sons, 1992, which is hereby incorporated by reference in its entirety. Several of the following examples represent single E isomers, single Z isomers, and mixtures of E/Z isomers. Determination of the E and Z isomers can be done by analytical methods such as x-ray crystallography, 1H NMR, and 13C NMR.

Some of the compounds of the disclosure can exist in more than one tautomeric form. As mentioned above, the compounds of the disclosure include all such tautomers.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the disclosure from this disclosure and the knowledge of the prior art.

Thus, although the racemic form of drug may be used, it is often less effective than administering an equal amount of enantiomerically pure drug; indeed, in some cases, one enantiomer may be pharmacologically inactive and would merely serve as a simple diluent. For example, although ibuprofen had been previously administered as a racemate, it has been shown that only the S-isomer of ibuprofen is effective as an anti-inflammatory agent (in the case of ibuprofen, however, although the R-isomer is inactive, it is converted in vivo to the S-isomer, thus, the rapidity of action of the racemic form of the drug is less than that of the pure S-isomer). Furthermore, the pharmacological activities of enantiomers may have distinct biological activity. For example, S-penicillamine is a therapeutic agent for chronic arthritis, while R-penicillamine is toxic. Indeed, some purified enantiomers have advantages over the racemates, as it has been reported that purified individual isomers have faster transdermal penetration rates compared to the racemic mixture. See U.S. Pat. Nos. 5,114,946 and 4,818,541.

Thus, if one enantiomer is pharmacologically more active, less toxic, or has a preferred disposition in the body than the other enantiomer, it would be therapeutically more beneficial to administer that enantiomer preferentially. In this way, the patient undergoing treatment would be exposed to a lower total dose of the drug and to a lower dose of an enantiomer that is possibly toxic or an inhibitor of the other enantiomer.

Preparation of pure enantiomers or mixtures of desired enantiomeric excess (ee) or enantiomeric purity are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

In general, all tautomeric forms and isomeric forms and mixtures, whether individual geometric isomers or stereoisomers or racemic or non-racemic mixtures, of a chemical structure or compound is intended, unless the specific stereochemistry or isomeric form is specifically indicated in the compound name or structure.

Any asymmetric atom (e.g., carbon or the like) of the compound(s) of the present disclosure can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present disclosure can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present disclosure into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Any Formula given herein is also intended to represent unlabeled forms as well as isotopically labeled forms of the compounds. For example, any hydrogen represented by "H" in any of the Formulae herein is intended to represent all isotopic forms of hydrogen (e.g. $^1H$, $^2H$ or D, $^3H$); any carbon represented by "C" in any of the Formulae herein is intended to represent all isotopic forms of carbon (e.g. $^{11}C$, $^{13}C$, $^{14}C$); any nitrogen represented by "N" is intended to represent all isotopic forms of nitrogen (e.g. $^{14}N$, $^{15}N$). Other examples of isotopes that are included in the disclosure include isotopes of oxygen, sulfur, phosphorous, fluorine, iodine and chlorine, such as $^{18}F$ $^{31}P$, $^{32}P$, $^{35}S$, $^{36}Cl$, $^{125}I$. The disclosure includes various isotopically labeled compounds as defined herein, for example those into which radioactive isotopes, such as $^3H$, $^{13}C$, and $^{14}C$ are present. In one embodiment, the atoms in the Formulae herein occur in their natural abundance. In another embodiment, one or more hydrogen atoms may be enriched in $^2H$; or/and one or more carbon atom may be enriched in $^{11}C$, $^{13}C$ or $^{14}C$; or/and one or more nitrogens may be enriched in $^{14}N$. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

Further, enrichment with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the Formula (I) or (II). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically enriched compounds of Formula (I) or (II) can generally be prepared by conventional techniques known to those skilled in the art or by processes analogous to those described in the accompanying Examples and Preparations using an appropriate isotopically enriched reagent in place of the non-enriched reagent previously employed.

Pharmaceutically acceptable solvates in accordance with the disclosure include those wherein the solvent of crystallization may be isotopically substituted, e.g. $D_2O$, $d_6$-acetone, $d_6$-DMSO.

Compounds of the disclosure, i.e., compounds according to Formula (I) or (II) that contain groups capable of acting as donors and/or acceptors for hydrogen bonds may be capable of forming co-crystals with suitable co-crystal formers. These co-crystals may be prepared from compounds according to Formula (I) or (II) by known co-crystal forming procedures. Such procedures include grinding, heating, co-subliming, co-melting, or contacting in solution compounds according to Formula (I) or (II) with the co-crystal former under crystallization conditions and isolating co-crystals thereby formed. Suitable co-crystal formers include those described in WO 2004/078163. Hence the disclosure further provides co-crystals comprising a compound according to Formula (I) or (II) or a pharmaceutically acceptable salt thereof.

All methods described herein can be performed in any suitable order unless otherwise indicated herein or otherwise clearly contradicted by context. The use of any and all examples, or exemplary language (e.g. "such as") provided herein is intended merely to better illuminate the disclosure and does not pose a limitation on the scope of the disclosure otherwise claimed.

Compounds of the present disclosure are either obtained in the free form, as a salt thereof, or as prodrug derivatives thereof.

Furthermore, the compounds of the present disclosure, including their salts, can also be obtained in the form of their hydrates, or include other solvents used for their crystallization.

Methods of Synthesizing Compounds of Formulae (I) and (II)

The compounds of the disclosure can be synthesized using the methods described in the following schemes, examples, and by using art recognized techniques. All compounds described herein are included in the disclosure as compounds. Compounds of the disclosure may be synthesized according to at least one of the methods described in the scheme below.

Within the scope of this text, only a readily removable group that is not a constituent of the particular desired end product of the compounds of the present disclosure is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999.

Salts of compounds of the present disclosure having at least one salt-forming group may be prepared in a manner known per se. For example, salts of compounds of the present disclosure having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present disclosure are obtained in customary manner, e.g. by treating the compounds with an acid or a suitable anion exchange reagent. Internal salts of compounds of the present disclosure containing acid and basic salt-forming groups, e.g. a free carboxy group and a free amino group, may be formed, e.g. by the neutralization of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the disclosure can be separated in a manner known per se into the individual isomers; diastereoisomers can be separated, for example, by partitioning between polyphasic solvent mixtures, recrystallization and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

Those skilled in the art will recognize if a stereocenter exists in the compounds of the present disclosure. Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80° C. to −60° C., at room temperature, at from −20° C. to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The disclosure relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the disclosure is produced under the process conditions and processed further in situ.

All starting materials, building blocks, reagents, acids, bases, dehydrating agents, solvents and catalysts utilized to synthesize the compounds of the present disclosure are either commercially available or can be produced by organic synthesis methods known to one of ordinary skill in the art (Houben-Weyl $4^{th}$ Ed. 1952, Methods of Organic Synthesis, Thieme, Volume 21).

Preparation of Compounds

The compounds of the present disclosure can be prepared in a number of ways well known to those skilled in the art of organic synthesis. By way of example, compounds of the present disclosure can be synthesized using the methods described below, together with synthetic methods known in the art of synthetic organic chemistry, or variations thereon as appreciated by those skilled in the art. Preferred methods include but are not limited to those methods described below.

Compounds of the present disclosure can be synthesized by following the steps outlined in General Scheme I which comprises a sequence of assembling intermediates 1-b, 1-c and 1-d. Intermediate 1-b can be made by treating sacubitril calcium salt (1-a) with an acid, for example, hydrochloric acid, for example, as detailed in Example 1 herein. Starting materials are either commercially available or made by known procedures in the reported literature or as illustrated.

General Scheme I

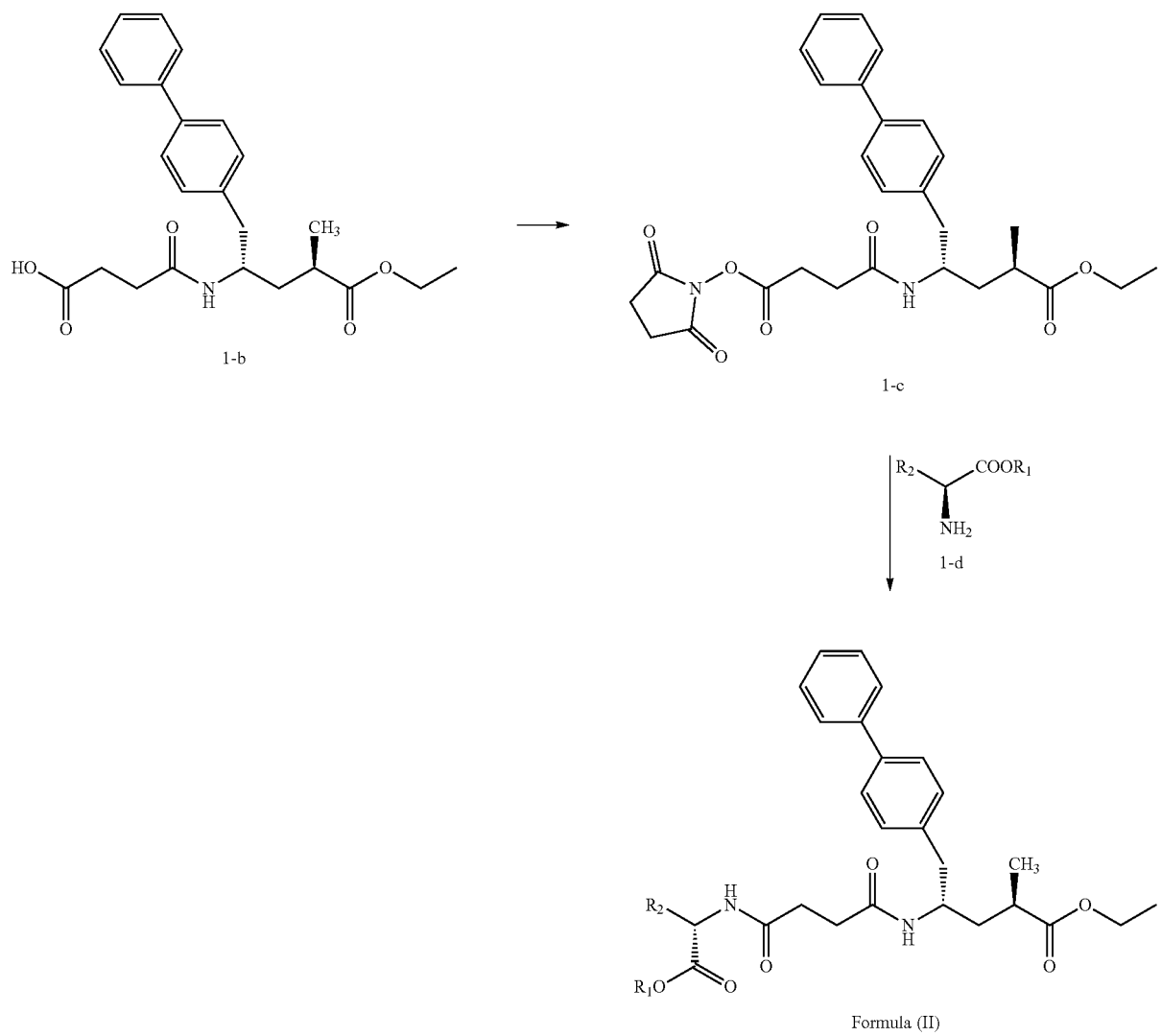

wherein $R^1$ and $R^2$ are as defined in Formulae (I) and (II).

The general way of preparing compounds of Formulae (I) and (II) using intermediates 1-b, 1-c, and 1-d is outlined in General Scheme I. Coupling of I-b with hydroxy succinamide in the presence of an amino acid coupling agent (e.g., EDC HCl) and in a solvent (e.g., dimethylformamide (DMF)) yields ester 1-c. Treatment of 1-c with amine 1-d in the presence of a base (e.g., sodium bicarbonate (NaHCO$_3$)) and in a solvent (e.g., tetrahydrofuran (THF)) provides a compound of Formula (I) or (II).

The disclosure further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the disclosure and intermediates can also be converted into each other according to methods generally known to those skilled in the art.

Methods of Using the Compounds of Formulae (I) and (II)

Another aspect of the disclosure relates to a method of treating, preventing, inhibiting, or eliminating a disease or disorder in a subject associated with modulation of neutral endopeptidase activity. The method comprises administering to a subject in need of a treatment for diseases or disorders associated with modulation of neutral endopeptidase activity an effective amount of a compound of Formula (I) or (II), or a pharmaceutically acceptable salt, hydrate, solvate, prodrug, stereoisomer, or tautomer thereof, or a composition comprising a compound of Formula (I) or (II), or a pharmaceutically acceptable salt, hydrate, solvate, prodrug, stereoisomer, or tautomer thereof and one or more pharmaceutically acceptable carriers. In some embodiments, the compound or composition is administered to patients already or concomitantly being treated with an Angiotensin Receptor Blocker. In one embodiment, the Angiotensin Receptor Blocker is selected from valsartan, candesartan, losartan, irbesartan, telmisartan, olmesartan, eprosartan, fimasartan, and azilsartan, or a pharmaceutically acceptable salt thereof. In another embodiment, the Angiotensin Receptor Blocker is valsartan, or a pharmaceutically acceptable salt thereof. In another embodiment, the compound or the composition is administered together, concomitantly or sequentially with the Angiotensin Receptor Blocker valsartan, or a pharmaceutically acceptable salt thereof.

In another aspect, the present disclosure relates to a method of treating, preventing, inhibiting, or eliminating a disease or disorder in a subject associated with inhibiting neutral endopeptidase activity. The method comprises administering to a subject in need of treatment for diseases or disorders associated with neutral endopeptidase activity an effective amount of a compound of Formula (I) or (II), or a pharmaceutically acceptable salt, hydrate, solvate, prodrug, stereoisomer, or tautomer thereof, or a composition comprising a compound of Formula (I) or (II), or a pharmaceutically acceptable salt, hydrate, solvate, prodrug, stereoisomer, or tautomer thereof and one or more pharmaceutically acceptable carriers. In some embodiments, the compound or the composition is administered to patients already or concomitantly being treated with an Angiotensin Receptor Blocker. In one embodiment, the Angiotensin Receptor Blocker is selected from valsartan, candesartan, losartan, irbesartan, telmisartan, olmesartan, eprosartan, fimasartan, and azilsartan, or a pharmaceutically acceptable salt thereof. In another embodiment, the Angiotensin Receptor Blocker is valsartan, or a pharmaceutically acceptable salt thereof. In another embodiment, the compound or the composition is administered together, concomitantly or sequentially with the Angiotensin Receptor Blocker valsartan, or a pharmaceutically acceptable salt thereof.

Thus, as a further embodiment, the present disclosure provides the use of a compound according to Formula (I) or (II), or a pharmaceutically acceptable salt, hydrate, solvate, prodrug, stereoisomer, or tautomer thereof for the treatment of a disease which is associated with neutral endopeptidase activity. In another embodiment, the disease is selected from the aforementioned list, suitably hypertension, pulmonary heart disease, pulmonary hypertension, pulmonary arterial hypertension, isolated systolic hypertension, resistant hypertension, peripheral vascular disease, heart failure, heart failure with preserved ejection fraction (HF-PEF), heart failure with reduced ejection fraction (HF-REF), mitral stenosis and regurgitation, left ventricular hypertrophy, angina, renal insufficiency, renal failure (including edema and salt retention), diabetic nephropathy, non-diabetic nephropathy, contrast induced nephropathy, type-2 diabetes, and diabetic complications and most suitably cardiovascular disorders, such as hypertension, renal insufficiency including edema.

Another aspect of the disclosure relates to a method of inhibiting neutral endopeptidase activity in a subject in need thereof. The method comprises administering to a subject in need an effective amount of a compound of Formula (I) or (II), or a pharmaceutically acceptable salt, hydrate, solvate, prodrug, stereoisomer, or tautomer thereof, or a composition comprising a compound of Formula (I) or (II), or a pharmaceutically acceptable salt, hydrate, solvate, prodrug, stereoisomer, or tautomer thereof. In some embodiments, the compound of Formula (I) or (II), or a pharmaceutically acceptable salt, hydrate, solvate, prodrug, stereoisomer, or tautomer thereof, or the composition comprising a compound of Formula (I) or (II), or a pharmaceutically acceptable salt, hydrate, solvate, prodrug, stereoisomer, or tautomer thereof, is administered to patients already or concomitantly being treated with an Angiotensin Receptor Blocker. In one embodiment, the Angiotensin Receptor Blocker is valsartan or a pharmaceutically acceptable salt thereof. In one embodiment, the compound of Formula (I) or (II), or a pharmaceutically acceptable salt, hydrate, solvate, prodrug, stereoisomer, or tautomer thereof, or the composition comprising a compound of Formula (I) or (II), or a pharmaceutically acceptable salt, hydrate, solvate, prodrug, stereoisomer, or tautomer thereof, is administered together, concomitantly or sequentially with the Angiotensin Receptor Blocker. In one embodiment, the Angiotensin Receptor Blocker is selected from valsartan, candesartan, losartan, irbesartan, telmisartan, olmesartan, eprosartan, fimasartan, and azilsartan, or a pharmaceutically acceptable salt thereof. In another embodiment, the Angiotensin Receptor Blocker is valsartan, or a pharmaceutically acceptable salt thereof.

In one embodiment, the compound of Formula (I) or (II), or a pharmaceutically acceptable salt, hydrate, solvate, prodrug, stereoisomer, or tautomer thereof, or the composition comprising a compound of Formula (I) or (II), or a pharmaceutically acceptable salt, hydrate, solvate, prodrug, stereoisomer, or tautomer thereof, and one or more pharmaceutically acceptable carriers is administered together with the Angiotensin Receptor Blocker valsartan, or a pharmaceutically acceptable salt thereof.

In another embodiment, the compound of Formula (I) or (II), or a pharmaceutically acceptable salt, hydrate, solvate, prodrug, stereoisomer, or tautomer thereof, or the composition comprising a compound of Formula (I) or (II), or a pharmaceutically acceptable salt, hydrate, solvate, prodrug, stereoisomer, or tautomer thereof, and one or more pharmaceutically acceptable carriers is administered concomitantly with the Angiotensin Receptor Blocker valsartan, or a pharmaceutically acceptable salt thereof.

In yet another embodiment, the compound of Formula (I) or (II), or a pharmaceutically acceptable salt, hydrate, solvate, prodrug, stereoisomer, or tautomer thereof, or the composition comprising a compound of Formula (I) or (II), or a pharmaceutically acceptable salt, hydrate, solvate, prodrug, stereoisomer, or tautomer thereof, and one or more pharmaceutically acceptable carriers is administered sequentially with the Angiotensin Receptor Blocker valsartan, or a pharmaceutically acceptable salt thereof.

In another embodiment, the disclosure provides a method of treating a disease which is associated with neutral endopeptidase activity comprising administration of a therapeutically acceptable amount of a compound according to Formula (I) or (II), or a pharmaceutically acceptable salt, hydrate, solvate, prodrug, stereoisomer, or tautomer thereof.

In one embodiment, the disclosure provides a product comprising a compound according to Formula (I) or (II), or a pharmaceutically acceptable salt, hydrate, solvate, prodrug, stereoisomer, or tautomer thereof, and at least one other therapeutic agent as a combined preparation for simultaneous, separate or sequential use in therapy. In one embodiment, the therapy is the treatment of a disease or condition associated with neutral endopeptidase activity.

Products provided as a combined preparation include a composition comprising the compound according to Formula (I) or (II), or a pharmaceutically acceptable salt, hydrate, solvate, prodrug, stereoisomer, or tautomer thereof, and the other therapeutic agent(s) together in the same pharmaceutical composition, or the compound according to Formula (I) or (II), or a pharmaceutically acceptable salt thereof, and the other therapeutic agent(s) in separate form, e.g. in the form of a kit.

In one embodiment, the disclosure provides a pharmaceutical composition comprising a compound according to Formula (I) or (II), or a pharmaceutically acceptable salt, hydrate, solvate, prodrug, stereoisomer, or tautomer thereof, and another therapeutic agent(s). Optionally, the pharmaceutical composition may comprise a pharmaceutically acceptable excipient, as described above.

In one embodiment, the disclosure provides a kit comprising two or more separate pharmaceutical compositions, at least one of which contains a compound according to Formula (I) or (II), or a pharmaceutically acceptable salt, hydrate, solvate, prodrug, stereoisomer, or tautomer thereof. In one embodiment, the kit comprises means for separately retaining said compositions, such as a container, divided bottle, or divided foil packet. An example of such a kit is a blister pack, as typically used for the packaging of tablets, capsules and the like.

The kit of the disclosure may be used for administering different dosage forms, for example, oral and parenteral, for administering the separate compositions at different dosage intervals, or for titrating the separate compositions against one another. To assist compliance, the kit of the disclosure typically comprises directions for administration.

In the combination therapies of the disclosure, the compound of the disclosure and the other therapeutic agent may be manufactured and/or Formulated by the same or different manufacturers. Moreover, the compound of the disclosure and the other therapeutic may be brought together into a combination therapy: (i) prior to release of the combination product to physicians (e.g. in the case of a kit comprising the compound of the disclosure and the other therapeutic agent); (ii) by the physician themselves (or under the guidance of the physician) shortly before administration; (iii) in the patient themselves, e.g. during sequential administration of the compound of the disclosure and the other therapeutic agent.

In one embodiment, the present disclosure relates to a combination comprising a compound according to Formula (I) or (II), or a pharmaceutically acceptable salt, hydrate, solvate, prodrug, stereoisomer, or tautomer thereof, or a composition comprising a compound according to Formula (I) or (II) or a pharmaceutically acceptable salt, hydrate, solvate, prodrug, stereoisomer, or tautomer thereof, and one or more pharmaceutically acceptable carriers, and one or more therapeutically active agents selected from HMG-Co-A reductase inhibitor, an angiotensin receptor blocker, a calcium channel blocker, an endothelin antagonist, a renin inhibitor, a diuretic, an ApoA-I mimic, an anti-diabetic agent, an obesity-reducing agent, an aldosterone receptor blocker, an endothelin receptor blocker, an aldosterone synthase inhibitor, a CETP inhibitor, and a phosphodiesterase type 5 (PDE5) inhibitor. In one embodiment, the combination comprises: a compound according to Formula (I) or (II), or a pharmaceutically acceptable salt, hydrate, solvate, prodrug, stereoisomer, or tautomer thereof, or a composition comprising a compound according to Formula (I) or (II) or a pharmaceutically acceptable salt, hydrate, solvate, prodrug, stereoisomer, or tautomer thereof, and one or more pharmaceutically acceptable carriers, and Angiotensin Receptor Blocker selected from valsartan, candesartan, losartan, irbesartan, telmisartan, olmesartan, eprosartan, fimasartan, and azilsartan, or a pharmaceutically acceptable salt thereof.

Accordingly, the disclosure provides the use of a compound according to Formula (I) or (II), or a pharmaceutically acceptable salt, hydrate, solvate, prodrug, stereoisomer, or tautomer thereof, for treating a disease or condition associated with neutral endopeptidase activity, wherein the medicament is prepared for administration with another therapeutic agent. The disclosure also provides the use of another therapeutic agent for treating a disease or condition associated with neutral endopeptidase activity, wherein the medicament is administered with a compound according to Formula (I) or (II), or a pharmaceutically acceptable salt, hydrate, solvate, prodrug, stereoisomer, or tautomer thereof.

The disclosure also provides a compound according to Formula (I) or (II), or a pharmaceutically acceptable salt, hydrate, solvate, prodrug, stereoisomer, or tautomer thereof, for use in a method of treating a disease or condition associated with neutral endopeptidase activity, wherein the compound is prepared for administration with another therapeutic agent. The disclosure also provides another therapeutic agent for use in a method of treating a disease or condition associated with neutral endopeptidase activity, wherein the other therapeutic agent is prepared for administration with a compound according to Formula (I) or (II), or a pharmaceutically acceptable salt, hydrate, solvate, prodrug, stereoisomer, or tautomer thereof.

The disclosure also provides the use of a compound according to Formula (I) or (II), or a pharmaceutically acceptable salt, hydrate, solvate, prodrug, stereoisomer, or tautomer thereof, or a composition comprising a compound according to Formula (I) or (II) or a pharmaceutically acceptable salt, hydrate, solvate, prodrug, stereoisomer, or tautomer thereof, and one or more pharmaceutically acceptable carriers for treating a disease or condition associated with neutral endopeptidase activity, wherein the patient has previously (e.g. within 24 hours) been treated with another therapeutic agent. The disclosure also provides the use of another therapeutic agent for treating a disease or condition associated with neutral endopeptidase activity, wherein the patient has previously (e.g. within 24 hours) been treated with a compound according to Formula (I) or (II), or a pharmaceutically acceptable salt, hydrate, solvate, prodrug, stereoisomer, or tautomer thereof.

In one embodiment, the other therapeutic agent is selected from: HMG-Co-A reductase inhibitor, an angiotensin receptor blocker (ARBs, angiotensin II receptor antagonist), a calcium channel blocker (CCB), an endothelin antagonist, a renin inhibitor, a diuretic, an ApoA-I mimic, an anti-diabetic agent, an obesity-reducing agent, an aldosterone receptor blocker, an endothelin receptor blocker, an aldosterone synthase inhibitor (ASI), a CETP inhibitor and a phophodiesterase type 5 (PDE5) inhibitor.

The term "in combination with" a second agent or treatment includes co-administration of the compound of the disclosure (e.g., a compound according to Formula (I) or (II), or a compound otherwise described herein) with the second agent or treatment, administration of the compound of the disclosure first, followed by the second agent or treatment and administration of the second agent or treatment first, followed by the compound of the disclosure.

The term "second agent" includes any agent which is known in the art to treat, prevent, or reduce the symptoms of a disease or disorder described herein, e.g., a disorder or disease responsive to the inhibition of neutral endopeptidase, such as for example, hypertension, pulmonary heart disease, pulmonary hypertension, pulmonary arterial hypertension, isolated systolic hypertension, resistant hypertension, peripheral vascular disease, heart failure, heart failure with preserved ejection fraction (HF-PEF), heart failure with reduced ejection fraction (HF-REF), mitral stenosis and regurgitation, left ventricular hypertrophy, angina, renal insufficiency (diabetic or non-diabetic), renal failure (including edema and salt retention), diabetic nephropathy, non-diabetic nephropathy, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, myocardial infarction (MI), renal fibrosis, polycystic kidney disease (PKD), renal failure (including edema and salt retention), cyclical oedema, Menière's disease, hyperaldosteronism (primary and secondary), hypercalciuria, ascites, glaucoma, menstrual disorders, pre-term labor, pre-eclampsia, endometriosis, reproductive disorders (especially male and female infertility, polycystic ovarian syndrome, implantation failure), asthma, obstructive sleep apnea, inflammation, leukemia, pain, epilepsy, affective disorders such as depression, obesity and gastrointestinal disorders (especially diarrhea and irritable bowel syndrome), wound healing (especially diabetic and venous ulcers and pressure sores), septic shock, the modulation of gastric acid secretion, the treatment of hyperreninemia, cystic fibrosis, restenosis, type-2 diabetes, metabolic syndrome, diabetic complications, atherosclerosis, and male and female sexual dysfunction.

Examples of second agents include HMG-Co-A reductase inhibitors, angiotensin II receptor antagonists, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI), phophodiesterase type 5 (PDE5) inhibitors and CETP inhibitors.

The term "HMG-Co-A reductase inhibitor" (also called beta-hydroxy-beta-methylglutaryl-co-enzyme-A reductase inhibitors) includes active agents that may be used to lower the lipid levels including cholesterol in blood. Examples include atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, pharmaceutically acceptable salts thereof.

The term "endothelin antagonist" includes bosentan (cf. EP 526708 A), tezosentan (cf. WO 96/19459), or, pharmaceutically acceptable salts thereof.

The term "renin inhibitor" includes ditekiren (chemical name: [1S-[1R*,2R*,4R*(1R*,2R*)]]-1-[(1,1-dimethylethoxy)carbonyl]-L-proly I-L-phenylalanyl-N-[2-hydroxy-5-methyl-1-(2-methylpropyl)-4-[[[2-methyl-1-[[(2-pyridinylmrthyl)amino]carbonyl]butyl]amino]carbonyl]hexyl]-N-alfa-methyl-L-histidinamide); terlakiren (chemical name: [R-(R*,S*)]-N-(4-morpholinylcarbonyl)-L-phenylalanyl-N-[1-(cyclohexylmethyl)-2-hydroxy-3-(1-methylethoxy)-3-oxopropyl]-S-methyl-L-cysteineamide); aliskiren (chemical name: (2S,4S,5S,7S)-5-amino-N-(2-carbamoyl-2,2-dimethylethyl)-4-hydroxy-7-{[4-methoxy-3-(3-methoxypropoxy)phenyl]methyl}-8-methyl-2-(propan-2-yl)nonanamide) and zankiren (chemical name: [1S-[1R*[R*(R*)], 2S*,3R*]]-N-[1-(cyclohexylmethyl)-2,3-dihydroxy-5-m ethylhexyl]-alfa-[[2-[[(4-methyl-1-piperazinyl)sulfonyl] methyl]-1-oxo-3-phenylpropyl]-amino]-4-thiazolepropanamide), or, hydrochloride salts thereof, or, SPP630, SPP635 and SPP800 as developed by Speedel, or RO 66-1132 and RO 66-1168 of Formula (A) and (B):

(A)
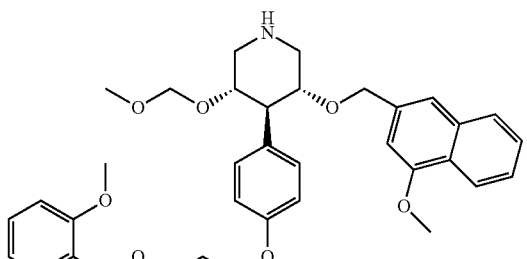

and (B)
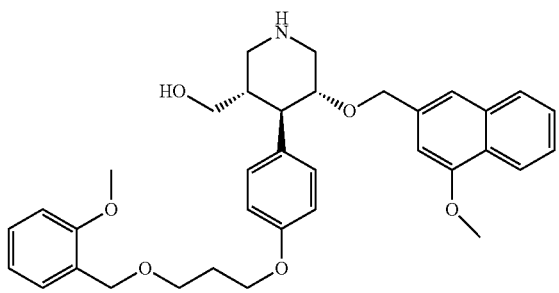

, pharmaceutically acceptable salts thereof.

The term "aliskiren", if not defined specifically, is to be understood both as the free base and as a salt thereof, especially a pharmaceutically acceptable salt thereof, most preferably a hemi-fumarate salt thereof.

An angiotensin II receptor antagonist or a pharmaceutically acceptable salt thereof is understood to be an active ingredient which binds to the $AT_1$-receptor subtype of angiotensin II receptor but does not result in activation of the receptor. As a consequence of the inhibition of the $AT_1$ receptor, these antagonists can, for example, be employed as antihypertensives or for treating heart failure.

The class of $AT_1$ receptor antagonists comprises compounds having differing structural features, essentially preferred are the non-peptidic ones. For example, mention may be made of the compounds which are selected from the group consisting of valsartan, candesartan, losartan, irbesartan, telmisartan, olmesartan, eprosartan, fimasartan, and azilsartan or, in each case, a pharmaceutically acceptable salt thereof.

Preferred $AT_1$-receptor antagonists are those agents which have been marketed, most preferred is valsartan or a pharmaceutically acceptable salt thereof.

The term "calcium channel blocker (CCB)" includes dihydropyridines (DHPs) and non-DHPs (e.g., diltiazem-type and verapamil-type CCBs). Examples include amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, or, pharmaceutically acceptable salts thereof. CCBs may be used as anti-hypertensive, anti-angina pectoris, or anti-arrhythmic drugs.

The term "diuretic" includes thiazide derivatives (e.g., chlorothiazide, hydrochlorothiazide, methylclothiazide, and chlorothalidon).

The term "ApoA-I mimic" includes D4F peptides (e.g., Formula D-W-F-K-A-F-Y-D-K-V-A-E-K-F-K-E-A-F).

The term "anti-diabetic agent" includes insulin secretion enhancers that promote the secretion of insulin from pancreatic □-cells. Examples include biguanide derivatives (e.g., metformin), sulfonylureas (SU) (e.g., tolbutamide, chlorpropamide, tolazamide, acetohexamide, 4-chloro-N-[(1-pyrolidinylamino)carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide, and tolylcyclamide), or pharmaceutically acceptable salts thereof. Further examples include phenylalanine derivatives (e.g., nateglinide [N-(trans-4-isopropylcyclohexylcarbonyl)-D-phenylalanine] (cf. EP 196222 and EP 526171) of the Formula

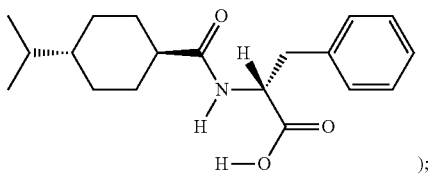 [SMILES: CC(C)[C@H]1CC[C@H](C(=O)N[C@H](Cc2ccccc2)C(=O)O)CC1]

repaglinide [(S)-2-ethoxy-4-{2-[[3-methyl-1-[2-(1-piperidinyl)phenyl]butyl]amino]-2-oxoethyl}benzoic acid] (cf. EP 589874, EP 147850 A2, in particular Example 11 on page 61, and EP 207331 A1); calcium (2S)-2-benzyl-3-(cis-hexahydro-2-isoindolinylcarbonyl)-propionate dihydrate (e.g., mitiglinide (cf. EP 507534)); and glimepiride (cf. EP 31058). Further examples include DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV inhibitor can be peptidic or, preferably, non-peptidic. DPP-IV inhibitors are in each case generically and specifically disclosed e.g. in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively. Other examples of DPP-IV inhibitor currently on the market are saxagliptin, sitagliptin, vidagliptin, and linagluptin.

GLP-1 is an insulinotropic protein which is described, e.g., by W. E. Schmidt et al. in *Diabetologia*, 28, 1985, 704-707 and in U.S. Pat. No. 5,705,483.

The term "GLP-1 agonists" includes variants and analogs of GLP-1(7-36)NH$_2$ which are disclosed in particular in U.S. Pat. Nos. 5,120,712, 5,118,666, 5,512,549, WO 91/11457 and by C. Orskov et al in J. Biol. Chem. 264 (1989) 12826. Further examples include GLP-1(7-37), in which compound the carboxy-terminal amide functionality of Arg$^{36}$ is displaced with Gly at the 37$^{th}$ position of the GLP-1(7-36)NH$_2$ molecule and variants and analogs thereof including GLN$^9$-GLP-1(7-37), D-GLN$^9$-GLP-1(7-37), acetyl LYS$^9$-GLP-1(7-37), LYS$^{18}$-GLP-1(7-37) and, in particular, GLP-1(7-37) OH, VAL$^8$-GLP-1(7-37), GLY$^8$-GLP-1(7-37), THR$^8$-GLP-1(7-37), MET$^8$-GLP-1(7-37) and 4-imidazopropionyl-GLP-1. Special preference is also given to the GLP agonist analog exendin-4, described by Greig et al. in Diabetologia 1999, 42, 45-50.

Also included in the definition "anti-diabetic agent" are insulin sensitivity enhancers which restore impaired insulin receptor function to reduce insulin resistance and consequently enhance the insulin sensitivity. Examples include hypoglycemic thiazolidinedione derivatives (e.g., glitazone, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl] methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy) phenyl]methyl}-thiazolidine-2,4-dione, 5-[3-(4-chloro-phenyl])-2-propynyl]-5-phenylsulfonyl)thiazolidine-2,4-dione, 5-[3-(4-chlorophenyl])-2-propynyl]-5-(4-fluorophenyl-sulfonyl)thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluoro-benzyloxy)naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297)).

Further anti-diabetic agents include, insulin signaling pathway modulators, like inhibitors of protein tyrosine phosphatases (PTPases), antidiabetic non-small molecule mimetic compounds and inhibitors of glutamine-fructose-6-phosphate amidotransferase (GFAT); compounds influencing a dysregulated hepatic glucose production, like inhibitors of glucose-6-phosphatase (G6Pase), inhibitors of fructose-1,6-bisphosphatase (F-1,6-Bpase), inhibitors of glycogen phosphorylase (GP), glucagon receptor antagonists and inhibitors of phosphoenolpyruvate carboxykinase (PEPCK); pyruvate dehydrogenase kinase (PDHK) inhibitors; inhibitors of gastric emptying; insulin; inhibitors of GSK-3; retinoid X receptor (RXR) agonists; agonists of Beta-3 AR; agonists of uncoupling proteins (UCPs); non-glitazone type PPARγ agonists; dual PPARα/PPARγ agonists; antidiabetic vanadium containing compounds; incretin hormones, like glucagon-like peptide-1 (GLP-1) and GLP-1 agonists; beta-cell imidazoline receptor antagonists; miglitol; α$_2$-adrenergic antagonists; and pharmaceutically acceptable salts thereof.

The term "obesity-reducing agent" includes lipase inhibitors (e.g., orlistat) and appetite suppressants (e.g., sibutramine and phentermine).

An aldosterone synthase inhibitor or a pharmaceutically acceptable salt thereof is understood to be an active ingredient that has the property to inhibit the production of aldosterone. Aldosterone synthase (CYP11B2) is a mitochondrial cytochrome P450 enzyme catalyzing the last step of aldosterone production in the adrenal cortex, i.e., the conversion of 11-deoxycorticosterone to aldosterone. The inhibition of the aldosterone production with so-called aldosterone synthase inhibitors is known to be a successful variant to treatment of hypokalemia, hypertension, heart failure, atrial fibrillation or renal failure. Such aldosterone synthase inhibition activity is readily determined by those skilled in the art according to standard assays (e.g., US 2007/0049616).

The class of aldosterone synthase inhibitors comprises both steroidal and non-steroidal aldosterone synthase inhibitors, the latter being most preferred.

Preference is given to commercially available aldosterone synthase inhibitors or those aldosterone synthase inhibitors that have been approved by the health authorities.

The class of aldosterone synthase inhibitors comprises compounds having differing structural features. For example, mention may be made of the compounds which are selected from the group consisting of the non-steroidal aromatase inhibitors anastrozole, fadrozole (including the (+)-enantiomer thereof), as well as the steroidal aromatase inhibitor exemestane, or, in each case where applicable, a pharmaceutically acceptable salt thereof.

The most preferred non-steroidal aldosterone synthase inhibitor is the (+)-enantiomer of the hydrochloride of fadrozole (U.S. Pat. Nos. 4,617,307 and 4,889,861) of Formula

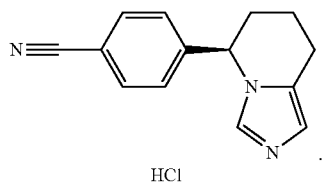 [SMILES: N#Cc1ccc([C@H]2CCCc3cncn32)cc1 ; Cl]

HCl or, if appropriable, a pharmaceutically acceptable salt thereof.

A preferred steroidal aldosterone antagonist is eplerenone (cf. EP 122232 A) of the Formula

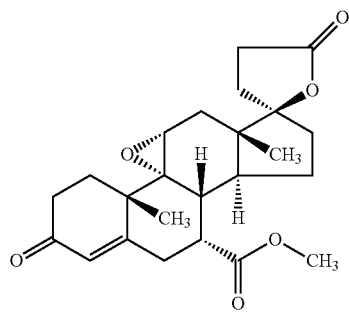

or spironolactone; or, in each case, if appropriable, a pharmaceutically acceptable salt thereof.

Aldosterone synthase inhibitors useful in said combination are compounds and analogs generically and specifically disclosed e.g. in US2007/0049616, in particular in the compound claims and the final products of the working examples, the subject-matter of the final products, the pharmaceutical preparations and the claims are hereby incorporated into the present application by reference to this publication. Preferred aldosterone synthase inhibitors suitable for use in the present disclosure include, without limitation 4-(6,7-dihydro-5H-pyrrolo[1,2-c]imidazol-5-yl)-3-methyl-benzonitrile; 5-(2-chloro-4-cyanophenyl)-6,7-dihydro-5H-pyrrolo[1,2-c]imidazole-5-carboxylic acid (4-methoxybenzyl)methylamide; 4'-fluoro-6-(6,7,8,9-tetrahydro-5H-imidazo[1,5-a]azepin-5-yl)biphenyl-3-carbonitrile; 5-(4-Cyano-2-methoxyphenyl)-6,7-dihydro-5H-pyrrolo[1,2-c] imidazole-5-carboxylic acid butyl ester; 4-(6,7-Dihydro-5H-pyrrolo[1,2-c]imidazol-5-yl)-2-methoxybenzonitrile; 5-(2-Chloro-4-cyanophenyl)-6,7-dihydro-5H-pyrrolo[1,2-c]imidazole-5-carboxylic acid 4-fluorobenzyl ester; 5-(4-Cyano-2-trifluoromethoxyphenyl)-6,7-dihydro-5H-pyrrolo[1,2-c]imidazole-5-carboxylic acid methyl ester; 5-(4-Cyano-2-methoxyphenyl)-6,7-dihydro-5H-pyrrolo[1,2-c]imidazole-5-carboxylic acid 2-isopropoxyethyl ester; 4-(6,7-Dihydro-5H-pyrrolo[1,2-c]imidazol-5-yl)-2-methylbenzonitrile; 4-(6,7-dihydro-5H-pyrrolo[1,2-c]imidazol-5-yl)-3-fluorobenzonitrile; 4-(6,7-Dihydro-5H-pyrrolo[1,2-c]imidazol-5-yl)-2-methoxybenzonitrile; 3-Fluoro-4-(7-methylene-6,7-dihydro-5H-pyrrolo[1,2-c]imidazol-5-yl)benzonitrile; cis-3-Fluoro-4-[7-(4-fluorobenzyl)-5,6,7,8-tetrahydro-imidazo[1,5-a]pyridin-5-yl]benzonitrile; 4'-Fluoro-6-(9-methyl-6,7,8,9-tetrahydro-5H-imidazo[1,5-a]azepin-5-yl)biphenyl-3-carbonitrile; 4'-Fluoro-6-(9-methyl-6,7,8,9-tetrahydro-5H-imidazo[1,5-a]azepin-5-yl)biphenyl-3-carbonitrile or in each case, the (R) or (S) enantiomer thereof; or if appropriable, a pharmaceutically acceptable salt thereof.

The term aldosterone synthase inhibitors also include compounds and analogs disclosed in WO2008/076860, WO2008/076336, WO2008/076862, WO2008/027284, WO2004/046145, WO2004/014914, WO2001/076574.

Furthermore aldosterone synthase inhibitors also include compounds and analogs disclosed in U.S. patent applications US2007/0225232, US2007/0208035, US2008/0318978, US2008/0076794, US2009/0012068, US20090048241 and in PCT applications WO2006/005726, WO2006/128853, WO2006128851, WO2006/128852, WO2007065942, WO2007/116099, WO2007/116908, WO2008/119744 and in European patent application EP 1886695. Preferred aldosterone synthase inhibitors suitable for use in the present disclosure include, without limitation 8-(4-Fluorophenyl)-5,6-dihydro-8H-imidazo[5,1-c][1,4]oxazine; 4-(5,6-Dihydro-8H-imidazo[5,1-c][1,4]oxazin-8-yl)-2-fluorobenzonitrile; 4-(5,6-Dihydro-8H-imidazo[5,1-c][1,4]oxazin-8-yl)-2,6-difluorobenzonitrile; 4-(5,6-Dihydro-8H-imidazo[5,1-c][1,4]oxazin-8-yl)-2-methoxybenzonitrile; 3-(5,6-Dihydro-8H-imidazo[5,1-c][1,4]oxazin-8-yl)benzonitrile; 4-(5,6-Dihvdro-8H-imidazo[5,1-c][1,4]oxazin-8-yl)phthalonitrile; 4-(8-(4-Cyanophenyl)-5,6-dihydro-8H-imidazo[5,1-c][1,4]oxazin-8-yl) benzonitrile; 4-(5,6-Dihydro-8H-imidazo[5,1-c][1,4]oxazin-8-yl)benzonitrile; 4-(5,6-Dihydro-8H-imidazo[5,1-c][1,4]oxazin-8-yl)naphthalene-1-carbonitrile; 8-[4-(1H-Tetrazol-5-yl)phenyl-1,5,6-dihvdro-8H-imidazo[5,1-c][1,4]oxazine as developed by Speedel or in each case, the (R) or (S) enantiomer thereof; or if appropriable, a pharmaceutically acceptable salt thereof.

Aldosterone synthase inhibitors useful in said combination are compounds and analogs generically and specifically disclosed e.g. in WO 2009/156462 and WO 2010/130796, in particular in the compound claims and the final products of the working examples, the subject-matter of the final products, the pharmaceutical preparations and the claims.

Preferred aldosterone synthase inhibitors suitable for combination in the present disclosure include, 3-(6-Fluoro-3-methyl-2-pyridin-3-yl-1H-indol-1-ylmethyl)-benzonitrile hydrochloride, 1-(4-Methanesulfonyl-benzyl)-3-methyl-2-pyridin-3-yl-1H-indole, 2-(5-Benzyloxy-pyridin-3-yl)-6- chloro-1-methyl-1H-indole, 5-(3-Cyano-1-methyl-1H-indol-2-yl)-nicotinic acid ethyl ester, N-[5-(6-chloro-3-cyano-1-methyl-1H-indol-2-yl)-pyridin-3-ylmethyl]-ethanesulfonamide, Pyrrolidine-1-sulfonic acid 5-(6-chloro-3-cyano-1-methyl-1H-indol-2-yl)-pyridin-3-yl ester, N-Methyl-N-[5-(1-methyl-1H-indol-2-yl)-pyridin-3-ylmethyl]-methanesulfonamide, 6-Chloro-1-methyl-2-{5-[(2-pyrrolidin-1-yl-ethylamino)-methyl]-pyridin-3-yl}-1H-indole-3-carbonitrile, 6-Chloro-2-[5-(4-methanesulfonyl-piperazin-1-ylmethyl)-pyridin-3-yl]-1-methyl-1H-indole-3-carbonitrile, 6-Chloro-1-methyl-2-{5-[(1-methyl-piperidin-4-ylamino)-methyl]-pyridin-3-yl}-1H-indole-3-carbonitrile, Morpholine-4-carboxylic acid [5-(6-chloro-3-cyano-1-methyl-1H-indol-2-yl)-pyridin-3-ylmethyl]-amide, N-[5-(6-Chloro-1-methyl-1H-indol-2-yl)-pyridin-3-ylmethyl]-ethanesulfonamide, C,C,C-Trifluoro-N-[5-(1-methyl-1H-indol-2-yl)-pyridin-3-ylmethyl]-methanesulfonamide, N-[5-(3-Chloro-4-cyano-phenyl)-pyridin-3-yl]-4-trifluoromethyl-benzenesulfonamide, N-[5-(3-Chloro-4-cyano-phenyl)-pyridin-3-yl]-1-phenyl-methanesulfonamide, N-(5-(3-chloro-4-cyanophenyl)pyridin-3-yl)butane-1-sulfonamide, N-(1-(5-(4-cyano-3-methoxyphenyl)pyridin-3-yl)ethyl)ethanesulfonamide, N-((5-(3-chloro-4-cyanophenyl)pyridin-3-yl) (cyclopropyl)methyl)ethanesulfonamide, N-(cyclopropyl(5-(1H-indol-5-yl)pyridin-3-yl)methyl) ethanesulfonamide, N-(cyclopropyl(5-naphtalen-1-yl-pyridin-3-yl)methyl)ethanesulfonamide, Ethanesulfonic acid [5-(6-chloro-1-methyl-1H-pyrrolo[2,3-b]pyridin-2-yl)-pyridin-3-ylmethyl]-amide and Ethanesulfonic acid {[5-(3-chloro-4-cyano-phenyl)-pyridin-3-yl]-cyclopropyl-methyl}-ethyl-amide.

The term "endothelin receptor blocker" includes bosentan.

The term "CETP inhibitor" refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). Examples include compounds disclosed in U.S. Pat. Nos. 6,140,343 and 6,197,786 (e.g., [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib); compounds disclosed in U.S. Pat. No. 6,723,752 (e.g., (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol); compounds disclosed in U.S. patent application Ser. No. 10/807,838; polypeptide derivatives disclosed in U.S. Pat. No. 5,512,548; rosenonolactone derivatives and phosphate-containing analogs of cholesteryl ester disclosed in *J. Antibiot.*, 49(8): 815-816 (1996), and *Bioorg. Med. Chem. Lett.*; 6:1951-1954 (1996), respectively. Furthermore, the CETP inhibitors also include those disclosed in WO2000/017165, WO2005/095409 and WO2005/097806.

CETP inhibitors useful in said combination are compounds and analogs generically and specifically disclosed e.g. in WO 2008/009435, WO 2009/059943 and WO 2009/071509, in particular in the compound claims and the final products of the working examples, the subject-matter of the final products, the pharmaceutical preparations and the claims.

Examples of phophodiesterase type 5 (PDE5) inhibitors are sildenafil, avanafil, iodenafil, mirodenafil, tadalafil, vardenafil and udenafil.

Second agent of particular interest include endothelin antagonists, renin inhibitors, angiotensin II receptor antagonists, phophodiesterase type 5 (PDE5) inhibitors calcium channel blockers, diuretics, antidiabetic agents such as DPPIV inhibitors, and aldosterone synthase inhibitors.

In one embodiment, the disclosure provides a combination, in particular a pharmaceutical combination, comprising a therapeutically effective amount of the compound according to the definition of Formula (I) or (II), or a pharmaceutically acceptable salt, hydrate, solvate, prodrug, stereoisomer, or tautomer thereof, and one or more therapeutically active agents selected from HMG-Co-A reductase inhibitors, angiotensin II receptor antagonists, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI), CETP inhibitors and phophodiesterase type 5 (PDE5) inhibitor.

In one embodiment, the disclosure provides a method of inhibiting neutral endopeptidase activity in a subject, wherein the method comprises administering to the subject a therapeutically effective amount of the compound according to the definition of Formula (I) or (II), or a pharmaceutically acceptable salt, hydrate, solvate, prodrug, stereoisomer, or tautomer thereof.

In one embodiment, the disclosure provides a method of treating a disorder or a disease in a subject associated with neutral endopeptidase activity, wherein the method comprises administering to the subject a therapeutically effective amount of the compound according to the definition of Formula (I) or (II), or a pharmaceutically acceptable salt, hydrate, solvate, prodrug, stereoisomer, or tautomer thereof.

In one embodiment, the disclosure provides a compound of Formula (I) or (II), or a pharmaceutically acceptable salt, hydrate, solvate, prodrug, stereoisomer, or tautomer thereof, or a composition comprising a compound of Formula (I) or (II), or a pharmaceutically acceptable salt, hydrate, solvate, prodrug, stereoisomer, or tautomer thereof, and one or more pharmaceutically acceptable carriers for use as a medicament.

In one embodiment, the disclosure provides a compound of Formula (I) or (II), or a pharmaceutically acceptable salt, hydrate, solvate, prodrug, stereoisomer, or tautomer thereof, or a composition comprising a compound of Formula (I) or (II), or a pharmaceutically acceptable salt, hydrate, solvate, prodrug, stereoisomer, or tautomer thereof, and one or more pharmaceutically acceptable carriers for use in the treatment of a disorder or disease associated with neutral endopeptidase activity.

In one embodiment, the disclosure provides a compound of Formula (I) or (II), or a pharmaceutically acceptable salt, hydrate, solvate, prodrug, stereoisomer, or tautomer thereof, or a composition comprising a compound of Formula (I) or (II), or a pharmaceutically acceptable salt, hydrate, solvate, prodrug, stereoisomer, or tautomer thereof, and one or more pharmaceutically acceptable carriers for use in the treatment of a disorder or disease selected from hypertension, resistant hypertension, pulmonary heart disease, pulmonary hypertension, pulmonary arterial hypertension, isolated systolic hypertension, peripheral vascular disease, heart failure, heart failure with preserved ejection fraction (HF-PEF), heart failure with reduced ejection fraction (HF-REF), mitral stenosis and regurgitation, left ventricular hypertrophy, angina, renal insufficiency, renal failure, diabetic nephropathy, non-diabetic nephropathy, contrast-induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, cardiomyopathy, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, myocardial infarction (MI), renal fibrosis, polycystic kidney disease (PKD), renal failure, cyclical oedema, Menière's disease, hyperaldosteronism, hypercalciuria, ascites, glaucoma, menstrual disorders, preterm labor, pre-eclampsia, endometriosis, and reproductive disorders, asthma, obstructive sleep apnea, inflammation, leukemia, pain, epilepsy, affective disorders, depression, psychotic condition, obesity, gastrointestinal disorders, wound healing, septic shock, gastric acid secretion dysfunction, hyperreninemia, cystic fibrosis, restenosis, type-2 diabetes, metabolic syndrome, diabetic complications, atherosclerosis, and male and female sexual dysfunction.

In another embodiment, the compounds of the disclosure are for use in the treatment of a disorder or disease selected from hypertension, pulmonary hypertension, isolated systolic hypertension, resistant hypertension, peripheral vascular disease, heart failure, heart failure with preserved ejection fraction (HF-PEF), heart failure with reduced ejection fraction (HF-REF), or pulmonary arterial hypertension. In a preferred embodiment the compounds of the disclosure are useful in the treatment of cardiovascular disorders. In one embodiment, the disclosure provides the use of a compound of Formula (I) or (II), or a pharmaceutically acceptable salt, hydrate, solvate, prodrug, stereoisomer, or tautomer thereof, or a composition comprising a compound of Formula (I) or (II), or a pharmaceutically acceptable salt, hydrate, solvate, prodrug, stereoisomer, or tautomer thereof, and one or more pharmaceutically acceptable carriers for the treatment of a disorder or disease in a subject associated with neutral endopeptidase activity.

In some embodiments, the disorder or the disease is selected from hypertension, resistant hypertension, pulmonary heart disease, pulmonary hypertension, pulmonary arterial hypertension, isolated systolic hypertension, peripheral vascular disease, heart failure, heart failure with preserved ejection fraction (HF-PEF), heart failure with reduced ejection fraction (HF-REF), mitral stenosis and regurgitation, left ventricular hypertrophy, angina, renal insufficiency, renal failure, diabetic nephropathy, non-diabetic nephropathy, contrast-induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, cardiomyopathy, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, myocardial infarction (MI), renal fibrosis, polycystic kidney disease (PKD), renal failure, cyclical oedema, Menière's disease, hyperaldosteronism, hypercalciuria, ascites, glaucoma, menstrual disorders, preterm labor, preeclampsia, endometriosis, and reproductive disorders, asthma, obstructive sleep apnea, inflammation, leukemia, pain, epilepsy, affective disorders, depression, psychotic condition, obesity, gastrointestinal disorders, wound healing, septic shock, gastric acid secretion dysfunction, hyperreninemia, cystic fibrosis, restenosis, type-2 diabetes, metabolic syndrome, diabetic complications, atherosclerosis, and male and female sexual dysfunction.

In another embodiment, the compounds of the disclosure are useful in the treatment of a disorder or disease selected from hypertension, pulmonary hypertension, isolated systolic hypertension, resistant hypertension, peripheral vascular disease, heart failure, heart failure with preserved ejection fraction (HF-PEF), heart failure with reduced ejection fraction (HF-REF), or pulmonary arterial hypertension. In a preferred embodiment the compounds of the disclosure are useful in the treatment of cardiovascular disorders.

In one embodiment, the disclosure provides a method of treating a disorder or a disease in a subject associated with neutral endopeptidase activity, wherein the disorder or the disease is selected from hypertension, pulmonary heart disease, pulmonary hypertension, pulmonary arterial hypertension, isolated systolic hypertension, resistant hypertension, peripheral vascular disease, heart failure, heart failure with preserved ejection fraction (HF-PEF), heart failure with reduced ejection fraction (HF-REF), mitral stenosis and regurgitation, left ventricular hypertrophy, angina, renal insufficiency (diabetic or non-diabetic), renal failure (including edema and salt retention), diabetic nephropathy, non-diabetic nephropathy, contrast induced nephropathy, nephrotic syndrome, glomerulonephritis, scleroderma, glomerular sclerosis, proteinurea of primary renal disease, renal vascular hypertension, diabetic retinopathy and end-stage renal disease (ESRD), endothelial dysfunction, diastolic dysfunction, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, myocardial infarction (MI), renal fibrosis, polycystic kidney disease (PKD), renal failure (including edema and salt retention), cyclical oedema, Menière's disease, hyperaldosteronism (primary and secondary), hypercalciuria, ascites, glaucoma, menstrual disorders, preterm labor, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression, obesity and gastrointestinal disorders (especially diarrhea and irritable bowel syndrome), wound healing (especially diabetic and venous ulcers and pressure sores), septic shock, gastric acid secretion dysfunction, hyperreninemia, cystic fibrosis, restenosis, type-2 diabetes, metabolic syndrome, diabetic complications, atherosclerosis and male and female sexual dysfunction. In yet another embodiment, the disclosure provides a method of treating a disorder or a disease in a subject associated with neutral endopeptidase activity, wherein the disorder or the disease is selected from hypertension, pulmonary heart disease, pulmonary hypertension, isolated systolic hypertension, resistant hypertension, peripheral vascular disease, heart failure, heart failure with preserved ejection fraction (HF-PEF), heart failure with reduced ejection fraction (HF-REF), mitral stenosis and regurgitation, and pulmonary arterial hypertension.

In one embodiment, the disclosure provides the use of a compound of Formula (I) or (II), or a pharmaceutically acceptable salt, hydrate, solvate, prodrug, stereoisomer, or tautomer thereof, or a composition comprising a compound of Formula (I) or (II), or a pharmaceutically acceptable salt, hydrate, solvate, prodrug, stereoisomer, or tautomer thereof, and one or more pharmaceutically acceptable carriers in the manufacture of a medicament for the treatment of a disorder or disease in a subject characterized by an activity of neutral endopeptidase, wherein said disorder or disease is in particular selected from hypertension, pulmonary heart disease, pulmonary hypertension, pulmonary arterial hypertension, isolated systolic hypertension, resistant hypertension, peripheral vascular disease, heart failure, heart failure with preserved ejection fraction (HF-PEF), heart failure with reduced ejection fraction (HF-REF), mitral stenosis and regurgitation, left ventricular hypertrophy, angina, renal insufficiency (diabetic or non-diabetic), renal failure (including edema and salt retention), diabetic nephropathy, non-diabetic nephropathy, contrast induced nephropathy, nephrotic syndrome, glomerulonephritis, scleroderma, glomerular sclerosis, proteinurea of primary renal disease, renal vascular hypertension, diabetic retinopathy and end-stage renal disease (ESRD), endothelial dysfunction, diastolic dysfunction, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, myocardial infarction (MI), renal fibrosis, polycystic kidney disease (PKD), renal failure (including edema and salt retention), cyclical oedema, Menière's disease, hyperaldosteronism (primary and secondary), hypercalciuria, ascites, glaucoma, menstrual disorders, pre-term labor, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression, obesity and gastrointestinal disorders (especially diarrhea and irritable bowel syndrome), wound healing (especially diabetic and venous ulcers and pressure sores), septic shock, gastric acid secretion dysfunction, hyperreninemia, cystic fibrosis, restenosis, type-2 diabetes, metabolic syndrome, diabetic complications, atherosclerosis, and male and female sexual dysfunction. In another embodiment, the disorder or disease is in particular selected hypertension, pulmonary heart disease, pulmonary hypertension, isolated systolic hypertension, resistant hypertension, peripheral vascular disease, heart failure, heart failure with preserved ejection fraction (HF-PEF), heart failure with reduced ejection fraction (HF-REF), mitral stenosis and regurgitation, and pulmonary arterial hypertension.

In one embodiment, the disclosure provides the use of a compound of Formula (I) or (II), or a pharmaceutically acceptable salt, hydrate, solvate, prodrug, stereoisomer, or tautomer thereof, or a composition comprising a compound of Formula (I) or (II), or a pharmaceutically acceptable salt, hydrate, solvate, prodrug, stereoisomer, or tautomer thereof, and one or more pharmaceutically acceptable carriers for the treatment of a disorder or disease in a subject characterized by an activity of neutral endopeptidase, wherein the disorder or disease is selected from hypertension, pulmonary heart disease, pulmonary hypertension, pulmonary arterial hypertension, isolated systolic hypertension, resistant hypertension, peripheral vascular disease, heart failure, heart failure with preserved ejection fraction (HF-PEF), heart failure with reduced ejection fraction (HF-REF), mitral stenosis and regurgitation, left ventricular hypertrophy, angina, renal insufficiency (diabetic or non-diabetic), renal failure (including edema and salt retention), diabetic nephropathy, non-diabetic nephropathy, contrast induced nephropathy, nephrotic syndrome, glomerulonephritis, scleroderma, glomerular sclerosis, proteinurea of primary renal disease, renal vascular hypertension, diabetic retinopathy and end-stage renal disease (ESRD), endothelial dysfunction, diastolic dysfunction, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, myocardial infarction (MI), renal fibrosis, polycystic kidney disease (PKD), renal failure (including edema and salt retention), cyclical oedema, Menière's disease, hyperaldosteronism (primary and secondary), hypercalciuria, ascites, glaucoma, menstrual disorders, pre-term labor, pre-eclampsia, endometriosis, reproductive disorders (especially male and female infertility, polycystic ovarian syndrome, implantation failure), asthma, obstructive sleep apnea, inflammation, leukemia, pain, epilepsy, affective disorders such as depression, obesity and gastrointestinal disorders (especially diarrhea and irritable bowel syndrome), wound healing (especially diabetic and venous ulcers and pressure sores), septic shock, gastric acid secretion dysfunction, hyperreninemia, cystic fibrosis, restenosis, type-2 diabetes, metabolic syndrome, diabetic complications, atherosclerosis, and male and female sexual dysfunction, and more particularly the disease or disorder is selected from hypertension, pulmonary heart disease, pulmonary hypertension, isolated systolic hypertension, resistant hypertension, peripheral vascular disease, heart failure, heart failure with preserved ejection fraction (HF-PEF), heart failure with reduced ejection fraction (HF-REF), mitral stenosis and regurgitation, and pulmonary arterial hypertension.

In some embodiments, of the methods and uses above the compound of Formula (I) or (II), or a pharmaceutically acceptable salt, hydrate, solvate, prodrug, stereoisomer, or tautomer thereof, or the composition comprising a compound of Formula (I) or (II), or a pharmaceutically acceptable salt, hydrate, solvate, prodrug, stereoisomer, or tautomer thereof, and one or more pharmaceutically acceptable carriers is administered to or used with patients already or concomitantly being treated with an Angiotensin Receptor Blocker. In one embodiment, the Angiotensin Receptor Blocker is selected from valsartan, candesartan, losartan, irbesartan, telmisartan, olmesartan, eprosartan, fimasartan, and azilsartan, or a pharmaceutically acceptable salt thereof. In another embodiment, the Angiotensin Receptor Blocker is valsartan, or a pharmaceutically acceptable salt thereof.

In one embodiment, the compound or the composition is administered or used together with the Angiotensin Receptor Blocker or a pharmaceutically acceptable salt thereof. In another embodiment, the compound or the composition is administered or used concomitantly with the Angiotensin Receptor Blocker or a pharmaceutically acceptable salt thereof. In yet another embodiment, the compound or the composition is administered or used sequentially with the Angiotensin Receptor Blocker or a pharmaceutically acceptable salt thereof. In one embodiment, the Angiotensin Receptor Blocker is selected from valsartan, candesartan, losartan, irbesartan, telmisartan, olmesartan, eprosartan, fimasartan, and azilsartan, or a pharmaceutically acceptable salt thereof. In another embodiment, the Angiotensin Receptor Blocker is valsartan, or a pharmaceutically acceptable salt thereof.

Pharmaceutical Compositions

In another aspect, the present disclosure provides a pharmaceutical composition comprising a compound of the present disclosure or a pharmaceutically acceptable salt thereof and one or more pharmaceutically acceptable carriers. The pharmaceutical composition can be Formulated for particular routes of administration such as oral administration, parenteral administration, and rectal administration, etc. In addition, the pharmaceutical compositions of the present disclosure can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners. Tablets may be either film coated or enteric coated according to methods known in the art.

Suitable compositions for oral administration include an effective amount of a compound of the disclosure in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the disclosure with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable Formulations, e.g., for delivery by aerosol or the like. Such topical delivery systems will in particular be appropriate for dermal application. They are thus particularly suited for use in topical, including cosmetic, Formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present disclosure further provides anhydrous pharmaceutical compositions and dosage forms comprising the compounds of the present disclosure as active ingredients, since water may facilitate the degradation of certain compounds.

Anhydrous pharmaceutical compositions and dosage forms of the disclosure can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable Formulary kits. Examples of suitable packaging include, but are not limited to, hermetically sealed foils, plastics, unit dose containers (e. g., vials), blister packs, and strip packs.

The disclosure further provides pharmaceutical compositions and dosage forms that comprise one or more agents that reduce the rate by which the compound of the present disclosure as an active ingredient will decompose. Such agents, which are referred to herein as "stabilizers" include, but are not limited to, antioxidants such as ascorbic acid, pH buffers, or salt buffers, etc.

The compounds according to Formula (I) or (II), or a pharmaceutically acceptable salt thereof, in free form or in pharmaceutically acceptable salt form, exhibit valuable pharmacological properties, e.g. neutral endopeptidase modulating properties, e.g. as indicated in in vitro and in vivo tests as provided in the next sections and are therefore indicated for therapy.

The pharmaceutical composition or combination of the present disclosure can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, are dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present disclosure can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present disclosure can be assessed by the following in vitro and in vivo methods and/or by the following in vitro and in vivo methods well-described in the art. See Doering, K., Meder G., Hinnenberger, M., Woelcke, J., Mayr, L. M., Hassiepen, U., (2009) "A fluorescence lifetime-based assay for protease inhibitor profiling on human kallikrein 7", Biomol. Screen, January; 14(1):1-9.

The compound of the present disclosure may be administered either simultaneously with, or before or after, one or more other therapeutic agents. The compound of the present disclosure may be administered separately, by the same or different route of administration, or together in the same pharmaceutical composition as the other agents.

Exemplification of the Disclosure:

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

All starting materials, building blocks, reagents, acids, bases, dehydrating agents, solvents, and catalysts utilized to synthesize the compounds of the present disclosure are either commercially available or can be produced by organic synthesis methods known to one of ordinary skill in the art (Houben-Weyl 4th Ed. 1952, Methods of Organic Synthesis, Thieme, Volume 21). Further, the compounds of the present disclosure can be produced by organic synthesis methods known to one of ordinary skill in the art as shown in the following examples.

Compounds of the present disclosure may be prepared by methods known in the art of organic synthesis. In all of the methods it is understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, 3rd edition, John Wiley & Sons). These groups are removed at a convenient stage of the compound synthesis using methods that are readily apparent to those skilled in the art.

Analytical Methods, Materials, and Instrumentation

Unless otherwise noted, reagents and solvents were used as received from commercial suppliers. Proton nuclear magnetic resonance (NMR) spectra were obtained on either Bruker Avance spectrometer or Varian Oxford 400 MHz spectrometer unless otherwise noted. Spectra are given in ppm ($\delta$) and coupling constants, J, are reported in Hertz. Tetramethylsilane (TMS) was used as an internal standard. Chemical shifts are reported in ppm relative to dimethyl sulfoxide ($\delta$2.50), methanol ($\delta$3.31), chloroform ($\delta$7.26) or other solvent as indicated in NMR spectral data. A small amount of the dry sample (2-5 mg) is dissolved in an appropriate deuterated solvent (1 mL). The chemical names were generated using ChemBioDraw Ultra v12 from CambridgeSoft. The following examples are intended to illustrate the disclosure and are not to be construed as being limitations thereon.

Temperatures are given in degrees centigrade. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

XRPD

XRPD measurements were performed using a Bruker D8 Discover X-ray diffractometer (Bruker AXS Inc., Madison, Wis., USA) with CuK$\alpha$ radiation of 1.5418 Å, acceleration voltage and current of 45 kV and 45 µA, respectively. The samples were scanned in reflectance mode between 3° and 45° 2$\theta$. The data was collected and analyzed using Bruker EVA v.13.0.0.3 software (Bruker AXS Inc., Madison, Wis., USA).

DSC

DSC thermograms were obtained with DSC Q2000 (TA Instruments, USA). Sample powders (1 to 2 mg) were crimped in a standard aluminum pan. An empty sample pan is used as reference. The DSC thermogram is recorded as follow: the sample was equilibrated at 30° C., and heated to 300° C. at a heating rate of 10° C./min, under a nitrogen flow of 50 mL/min. No equilibration was applied to I-2 Crystalline Form A and Form B. The instrument is calibrated for temperature and enthalpy with Indium, at least 99.9999% pure. The accuracy of the measured sample temperature with this method is within about ±1° C., and the heat of fusion can be measured within a relative error of about ±5%.

TGA

TGA thermograms were obtained with TGA Q5000 (TA Instruments, USA). Sample powder (1 to 2 mg) was loaded into a pre-tared standard aluminum pan. The TGA thermogram was recorded as follows: the sample was loaded into the furnace, equilibrated to 30° C. and heated to 300° C. at a heating rate of 10° C./min, under a flow of nitrogen at 25 mL/min. No equilibration was applied to I-2 Crystalline Form A and Form B. The instrument is calibrated for temperature with nickel and aluminum, and calibrated for weight with a 100 mg standard.

The following examples are intended to illustrate the disclosure and are not to be construed as being limitations thereon.

Abbreviations used in the following examples and elsewhere herein are:

Å: Ångström
ACN: acetonitrile
br: broad
bs: broad singlet
dd: doublet of doublets
DCM: dichloromethane
DMF: dimethylformamide
DMSO: dimethylsulfoxide EDC HCl: ethyl(dimethylaminopropyl)carbodiimide hydrochloride
EDTA: Ethylenediaminetetraacetic Acid
ee: enantiomeric excess
ES: electrospray
ES-API: electrospray-atmospheric pressure ionization
EtOAc: ethyl acetate
h: Hour(s)
HPC: hydroxypropyl cellulose
HPLC: high pressure liquid chromatography
HPLC-RT: high pressure liquid chromatography retention time
IPA iso-propyl alcohol
iPrOAc: iso-propyl acetate
ISTD: internal standard
L: liter
LCMS: liquid chromatography and mass spectrometry
Lys-(Boc)-Ot-Bu: tert-butyl $N^6$-(tert-butoxycarbonyl)-L-lysinate
m: multiplet
MeCN: acetonitrile
MTBE: Methyl tert-butyl ether
mg: milligram
min: minutes
μL: microlitre
mL: millilitre
M: molar
mM: millimole(s)
MS: mass spectrometry
m/z: mass to charge ratio
NMR: nuclear magnetic resonance
PO: oral administration
q: quartet
QD: once per day
ROI residue on ignition
RT: room temperature
s: singlet
Sac-Lys-Boc-Bu Ethyl (10S,17S,19R)-17-([1,1'-biphenyl]-4-ylmethyl)-10-(tert-butoxycarbonyl)-2,2,19-trimethyl-4,12,15-trioxo-3-oxa-5,11,16-triazaicosan-20-oate
Sac-OSu: Sacubitril-Hydroxysuccinamide ester
t: triplet
TBME: methyl tert-butyl ether
TFA: trifluoroacetic acid
THF: tetrahydrofuran Example 1: Synthesis of (4-(((2S,4R)-1-([1,1'-biphenyl]-4-yl)-5-ethoxy-4-methyl-5-oxopentan-2-yl)amino)-4-oxobutanoyl)-L-leucine (I-1)

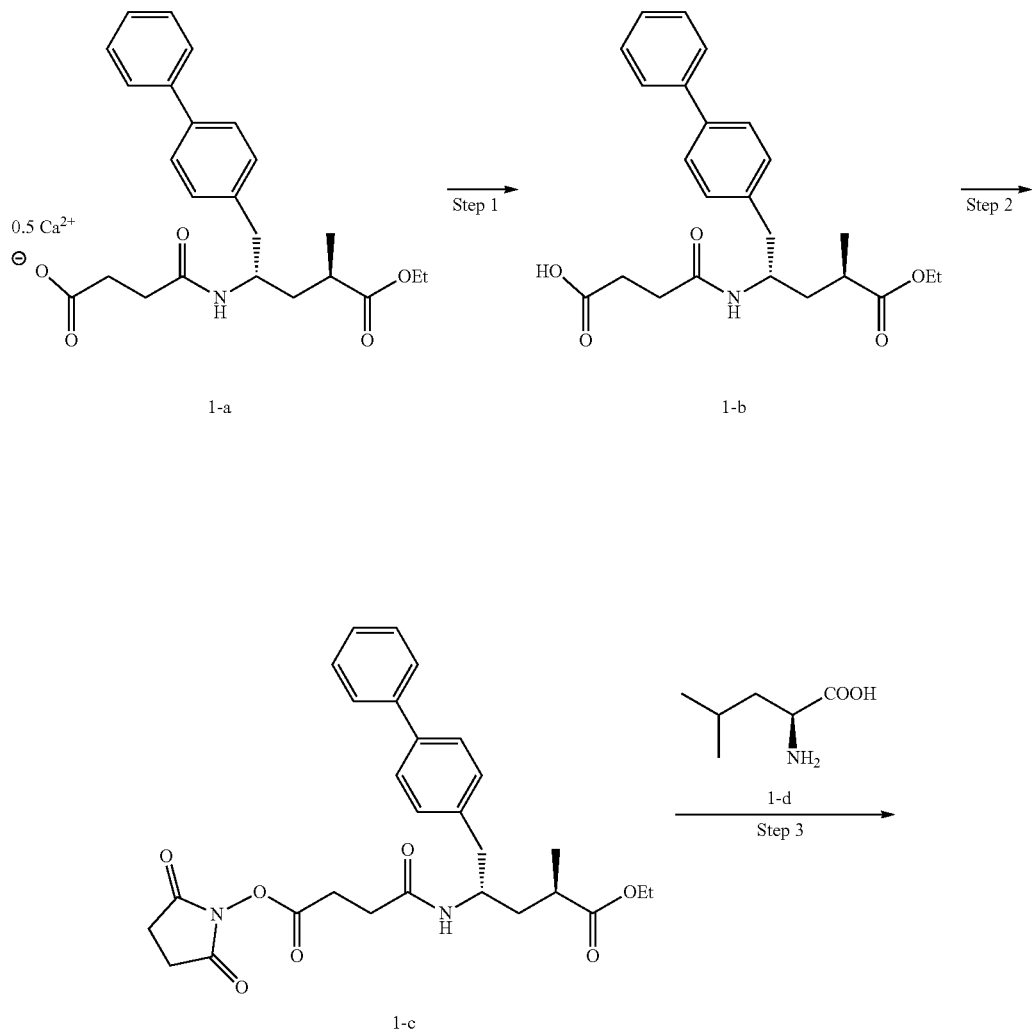

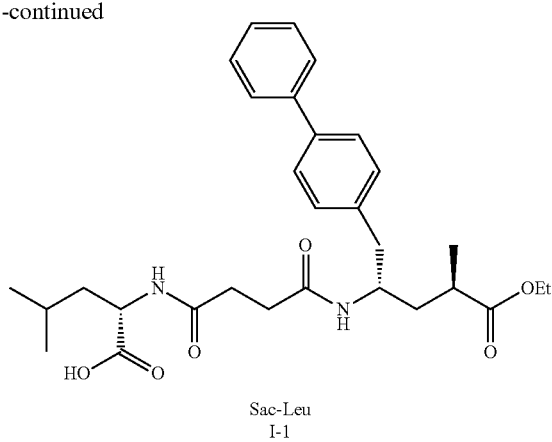

Sac-Leu
I-1

Step 1: 4-(((2S,4R)-1-([1,1'-biphenyl]-4-yl)-5-ethoxy-4-methyl-5-oxopentan-2-yl)amino)-4-oxobutanoic acid (Sacubitril) (1-b)

To a suspension of sacubitril calcium salt (1-a, 90 g, 232.2 mmol) in iPrOAc (900 mL) cooled to 10-15° C. was added aq. 2N HCl solution (218.5 mL); (observed slightly exothermicity) and the resulting reaction mixture was stirred for an additional 40 min. Once HPLC indicated 93.99% product formation and complete consumption of starting material the organic layer was separated and washed with water (2×180 mL). The organic layer was then dried over anhydrous $Na_2SO_4$, filtered, and concentrated under reduced pressure at 50° C. The remaining solution was stripped off with THF (180 mL×3), which afforded sacubitril (1-b, 92 g, 98.8%). HPLC purity: 99.65% and $^1$H NMR (δ, ppm, DMSO-$d_6$): 12.0 (1H, bs), 7.8 (1H, d), 7.7 (2H, d), 7.6 (2H, d), 7.4-7.5 (2H, t), 7.3-7.4 (1H, t), 7.2-7.3 (2H, d), 4.0 (2H, q), 2.6-2.8 (2H, m), 2.2-2.4 (4H, m), 1.7-1.8 (1H, m), 1.3-1.4 (1H, m), 1.0-1.2 (8H, m).

Step 2: Ethyl (2R,4S)-5-([1,1'-biphenyl]-4-yl)-4-(4-((2,5-dioxopyrrolidin-1-yl)oxy)-4-oxobutanamido)-2-methylpentanoate (1-c)

To a mixture of 1-b (71 g, 172.5 mmol) and hydroxysuccinamide (39.71, 345 mmol) in DMF (461.5 mL), was added EDC HCl (66.14 g, 345 mmol) at ambient temperature. The resulting clear solution was stirred for 20 h at RT. Once HPLC indicated 5.51% starting material and 81.1% product formation, the reaction was quenched with water (1065 mL) at 5-10° C., and then stirred at ambient temperature for an additional 1 h. The resulting solid was filtered and washed with water (2×210 mL). The crude material was dissolved in EtOAc (560 mL), n-heptane (1120 mL) was then added, and the resulting mixture was stirred at ambient temperature for 1 h. The resulting white solid was collected by filtration and washed with n-heptane, to afford Sac-OSu 1-c (75.8 g, 86.4%) as a white solid. HPLC purity: 95.97% and $^1$H NMR (δ, ppm, DMSO-$d_6$): 7.9 (1H, d), 7.6-7.7 (4H, m), 7.5 (2H, t), 7.35 (1H, t), 7.25 (2H, d), 3.9-4.0 (3H, m), 2.8-2.9 (8H, m), 2.4-2.5 (3H, m), 1.8 (1H, m), 1.4 (1H, m), 1.1 (3H, t), 1.0 (3H, d). LCMS: 96.73% ([M+1]=508.9).

Step 3: Ethyl (2R,4S)-5-([1,1'-biphenyl]-4-yl)-4-(4-((2,5-dioxopyrrolidin-1-yl)oxy)-4-oxobutanamido)-2-methylpentanoate (I-1)

To a solution of Sac-OSu (1-c, 12 g, 23.5 mmol) in THF (96 mL) was added L-leucine (I-d, 3.71 g, 28.3 mmol) and sodium bicarbonate (3.94 g, 4.7 mmol) followed by water (48 mL) at ambient temperature. The resulting reaction mixture was then stirred at ambient temperature for 3 h. Once HPLC indicated complete consumption of starting material and 92.41% product, the solvent was evaporated under reduced pressure at 50° C., 1N aq. HCl (120 mL) was then added and the resulting aqueous solution was extracted with EtOAc (5×60 mL). The combined organic layers were washed with water (60 mL and brine (60 mL), dried over anhydrous $Na_2SO_4$, filtered, and concentrated under reduced pressure at 50° C. The crude product was purified by dissolving in iPrOAc (120 mL), adding hexanes (240 mL), and then stirring the resulting mixture at ambient temperature for 1 h. The resulting solid was collected by filtration and washed with hexanes (60 mL) to afford 9.5 g of (I-1) with 97.84% purity. To achieve higher purity, the same purification procedure was repeated, to afford sacubitril leucine I-1 (7.4 g, 60%) with 99.06% purity as a white solid. HPLC purity: 99.06% and $^1$H NMR (δ, ppm, DMSO-$d_6$): 12.5 (1H, bs), 8.1 (1H, d), 7.8 (1H, d), 7.7 (2H, d), 7.6 (2H, d), 7.45 (2H, t), 7.3-7.4 (1H, t), 7.25 (2H, d), 4.2-4.3 (1H, q), 3.9-4.05 (3H, m), 2.6-2.8 (2H, m), 2.2-2.4 (4H, m), 1.75-1.85 (1H, m), 1.6-1.7 (1H, m), 1.3-1.5 (4H, m), 1.05-1.15 (6H, m), 0.8-0.9 (6H, dd). LCMS: 99.64% 525.1 ([M+1]=525.1).

Example 1A: Synthesis of Crystalline Form A of Compound I-1

Compound I-1 (450 mg) was stirred in 2.5 ml ACN overnight with 5 heating/cooling cycles, filtered, and dried under vacuum to afford a white to off-white solid (Crystalline form A of I-1, 230 mg, 51% yield). The absolute stereochemistry was determined by X-ray crystallography. The product was isolated as a crystalline Form A.

X-Ray Powder Diffraction of the Crystalline Form A of Compound I-1

An x-ray powder diffraction pattern was recorded on a Bruker™ D8 GADDS Discover diffractometer with CuKα anode (CuKα radiation (λ=1.5418 Å). The X-ray diffraction pattern thus determined is shown in FIG. 1 and represented in Table 1 below by the reflection lines of the most important lines.

TABLE 1

| Angle (2-Theta °) | Intensity (%) |
|---|---|
| 7.077 | 18.7 |
| 7.833 | 12.6 |
| 8.665 | 43.7 |
| 10.654 | 35.5 |
| 13.037 | 68.8 |
| 15.647 | 24.6 |
| 16.038 | 23.9 |
| 16.328 | 19.6 |
| 17.024 | 16.1 |
| 17.328 | 47.2 |
| 17.681 | 29.7 |
| 18.734 | 82 |
| 19.202 | 86.7 |
| 19.529 | 46 |
| 20.18 | 100 |
| 20.934 | 38.3 |
| 21.355 | 24.7 |
| 21.629 | 26.2 |
| 22.352 | 19.9 |
| 22.599 | 17.8 |
| 22.818 | 18.9 |
| 23.39 | 31.3 |
| 23.772 | 41.5 |
| 24.34 | 23 |
| 24.907 | 23.6 |
| 25.691 | 23 |
| 26.159 | 24.3 |
| 27.218 | 41.2 |
| 27.28 | 34.1 |
| 27.502 | 28.1 |
| 28.528 | 16.9 |
| 28.768 | 17.2 |
| 29.255 | 35.3 |
| 29.775 | 22.4 |
| 31.593 | 18.4 |
| 32.156 | 17.4 |
| 34.124 | 14 |
| 36.147 | 18.2 |
| 36.201 | 18.5 |
| 36.938 | 16.7 |
| 41.106 | 16.6 |
| 43.839 | 15.7 |

DSC and TGA of the Crystalline Form A of Compound I-1

Crystalline form A of I-1 showed a melting endotherm of $T_{onset}=124.76°$ C., $\Delta H=84.33$ J/g and a small initial weight loss of 0.51% before 130° C. (FIG. 2).

Example 1B: Synthesis of Sodium Salt of Compound I-1

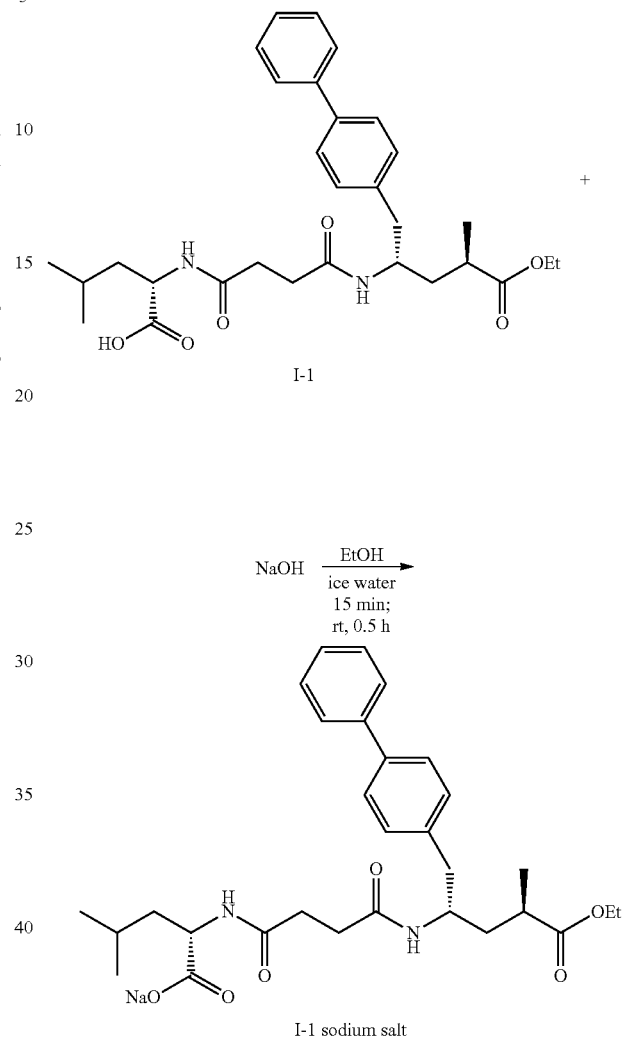

To a solution of compound I-1 (4.0936 g, 7.8024 mmol) in 160 mL ethanol was added 15.6 mL 0.5 N aq. NaOH (7.80 mmol) over 15 minutes. After stirring for 0.5 h at room temperature, approximately 100 mL of ethanol was evaporated off under reduced pressure and 100 mL of water was added. The mixture was then concentrated under reduced pressure until the volume of the remaining solution was about 50 mL. An additional 100 mL of water was added. The mixture was further concentrated under reduced pressure until the volume of the remained solution was about 80 mL, and the remaining solution was quickly frozen with liquid $N_2$ and lyophilized to afford an amorphous solid of the sodium salt of I-1 (4.20 g, 98.5%).

$^1$H NMR (δ, ppm, DMSO-$d_6$): 7.81 (1H, d), 7.65 (2H, d), 7.58 (2H, d), 7.45 (2H, t), 7.34 (1H, t), 7.28-7.21 (3H, m), 3.98 (2H, q), 3.94-3.85 (2H, m), 2.68 (2H, ddd), 2.48-2.43 (1H, m), 2.32-2.17 (4H, m), 1.79-1.69 (1H, m), 1.65-1.54 (1H, m), 1.52-1.44 (1H, m), 1.43-1.27 (2H, m), 1.12 (3H, t), 1.04 (3H, d), 0.83 (6H, d).

Example 2: Synthesis of Tert-butyl (4-(((2S,4R)-1-([1,1'-biphenyl]-4-yl)-5-ethoxy-4-methyl-5-oxopentan-2-yl)amino)-4-oxobutanoyl)-L-lysinate (I-3)

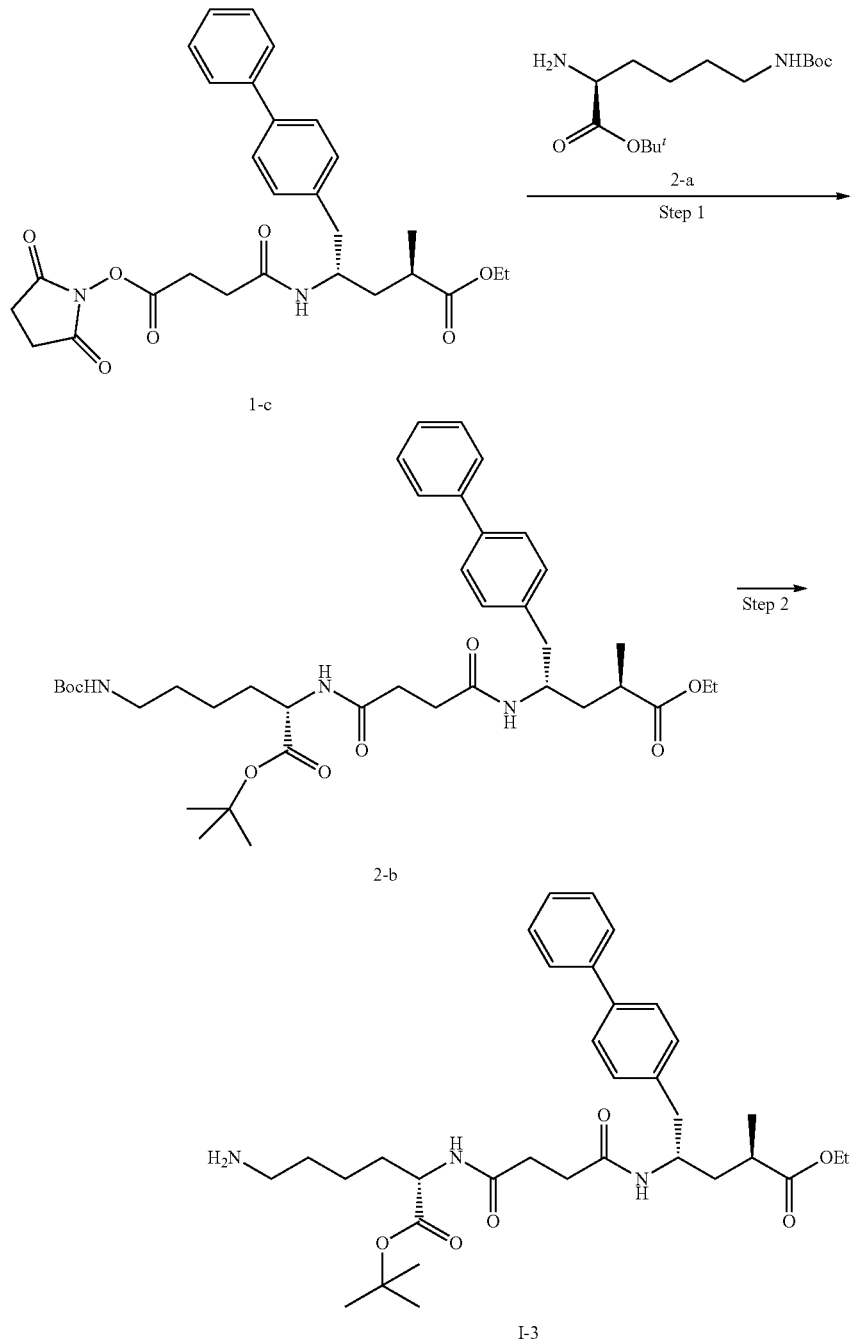

Step 1: Ethyl (10S,17S,19R)-17-([1,1'-biphenyl]-4-ylmethyl)-10-(tert-butoxycarbonyl)-2,2,19-trimethyl-4,12,15-trioxo-3-oxa-5,11,16-triazaicosan-20-oate (2-b)

To a mixture of Sac-OSu (1-c, 60 g, 117.9 mmol) and Lys-(Boc)-Ot-Bu (2-a, 43.97 g, 129.7 mmol) in THF (960 mL) was added sodium bicarbonate (19.8 g, 235.8 mmol) and water (240 mL). The reaction mixture was then stirred at ambient temperature for 3 h. Once HPLC indicated complete consumption of starting material and 84.09% product, the solvent was evaporated under reduced pressure at 50° C. The crude product was further diluted with water (300 mL) and extracted with EtOAc (3×300 mL). The combined organic layers were washed with water (300 mL) and brine (300 mL, dried over anhydrous Na$_2$SO$_4$, filtered, and concentrated to dryness under reduced pressure at 45° C. The resulting crude product (100 g) was dissolved in iPrOAc (300 mL) at ambient temperature and hexanes (900 mL) was then added. The resulting solid was collected by filtration and washed with hexanes (120 mL), to afford Sac-Lys-Boc-Bu (2-b, 70.5 g, 86%) as a white solid. HPLC purity: 93.31% and $^1$H NMR (δ, ppm, DMSO-d$_6$): 8.1 (1H, d), 7.74 (1H, d), 7.65 (2H, d), 7.6 (2H, d), 7.4-7.5 (2H, t), 7.3-7.4 (1H, t), 7.2 (2H, d), 6.8 (1H, m), 4.0 (4H, m), 2.9 (2H, m), 2.6-2.9 (2H, m), 2.2-2.4 (4H, m), 1.7-1.8 (1H, m), 1.5-1.7 (2H, m), 1.2-1.4 (23H, m), 1.0-1.1 (6H, m). One D$_2$O exchangeable proton was not detected by NMR. LCMS: 96.45% ([M+1]= 696.2).

Step 2: Tert-butyl (4-(((2S,4R)-1-([1,1'-biphenyl]-4-yl)-5-ethoxy-4-methyl-5-oxopentan-2-yl)amino)-4-oxobutanoyl)-L-lysinate (I-3)

To a solution of Sac-Lys-Boc-Bu (2-b, 24 g, 34.48 mmol) in dry toluene (240 mL) at 0-5° C. under nitrogen was added TFA (60 mL) and the resulting mixture was stirred at the same temperature for 4 h. HPLC indicated, some starting material, and the mixture was further stirred at 15° C. for 2 h. Once HPLC indicated 0.34% starting material and 79.87% product, the reaction mixture was quenched with 30% aq. Na$_2$CO$_3$ (240 mL, pH: 9.6), and water (120 mL) was then added. The aqueous layer was extracted with EtOAc (3×120 mL). The combined organic layers were washed with water (120 mL) and brine (120 mL), dried over Na$_2$SO$_4$, filtered, and concentrated to dryness under reduced pressure.

The resulting crude product was dissolved in iPrOAc (480 mL). Water (120 mL) was then added, the pH was adjusted to a pH of 9-10 using 30% Na$_2$CO$_3$ solution (48 mL) and the resulting mixture was stirred for 1 h at ambient temperature. The organic layer was washed with water (5×120 mL) and brine (120 mL), dried over Na$_2$SO$_4$, filtered, and evaporated under reduced pressure. The crude product was purified by column chromatography using grace instrument with DCM/MeOH (0-17%), to afford Sac-Lys-Bu (I-3, 5.2 g, 25.3%) as a sticky oil. HPLC purity: 98.36%. $^1$H NMR (DMSO-d$_6$): 8.1 (1H, bs), 7.7-7.8 (1H, d), 7.5-7.7 (3H, m), 7.2-7.5 (6H, m), 4.0 (4H, m), 2.7 (2H, m), 2.2-2.4 (5H, m), 2.0 (1H, s), 2.8 (2H, s), 1.4-1.7 (3H, m), 1.2-1.4 (12H, m), 0.9-1.2 (7H, m). Two D$_2$O exchangeable protons were not detected. LCMS: 94.14% ([M+1]=596.0).

Synthesis of Crystalline Form of the Succinate Salt of Compound I-3

Compound I-3 (0.167 mmol, 118 mg, purity 84.5%) was dissolved into 3 ml of ACN. Succinic acid (0.167 mmol, 19.8 mg) was added into the solution containing I-3 as a solid. The resulting mixture was then heated to 50° C. to give a clear solution, stirred for 2 hours at 50° C., and then cooled to room temperature. A slurry was formed during the cooling process which was further stirred overnight at room temperature. The solid was filtered off, washed with MTBE, and dried under vacuum at 40° C. to afford a white to off-white solid (Crystalline form of a succinate salt of 1-3, 84 mg, 70% yield).

X-Ray Powder Diffraction of the Crystalline Form of the Succinate Salt of Compound I-3

An x-ray powder diffraction pattern was recorded on a Bruker™ D8 GADDS Discover diffractometer with CuKα anode (CuKα radiation (λ=1.5418 Å). The X-ray diffraction pattern thus determined is shown in FIG. 7 and represented in Table 2 below by the reflection lines of the most important lines.

TABLE 2

| Angle (2-Theta °)<br>2-Theta ° | Intensity (%)<br>% |
| --- | --- |
| 8.495 | 38.2 |
| 11.194 | 61.1 |
| 12.705 | 78.5 |
| 13.37 | 39.8 |
| 14.795 | 32 |
| 16.122 | 42.4 |
| 16.934 | 51.2 |
| 18.056 | 43.7 |
| 19.196 | 51.6 |
| 19.597 | 61.7 |
| 20.141 | 40.6 |
| 20.794 | 68 |
| 20.855 | 66 |
| 21.763 | 100 |
| 22.472 | 34.1 |
| 23.649 | 30.6 |
| 24.411 | 28.6 |
| 25.599 | 32.9 |
| 26.428 | 38.7 |
| 26.697 | 38.3 |
| 27.639 | 29 |
| 28.502 | 36 |
| 31.629 | 25.2 |
| 32.436 | 24.6 |

DSC and TGA of Crystalline Form of the Succinate Salt of Compound I-3

Crystalline form of the Succinate Salt of 1-3 showed a melting endotherm of T$_{onset}$=102.85° C., ΔH=73.13 J/g and a weight loss of 1.15% before 120° C. (FIG. 8)

Synthesis of Crystalline Form of the Malonate Salt of Compound I-3

Compound I-3 (0.167 mmol, 118 mg, purity 84.5%) was dissolved into 3 ml of ACN. Malonic acid (0.167 mmol, 17.4 mg) was added into the solution containing I-3 as a solid. The resulting mixture was heated to 50° C. to give a clear solution stirred for 2 hours at 50° C., and then cooled to room temperature. A slurry was formed during the cooling process which was further stirred overnight at room temperature. The resulting solid was filtered off, washed with MTBE, and dried under vacuum at 40° C. to afford a white to off-white solid (Crystalline form of a malonate salt of I-3, 64 mg, 55% yield).

X-Ray Powder Diffraction of the Crystalline Form of the Malonate Salt of Compound I-3

An x-ray powder diffraction pattern was recorded on a Bruker™ D8 GADDS Discover diffractometer with CuKα anode (CuKα radiation (λ=1.5418 Å). The X-ray diffraction pattern thus determined is shown in FIG. 9 and represented in Table 3 below by the reflection lines of the most important lines.

TABLE 3

| Angle (2-Theta °) | Intensity (%) |
| --- | --- |
| 8.727 | 21.7 |
| 10.826 | 17.7 |
| 11.466 | 63.5 |
| 13.053 | 47.2 |
| 13.709 | 40.4 |
| 15.214 | 31.8 |
| 15.74 | 37.2 |
| 15.811 | 44.1 |
| 17.428 | 36.9 |
| 18.424 | 30 |
| 19.069 | 52.7 |
| 19.369 | 60 |
| 19.422 | 55.7 |

TABLE 3-continued

| Angle (2-Theta °) | Intensity (%) |
|---|---|
| 19.702 | 41.9 |
| 20.381 | 59.4 |
| 21.309 | 100 |
| 21.708 | 61.4 |
| 22.325 | 34 |
| 22.952 | 33 |
| 24.051 | 32.3 |
| 24.745 | 28.5 |
| 26.606 | 50.2 |
| 26.807 | 47.1 |
| 27.547 | 27.8 |
| 28.488 | 37.9 |
| 28.595 | 34.1 |
| 32.366 | 27.8 |
| 33.285 | 25.9 |

DSC and TGA of Crystalline Form of the Malonate Salt of Compound I-3

Crystalline form of the malonate salt of I-3 showed a melting endotherm of $T_{onset}$=102.24° C., ΔH=56.60 J/g and a weight loss of 1.33% before 120° C. (FIG. 10)

Synthesis of Crystalline Form of the Fumarate Salt of Compound I-3

Compound I-3 (0.167 mmol, 118 mg, purity 84.5%) from previous synthesis steps was dissolved into 3 ml of ACN. Fumaric acid (0.167 mmol, 19.4 mg) was added into the solution containing I-3 as a solid. The resulting mixture was heated to 50° C. and turned into a turbid slurry, which was then stirred for 2 hours at 50° C., cooled to room temperature, and further stirred overnight at room temperature. The resulting solid was filtered off, washed with MTBE, and dried under vacuum at 40° C. to afford a white to off-white solid (Crystalline form of a fumarate salt of I-3, 84 mg, 70% yield).

X-Ray Powder Diffraction of the Crystalline Form of the Fumarate Salt of Compound I-3

An x-ray powder diffraction pattern was recorded on a Bruker™ D8 GADDS Discover diffractometer with CuKα anode (CuKα radiation (λ=1.5418 Å). The X-ray diffraction pattern thus determined is shown in FIG. 11 and represented in Table 4 below by the reflection lines of the most important lines.

TABLE 4

| Angle (2-Theta °) | Intensity (%) |
|---|---|
| 6.635 | 52.9 |
| 8.831 | 85.3 |
| 13.11 | 93.4 |
| 13.23 | 100 |
| 10.602 | 58.1 |
| 15.421 | 73.2 |
| 17.663 | 64 |
| 19.187 | 82 |
| 20.151 | 81.7 |
| 22.078 | 89.7 |
| 24.746 | 74.5 |
| 26.472 | 68.6 |
| 28.892 | 63.9 |

DSC and TGA of Crystalline Form of the Fumarate Salt of Compound I-3

Crystalline form of the fumarate salt of I-3 showed a melting endotherm of $T_{onset}$=127.49° C., ΔH=57.10 J/g and a weight loss of 1.06% before 120° C. (FIG. 12)

Example 3: Synthesis of (4-(((2S,4R)-1-([1,1'-biphenyl]-4-yl)-5-ethoxy-4-methyl-5-oxopentan-2-yl)amino)-4-oxobutanoyl)-L-lysine (I-2)

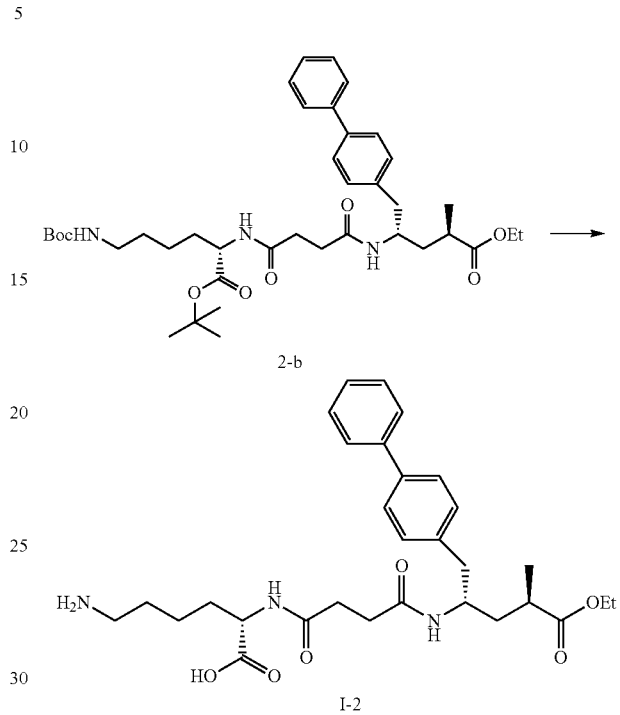

To a solution of Sac-Lys-Boc-Bu (2-b, 40 g, 57.4 mmol) in toluene (400 mL) at ambient temperature was added TFA. The resulting mixture was then stirred for 20 h at same temperature with HPLC monitoring. Once HPLC showed consumption of starting and 77.57% product formation, the solvent was removed by evaporation under reduced pressure. ACN (2×200 mL) was added and evaporated twice under reduced pressure. The resulting crude product was dissolved in acetonitrile (200 mL) and water (40 mL). Solid NaHCO₃ was then added until the solution had a pH of ~5.5-6. The resulting mixture was filtered and filtrate was subjected for reverse phase grace purification using water:acetonitrile. The resulting solid was dissolved in MeOH (400 mL), and then to dryness (ROI: 1.25%). The material was then dissolved in 30% IPA in DCM (1920 mL), stirred for 30 min at ambient temperature, and filtered through Celite®. The resulting filtrate was concentrated to dryness under reduced pressure. Any remaining solvent was stripped off with IPA (2×48 mL) by adding IPA and concentrating to dryness under reduced pressure twice. This afforded sacubitril lysine (I-2, 6.5 g, 43.5%) as white solid. HPLC purity: 99.39%. ¹H-NMR (δ, ppm, DMSO-d₆): 7.79 (1H, d), 7.5-7.7 (4H, m), 7.2-7.5 (6H, m), 3.8-4.0 (4H, m), 2.7 (4H, m), 2.3, (4H, m), 1.2-1.7 (8H, m), 1.1-1.2 (6H, m). One D₂O exchangeable proton was not detected. LCMS: 97.02% ([M+1]=539.9).

Synthesis of Crystalline Form a of Compound I-2

Compound I-2 (150 mg) was dissolved into 0.3 ml of water by sonication. Acetone (5.7 ml) was gradually added into the solution with stirring to provide a slurry. The mixture was then stirred overnight, filtered, and dried under low vacuum at room temperature to afford a white to off-white solid (Crystalline Form A of I-2, 120 mg, 80% yield).

X-Ray Powder Diffraction of the Crystalline Form a of Compound I-2

An x-ray powder diffraction pattern was recorded on a Bruker™ D8 GADDS Discover diffractometer with CuKα anode (CuKα radiation (λ=1.5418 Å). The X-ray diffraction pattern thus determined is shown in FIG. 3 and represented in Table 5 below by the reflection lines of the most important lines.

TABLE 5

| Angle (2-Theta °) | Intensity (%) |
| --- | --- |
| 10.62 | 35.6 |
| 10.774 | 54.8 |
| 11.145 | 20.9 |
| 12.072 | 80.2 |
| 12.195 | 56.3 |
| 13.439 | 62.9 |
| 13.6 | 49.6 |
| 15.118 | 57.4 |
| 15.976 | 86 |
| 16.129 | 78.7 |
| 16.65 | 35.4 |
| 16.71 | 32.9 |
| 17.103 | 26.4 |
| 19.162 | 100 |
| 19.943 | 72.7 |
| 20.675 | 52.9 |
| 20.774 | 62.2 |
| 21.24 | 43.9 |
| 21.302 | 50.3 |
| 21.608 | 52.9 |
| 21.946 | 51.6 |
| 22.059 | 52.1 |
| 22.472 | 90.6 |
| 23.163 | 54.1 |
| 23.334 | 52.5 |
| 23.975 | 42.6 |
| 24.321 | 41.2 |
| 25.039 | 42.2 |
| 26.873 | 38.5 |
| 27.109 | 42.1 |
| 27.512 | 39.5 |
| 28.782 | 37.1 |
| 29.097 | 34 |

DSC and TGA of the Crystalline Form a of 1-2

Crystalline form A of I-2 appeared to be a channel hydrate. As seen in the DSC thermogram in FIG. 4, the endothermic peak between 50° C. to 130° C. was attributed to the loss of channel water molecule, which was corresponding to 3.31% of weight loss in the same temperature range in the TGA thermogram. After losing the channel water, the compound showed a melting peak at 209.06° C. ($T_{onset}$=206.95° C., ΔH=97.49 J/g).

Synthesis of Crystalline Form B of 1-2

Compound I-2 (150 mg) was stirred in 1 ml ethanol, with the application of 4 heating/cooling cycles, then filtered and dried under vacuum at 40° C. to afford a white to off-white solid (Crystalline Form B of 1-2, 55 mg, 79% yield).

X-Ray Powder Diffraction of the Crystalline Form B of 1-2

An x-ray powder diffraction pattern was recorded on a Bruker™ D8 GADDS Discover diffractometer with CuKα anode (CuKα radiation (λ=1.5418 Å). The X-ray diffraction pattern thus determined is shown in FIG. 5 and represented in Table 6 below by the reflection lines of the most important lines.

TABLE 6

| Angle (2-Theta °) | Intensity (%) |
| --- | --- |
| 8.704 | 38.3 |
| 9.289 | 66.6 |
| 12.351 | 32.4 |
| 13.547 | 58 |
| 14.81 | 26.2 |
| 15.486 | 30.7 |
| 16.165 | 59.3 |
| 16.566 | 30.3 |
| 16.925 | 24.2 |
| 17.503 | 100 |
| 18.027 | 28.2 |
| 18.647 | 17.6 |
| 18.917 | 28 |
| 20.49 | 20 |
| 21.786 | 42.2 |
| 23.278 | 21.6 |
| 23.677 | 23.2 |
| 24.773 | 40.4 |
| 24.965 | 44.9 |
| 25.72 | 25.4 |
| 26.25 | 33.2 |
| 28.08 | 29.4 |
| 28.566 | 22.3 |
| 32.334 | 20.3 |
| 32.895 | 21 |
| 37.257 | 18.2 |
| 38.708 | 20.9 |
| 39.858 | 17.1 |

DSC and TGA Crystalline Form B of 1-2

Crystalline form B of I-2 appeared to be a channel hydrate. As seen in the DSC thermogram in FIG. 6, the endothermic peak between 60° C. to 130° C. was attributed to the loss of channel water molecule, which was corresponding to 4.53% of weight loss in the same temperature range in the TGA thermogram. After losing the channel water, the compound showed a recrystallization peak at 178.72° C. ($T_{onset}$=173.58° C., ΔH=33.61 J/g), followed by a melting peak at 209.06° C. ($T_{onset}$=206.95° C., ΔH=97.49 J/g).

Example 4: Synthesis of ethyl (2R,4S)-5-([1,1'-biphenyl]-4-yl)-4-(4-(((S)-1-ethoxy-4-methyl-1-oxopentan-2-yl)amino)-4-oxobutanamido)-2-methylpentanoate (I-4)

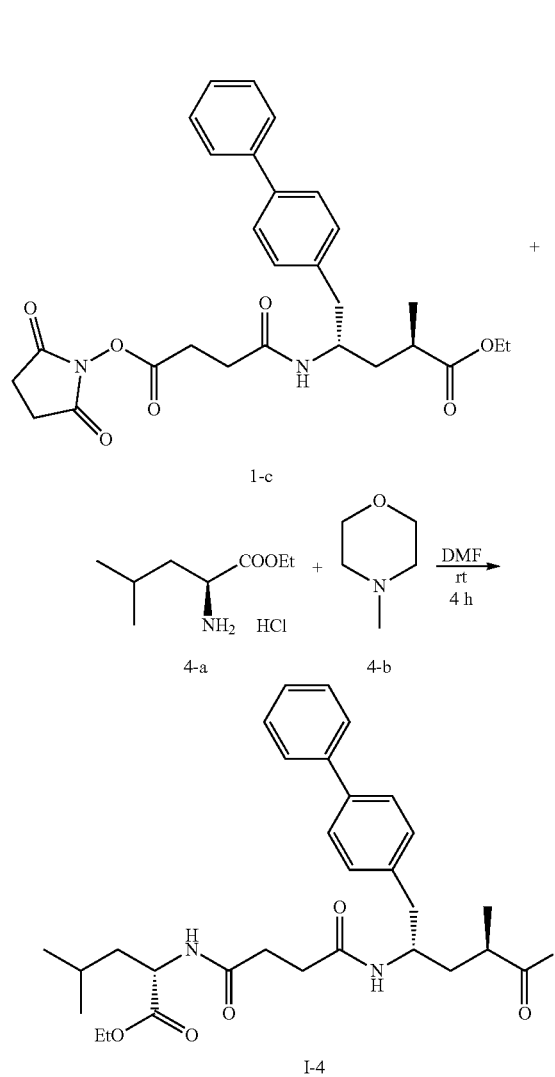

Example 5: Synthesis of (4-(((2S,4R)-1-([1,1'-biphenyl]-4-yl)-5-ethoxy-4-methyl-5-oxopentan-2-yl)amino)-4-oxobutanoyl)-L-arginine (I-5)

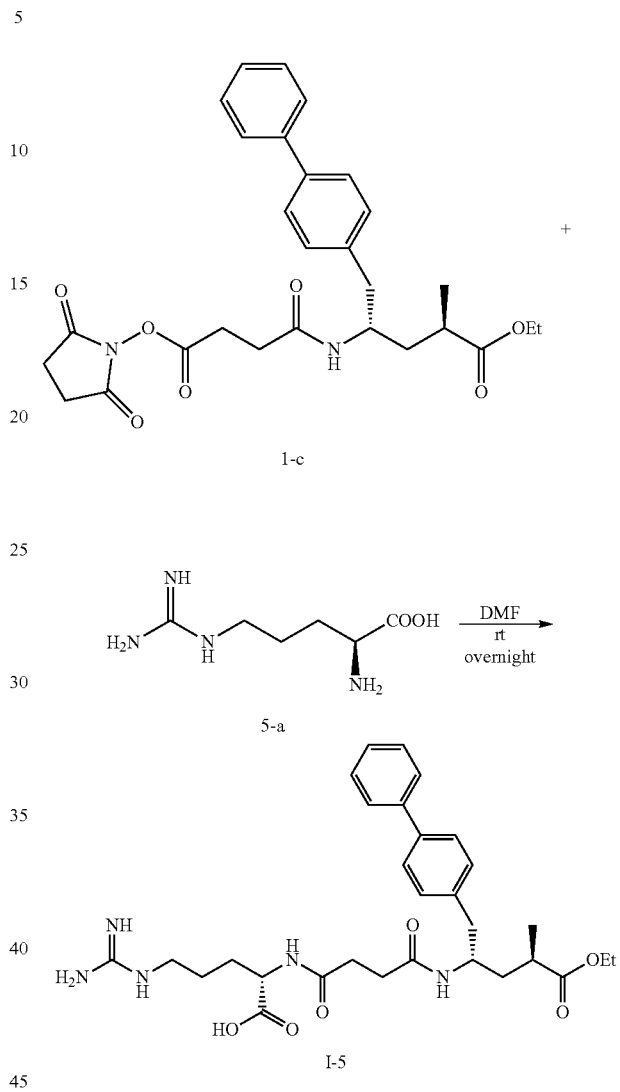

A mixture of 1-c (0.2629 g, 0.5169 mmol), ethyl L-leucinate hydrochloride (4-a, 0.1572 g, 0.8033 mmol) and 4-methylmorpholine (4-b, 0.0750 mL, 0.682 mmol) and DMF (5 mL) was stirred for 4 h at room temperature. The mixture was partitioned between 25 mL EtOAc and washed with 25 mL 0.05 M HCl aqueous solution. The organic layer was washed with 3×10 mL of water and 10 mL of brine, and dried over anhydrous $Na_2SO_4$. After filtration, the filtrate was concentrated under reduced pressure. The petroleum ether was added to the resulting residue and the resulting mixture was frozen at −20° C. overnight, shaken with ultrasound, and filtered to afford the title compound (I-4) as a white solid (0.2302 g, yield: 80.6%) (HPLC purity: 99.02%).

$^1$H NMR (δ, ppm, $CDCl_3$): 7.61-7.55 (2H, m), 7.52 (2H, d), 7.43 (2H, t), 7.33 (1H, t), 7.24 (2H, d), 6.23 (1H, d), 5.86 (1H, d), 4.56 (1H, td), 4.28-4.19 (1H, m), 4.19-4.08 (m, 4H), 2.83 (2H, d), 2.57-2.52 (1H, m), 2.52-2.47 (2H, m), 2.47-2.42 (2H, m), 1.93 (1H, ddd), 1.69-1.61 (2H, m), 1.55-1.45 (2H, m), 1.25 (6H, q), 1.15 (3H, d), 0.94 (3H, d), 0.93 (3H, d).

LC-MS (ES-API positive): 96.62% ([M+1]=553.3).

A mixture of 1-c (0.1134 g, 0.2230 mmol), arginine (5-a, 0.0775 g, 0.445 mmol) in DMF (5 mL) was stirred overnight at room temperature. The reaction mixture was directly purified by reverse phase column chromatography (C-18, grain size: 40 μm, pore size distribution: 120 Å) eluting with water/MeCN (10/1 to 1/4) to afford the crude product (0.1358 g), which was washed with a mixture of 2 mL DMSO and 10 mL water, filtered, and dried with air to give the title compound I-5 (0.0618 g, yield: 48.8%) as a white solid (HPLC purity: 98.20%).

$^1$H NMR (δ, ppm, DMSO-$d_6$): 9.38 (1H, s), 7.75 (1H, d), 7.68-7.62 (2H, m), 7.57 (2H, d), 7.53 (1H, d), 7.44 (2H, t), 7.33 (2H, t), 7.24 (2H, d), 3.98 (2H, q), 3.95-3.86 (2H, m), 3.05 (2H, m), 2.67 (2H, ddd), 2.48-2.43 (1H, m), 2.34-2.22 (4H, m), 1.78-1.70 (1H, m), 1.67-1.59 (1H, m), 1.59-1.53 (1H, m), 1.53-1.39 (2H, m), 1.39-1.33 (1H, m), 1.11 (3H, t), 1.04 (3H, d). Three $D_2O$ exchangeable protons were not detected by NMR.

LC-MS (ES-API positive): 96.15%, 568.3 $[M+H]^+$.

Example 6: Synthesis of (4-(((2S,4R)-1-([1,1'-biphenyl]-4-yl)-5-ethoxy-4-methyl-5-oxopentan-2-yl)amino)-4-oxobutanoyl)-L-histidine (I-6)

Example 7: Synthesis of (4-(((2S,4R)-1-([1,1'-biphenyl]-4-yl)-5-ethoxy-4-methyl-5-oxopentan-2-yl)amino)-4-oxobutanoyl)glycine (I-7)

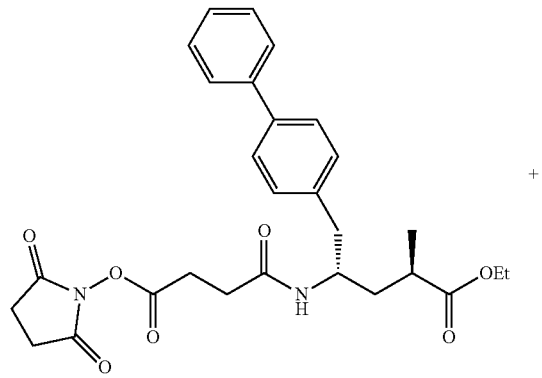
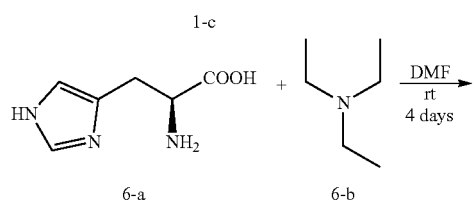
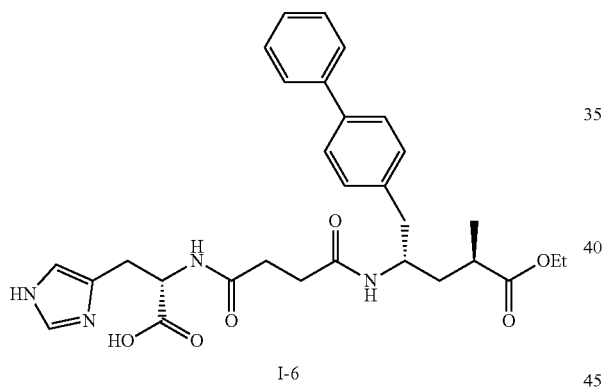
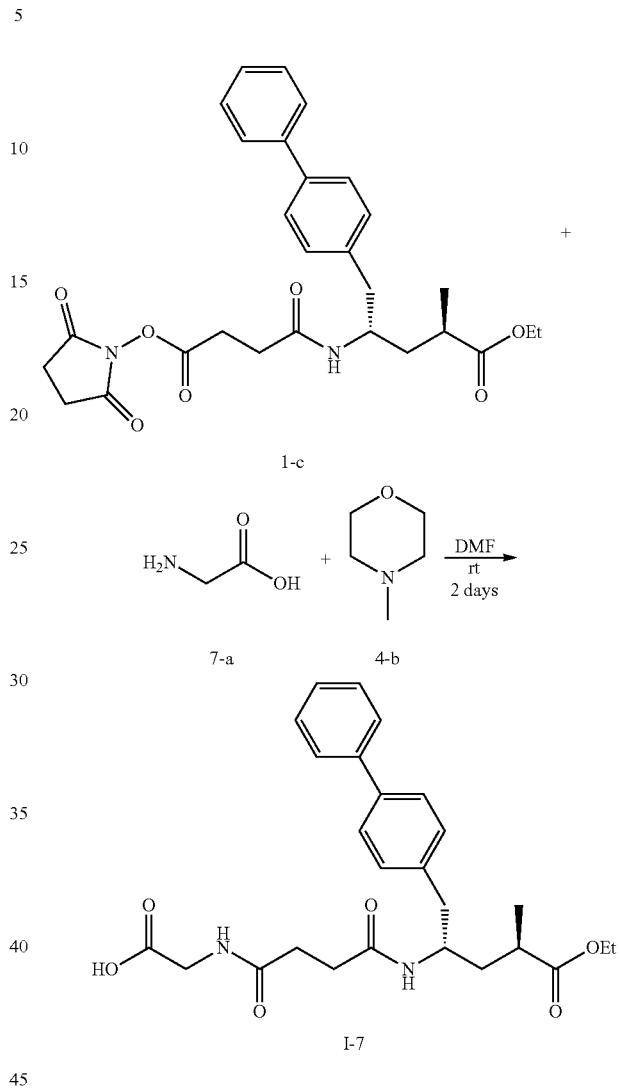

A mixture of 1-c (0.1150 g, 0.2261 mmol), histidine (6-a, 0.1872 g, 1.206 mmol), triethylamine (6-b, 0.152 mL, 1.094 mmol) in DMF (5 mL) was stirred for 4 days at room temperature until 1-c was completely consumed in the reaction. The reaction mixture was directly purified by reverse phase column chromatography (C-18, grain size: 40 μm, pore size distribution: 120 Å) elutting with water/MeCN (10/1 to 1/4) and the fractions containing the product were collected and lyophilized to afford the title compound I-6 as a white solid (0.0953 g, yield: 76.8%).

HPLC purity: 98.44% and $^1$H NMR (δ, ppm, DMSO-$d_6$): 8.21 (1H, s), 8.08 (1H, d), 7.82 (1H, d), 7.65 (2H, d), 7.61-7.54 (3H, m), 7.46 (2H, t), 7.35 (1H, t), 7.25 (2H, d), 6.80 (1H, s), 4.35 (1H, dd), 4.01-3.93 (2H, m), 3.93-3.86 (1H, m), 2.94 (1H, dd), 2.83 (1H, dd), 2.68 (2H, ddd), 2.49-2.44 (m, 1H), 2.35-2.27 (2H, m), 2.27-2.19 (2H, m), 1.74 (1H, ddd), 1.38 (1H, ddd), 1.10 (3H, t), 1.04 (3H, d). Two D$_2$O exchangeable protons were not detected by NMR.

LC-MS (ES-API positive): 97.19% ([M+1]=549.1).

To a mixture of 1-c (0.139 g, 0.273 mmol) and Glycine (7-a, 0.079 g, 1.052 mmol) in DMF (5 mL) was added 4-methylmorpholine (4-b, 0.145 mL, 1.088 mmol). The reaction mixture was then stirred at room temperature for 2 days. Once HPLC indicated complete consumption of starting material 1-c, 5 mL H$_2$O and 3 mL 1 N HCl were added to the reaction mixture. The resulting mixture was then directly purified by reverse phase column chromatography (C-18, grain size: 40 μm, pore size distribution: 120 Å) eluteting with H$_2$O/ACN (10 to 90%), and the fractions containing product were collected and lyophilized to afford the title compound I-7 (0.1050 g, 81.4%) as a white solid (HPLC purity: 98.48%).

$^1$H NMR (δ, ppm, DMSO-$d_6$): 12.50 (1H, brs), 8.18 (1H, t), 7.75 (1H, d), 7.65 (2H, d), 7.58 (2H, d), 7.45 (2H, t), 7.34 (1H, t), 7.25 (2H, d), 3.98 (2H, q), 3.86-39.4 (1H, m), 3.72 (2H, d), 2.74-2.62 (2H, m), 2.74-2.62 (2H, m), 2.36-2.30 (2H, m), 2.48-2.43 (1H, m), 1.75 (1H, ddd), 1.38 (1H, ddd), 1.12 (3H, t), 1.05 (3H, d).

LC-MS (ES-API positive): 98.91% (469.1, [M+1]$^+$).

Example 8: Synthesis of (4-(((2S,4R)-1-([1,1'-bi-phenyl]-4-yl)-5-ethoxy-4-methyl-5-oxopentan-2-yl)amino)-4-oxobutanoyl)-L-alanine (I-8)

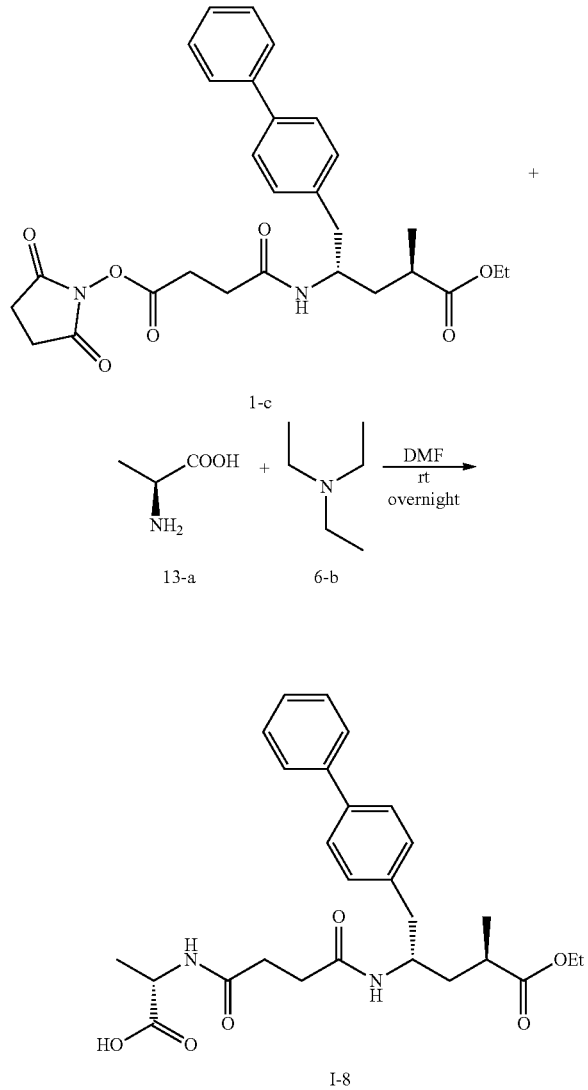

A mixture of 1-c (0.1045 g, 0.2055 mmol), L-alanine (13-a, 0.1053 g, 1.182 mmol), triethylamine (6-b, 0.16 mL, 1.15 mmol) in DMF (5 mL) was stirred overnight at room temperature until 1-c disappeared. The reaction mixture was directly purified by reverse phase column chromatography (C-18, grain size: 40 μm, pore size distribution: 120 Å) eluting with water/MeCN (10/1 to 1/4) and the fractions containing product were collected and lyophilized to afford the title compound I-8 as a white solid (0.0792 g, yield: 79.9%, HPLC purity: 98.24%).

$^1$H NMR (δ, ppm, DMSO-d$_6$): 8.16 (1H, d), 7.76 (1H, d), 7.69-7.63 (2H, m), 7.58 (2H, d), 7.45 (2H, t), 7.34 (1H, t), 7.25 (2H, d), 4.17 (1H, p), 3.98 (2H, q), 3.96-3.85 (1H, m), 2.68 (2H, ddd), 2.49-2.42 (1H, m), 2.37-2.18 (m, 4H), 1.76 (1H, ddd), 1.42-1.33 (1H, m), 1.24 (3H, d), 1.12 (3H, t), 1.05 (3H, d). One D$_2$O exchangeable proton was not detected by NMR. LC-MS (ES-API positive): 99.65% ([M+1]=483.1).

Example 9: Synthesis of (4-(((2S,4R)-1-([1,1'-bi-phenyl]-4-yl)-5-ethoxy-4-methyl-5-oxopentan-2-yl)amino)-4-oxobutanoyl)-L-valine (I-9)

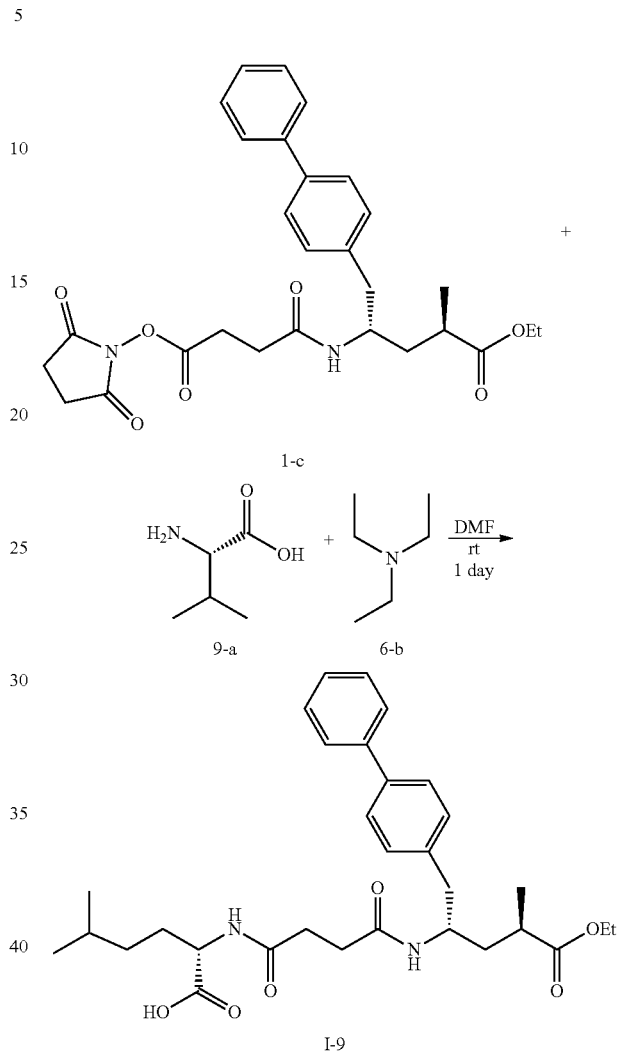

To a mixture of 1-c (0.1152 g, 0.219 mmol) and L-valine (9-a, 0.149 g, 1.273 mmol) in DMF (5 mL) was added triethylamine (6-b 0.150 mL, 1.08 mmol). The reaction mixture was then stirred at room temperature for 12 h. Once HPLC indicated complete consumption of starting material 1-c, 5 mL H$_2$O and 3 mL 1 N HCl were added and the resulting mixture was directly purified by reverse phase column chromatography (C-18, grain size: 40 μm, pore size distribution: 120 Å) eluting with H$_2$O/ACN (10% to 80%), and the fractions containing product were collected and lyophilized to afford the title compound I-9 (0.0680 g, 58.77%) as a white solid (HPLC purity: 98.66%).

$^1$H NMR (δ, ppm, DMSO-d$_6$): 12.53 (1H, br), 8.01 (1H, d), 7.74 (1H, d), 7.68-7.63 (2H, m), 7.58 (2H, d), 7.45 (2H, t), 7.34 (1H, t), 7.25 (2H, d), 4.14 (1H, dd), 4.03-3.95 (2H, m), 3.95-3.86 (1H, m), 2.68 (2H, qd), 2.48-2.44 (1H, m), 2.42-2.31 (2H, m), 2.31-2.18 (2H, m), 2.03 (1H, td), 1.76 (1H, ddd), 1.38 (1H, ddd), 1.12 (3H, t), 1.05 (3H, d), 0.87 (6H, d).

LCMS (ES-API positive): 98.11% ([M+1]=511.1).

Example 10: Synthesis of (4-(((2S, 4R)-1-([1,1'-biphenyl]-4-yl)-5-ethoxy-4-methyl-5-oxopentan-2-yl)amino)-4-oxobutanoyl)-L-phenylalanine (I-10)

Example 11: Synthesis of (4-(((2S,4R)-1-([1,1'-biphenyl]-4-yl)-5-ethoxy-4-methyl-5-oxopentan-2-yl)amino)-4-oxobutanoyl)-L-tryptophan (I-11)

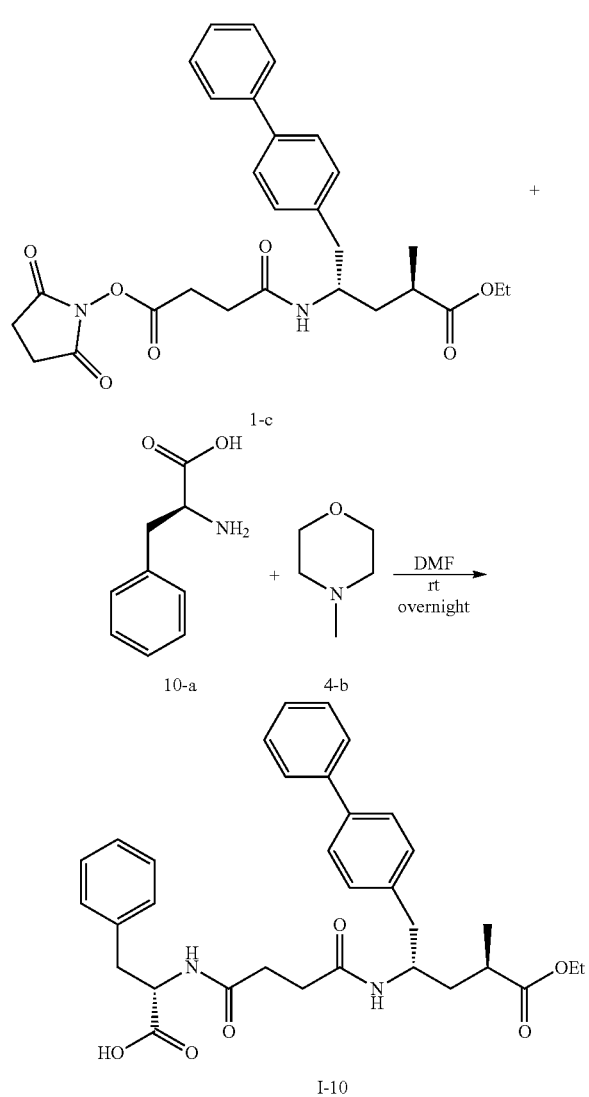

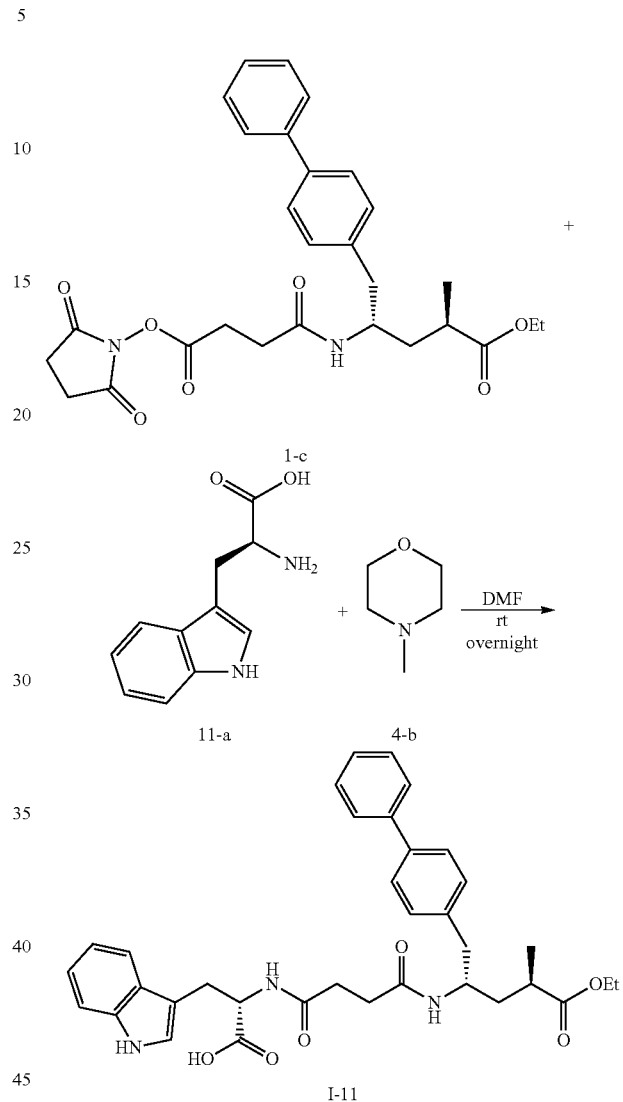

To a mixture of 1-c (100 mg, 0.197 mmol) and L-phenylalanine (10-a, 49.2 mg, 0.298 mmol) in DMF was added N-methylmorpholine (4-b, 0.0330 mL, 0.300 mmol). The reaction mixture was stirred at room temperature under $N_2$ atmosphere for 16 h. The mixture was then directly purified by reverse phase column chromatography (C-18, grain size: 40 μm, pore size distribution: 120 Å) eluting with water/MeCN (10/1 to 1/9), and the fractions containing product were collected and lyophilized to afford the title compound I-10 (94.5 mg, yield: 86.0%) as a white solid (HPLC purity: 98.17%)

$^1$H NMR (δ, ppm, DMSO) 7.99 (1H, s), 7.73 (1H, d), 7.66-7.61 (2H, m), 7.57 (2H, d), 7.45 (2H, t), 7.34 (1H, t), 7.27-7.14 (6H, m), 4.32 (1H, ddd), 4.01-3.93 (2H, m), 3.92-3.84 (1H, m), 3.05 (dd, 1H), 2.84 (1H, dd), 2.73-2.61 (2H, m), 2.48-2.41 (1H, m), 2.34-2.22 (2H, m), 2.21-2.15 (2H, m), 1.74 (1H, ddd), 1.37 (1H, ddd), 1.10 (3H, t), 1.04 (3H, d). One $D_2O$ exchangeable proton was not detected by NMR.

LC-MS (ES-API positive): 94.02% ([M+1]=559.1).

To a mixture of 1-c (100 mg, 0.197 mmol) and L-tryptophan (11-a, 60.6 mg, 0.297 mmol) in DMF was added N-methylmorpholine (4-b, 0.033 mL, 0.300 mmol). The reaction mixture was stirred at room temperature under $N_2$ atmosphere for 16 h. The resulting mixture was then directly purified by reverse phase column chromatography (C-18, grain size: 40 μm, pore size distribution: 120 Å) elutting with water/MeCN (10/1 to 1/9) and the fractions containing product were collected and lyophilized to afford the title compound I-11 (110 mg, 0.184 mmol, 93.6%) as a white solid (HPLC purity: 98.96%).

$^1$H NMR (δ, ppm, DMSO) 12.63 (1H, brs), 10.83 (1H, s), 8.18-8.11 (1H, m), 7.72 (d, 1H), 7.66-7.62 (2H, m), 7.57 (2H, d), 7.53 (1H, d), 7.44 (2H, t), 7.37-7.29 (2H, m), 7.24 (2H, d), 7.13 (1H, d), 7.08-7.02 (1H, m), 7.00-6.94 (1H, m), 4.44 (1H, td), 4.01-3.92 (2H, m), 3.92-3.85 (1H, m), 3.15 (1H, dd), 2.99 (1H, dd), 2.67 (2H, qd), 2.48-2.42 (1H, m), 2.37-2.25 (2H, m), 2.25-2.17 (2H, m), 1.74 (1H, ddd), 1.42-1.32 (1H, ddd), 1.09 (3H, t), 1.04 (3H, d).

LC-MS (ES-API positive): 98.57% ([M+1]=598.2).

Example 12: Synthesis of (4-(((2S,4R)-1-([1,1'-biphenyl]-4-yl)-5-ethoxy-4-methyl-5-oxopentan-2-yl)amino)-4-oxobutanoyl)-L-isoleucine (I-12)

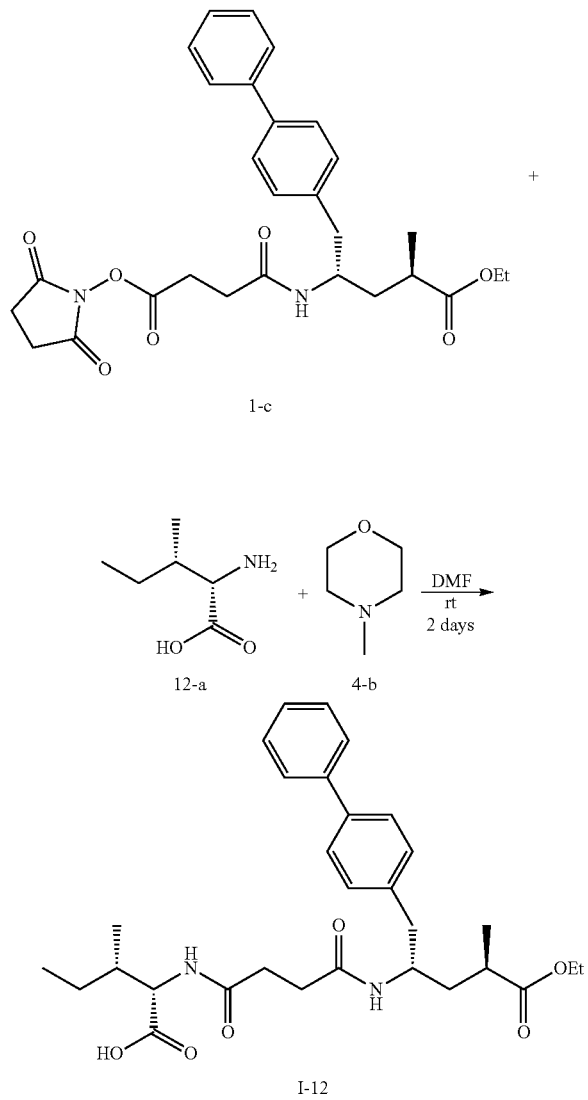

To a mixture of 1-c (100 mg, 0.197 mmol) and N-methylmorpholine (4-b, 0.033 mL, 0.295 mmol) in DMF was added L-isoleucine (12-a, 40.0 mg, 0.305 mmol). The reaction mixture was stirred at room temperature under $N_2$ atmosphere for 2 days. The resulting mixture was then directly purified by reverse phase column chromatography eluting with water/MeCN(10/1 to 1/9) and the fractions containing product were collected and lyophilized to afford the title compound I-12 (66.8 mg, 0.127 mmol, yield: 64.8%) as a white solid (HPLC purity: 96.78%).

$^1$H NMR (δ, ppm, DMSO) 12.65 (1H, brs), 7.97 (1H, d), 7.74 (1H, d), 7.67-7.62 (2H, m), 7.58 (2H, d), 7.45 (2H, t), 7.34 (1H, t), 7.25 (2H, d), 4.16 (1H, dd), 4.02-3.95 (2H, m), 3.94-3.86 (1H, m), 2.68 (2H, qd), 2.48-2.42 (1H, dd), 2.42-2.18 (4H, m), 1.80-1.69 (2H, m), 1.45-1.33 (2H, m), 1.23-1.14 (1H, m), 1.11 (3H, t), 1.04 (3H, d), 0.83 (6H, t).

LC-MS (ES-API positive): 98.63% ([M+1]=525.2).

Example 13: Pharmacokinetics of Compounds I-1, I-2 and I-3 in Male Sprague Dawley Rats A parallel study design consisting of four groups with three animals per group was conducted to examine the pharmacokinetic properties of the compounds of the present disclosure.

The drugs were administered to each group are as follows: compound I-1 (Group 1), compound I-2 (Group 2), compound I-3 (Group 3), and AHU377 (sacubitril) (Group 4). Each animal received a single 10 mg/kg (5 ml/kg) oral gavage dose of the specified study drug. The animal weights ranged from 250 mg to 300 mg at the beginning of the study. Compound I-1, compound I-2, compound I-3, and AHU377 were formulated in 0.5% methylcellulose (400 cp) and 0.1% Tween 80 (w,v) in water was used as the vehicle. Water bath sonication was applied to facilitate dispersing for all four study drugs. Blood samples for pharmacokinetics analysis were collected at t=0.25, 0.5, 1, 2, 4, 8, and 24 hours (±5%) post dose administration. Plasma was prepared by collecting whole blood samples into tubes containing EDTA and NaF (final concentrations: ~1 mg/mL ($K_2$EDTA) and ~2 mg/mL (NaF)). These tubes were kept in an ice bath prior to centrifugation at approximately 2,000 rcf for 10 minutes at approximately 5° C. To each resultant plasma sample, 50% phosphoric acid (v/v) was added to achieve a final concentration of 1% (v,v).

All animals exhibited normal disposition before and following treatment with no significant abnormalities observed during the study. One animal was noted to have mild diarrhea. In summary, the data suggests that a single oral administration of compound I-1, compound I-2, compound I-3, or AHU377 at 10 mg/kg is very well tolerated in male Sprague-Dawley rats.

Bioanalytics:

[$^{13}C_4$]-LBQ657 was added as an internal standard to the pharmacokinetic (PK) samples and calibration standards prior to analysis by LC-MS/MS. The LC-MS system consisted of an API6500+ mass spectrometer coupled to an Agilent 1290 HPLC system equipped with a CTC Pal autosampler. The mass spectrometer was operated in the positive ion mode with a TESI ion source. For the chromatographic separations, an Acquity BEH $C^{18}$, 50×2.1 mm LC column was used with the solvent gradients displayed in Table 7 below:

TABLE 7

Solvent gradients used for chromatographic separations

% Solvent B = 100 - % Solvent A

| Time (min) | Compound I-1 | Compound I-2 | Compound I-3 | AHU377 | Flowrate (μL/min) |
|---|---|---|---|---|---|
| 0.0 | 60 | 45 | 50 | 55 | 800 |
| 0.2 | 60 | 45 | 50 | 55 | 800 |
| 1.0 | 100 | 90 | 100 | 100 | 800 |
| 1.1 | 100 | 95 | 100 | 100 | 800 |
| 1.5 | 100 | 95 | 100 | 100 | 800 |
| 1.6 | 60 | 45 | 50 | 55 | 800 |
| 1.7 | 60 | 45 | 50 | 55 | 800 |

Solvent A = 5:95:0.1 (v:v:v) acetonitrile:water:formic acid
Solvent B = 50:50:0.1 (v:v:v) methanol:acetonitrile:formic acid The MS/MS mass transitions monitored for each analyte are shown in Table 8 below:

TABLE 8

MS/MS mass transitions monitored for each analyte

| Analyte | Precursor m/z | Product m/z |
|---|---|---|
| Compound I-1 | 525.4 | 394.2 |
| Compound I-2 | 540.4 | 394.3 |
| Compound I-3 | 596.4 | 540.3 |
| AHU377 | 412.4 | 266.1 |
| LBQ657 | 384.2 | 266.1 |
| [$^{13}C_4$]LBQ657 | 388.2 | 266.1 |

The chromatographic retention times of each of the analytes are displayed in Table 9 below:

TABLE 9

Chromatographic retention times of analytes (min)

| | Analytes | | | | |
|---|---|---|---|---|---|
| Study drug | Compound I-1 | Compound I-2 | Compound I-3 | AHU377 | LBQ657 |
| Compound I-1 | 0.82 | | | | 0.38 |
| Compound I-2 | | 0.73 | | | 0.75 |
| Compound I-3 | | | 0.86 | | 0.57 |
| AHU377 | | | | 0.76 | 0.44 |

Figure 13:
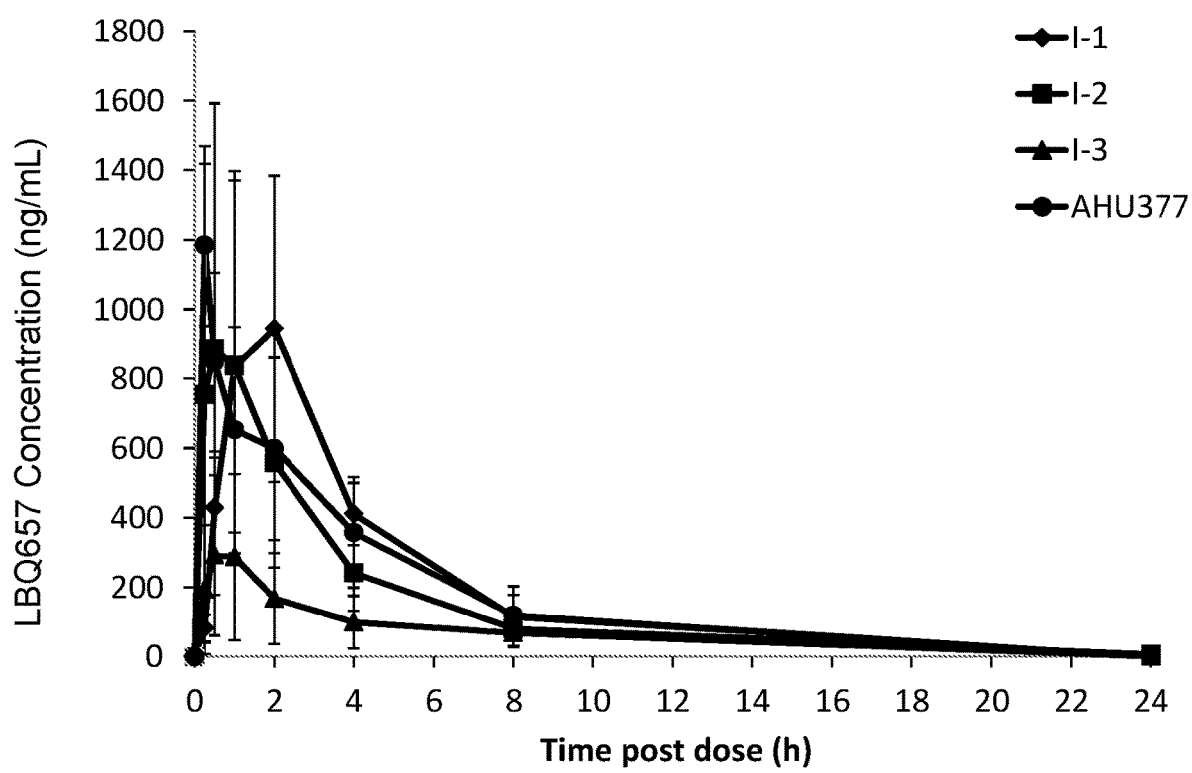
FIG. 13 is a graph showing the change in LBQ657 concentration over 0 to 24 hours after dosing Sprague Dawley rats with 10 mg/kg of compound I-1, 10 mg/kg of compound I-2, 10 mg/kg of compound I-3 or 10 mg/kg of AHU377 (sacubitril).
Figure 14:
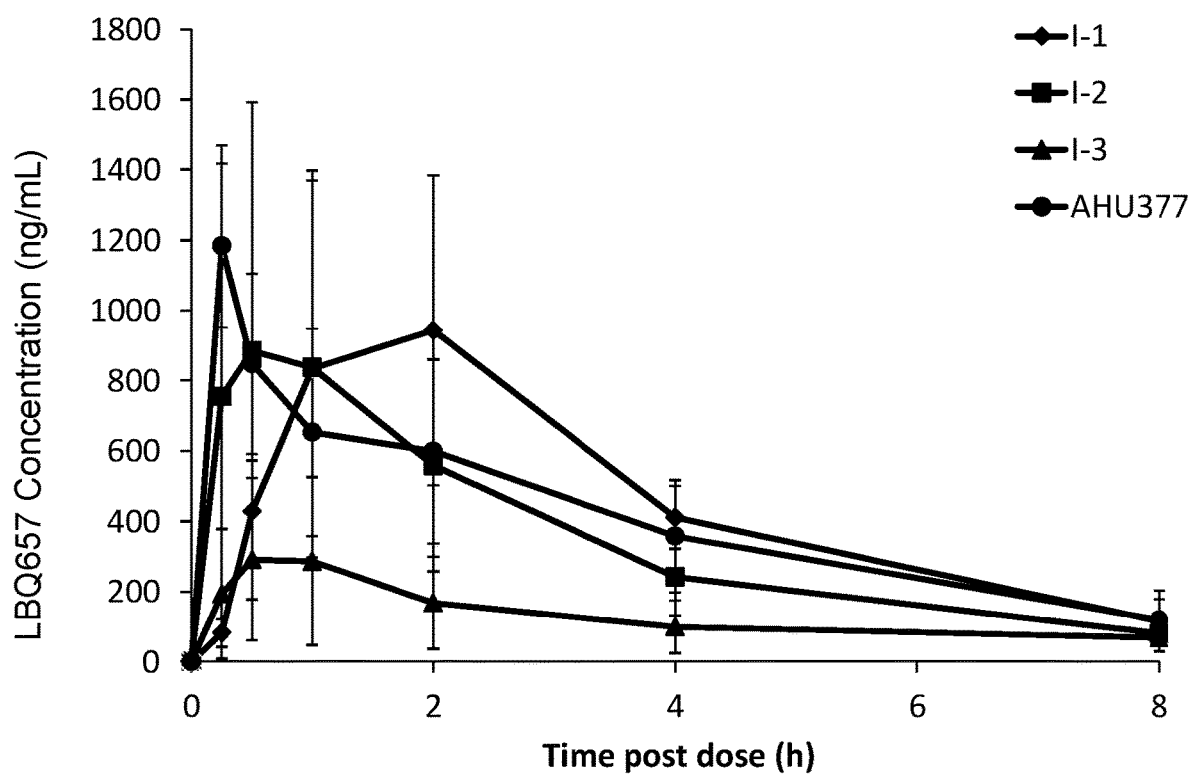
FIG. 14 is a graph showing the change in LBQ657 concentration over 0 to 8 hours after dosing Sprague Dawley rats with 10 mg/kg of compound I-1, 10 mg/kg of Compound I-2, 10 mg/kg of compound I-3 or 10 mg/kg of AHU377 (sacubitril).

Pharmacokinetics:

The mean pharmacokinetic concentration-time profiles of LBQ657 for compound I-1, compound I-2, compound I-3, and AHU377 are displayed in FIG. 13 and FIG. 14. FIG. 13 shows the profiles over the entire sample collection period (0-24 h) while FIG. 14 shows the expanded 0-8 hour time window.

The pharmacokinetic parameters for compound I-1, compound I-2, compound I-3, and AHU377, estimated using non-compartmental analysis, are displayed in the Tables 10-12 below.

TABLE 10

PK Parameters of Analyte LBQ657 for Compounds I-1, I-2, and I-3

| LBQ657 | Compound I-1 | | Compound I-2 | | Compound I-3 | | AHU337 | |
|---|---|---|---|---|---|---|---|---|
| PK Parameter | Mean | Std | Mean | Std | Mean | Std | Mean | Std |
| $T_{1/2}$ (h) | 2.51 | 0.307 | 3.52 | 1.22 | 3.51 | 1.43 | 4.33 | 3.69 |
| $T_{max}$ (h)* | 2.00 | N/A | 0.500 | N/A | 1.00 | N/A | 0.25 | N/A |
| $C_{max}$ (ng/ml) | 950 | 451 | 963 | 579 | 309 | 212 | 1185 | 233 |
| $AUC_{last}$ (h*ng/ml) | 4618 | 1331 | 3573 | 916 | 1618 | 767 | 3785 | 1263 |
| $AUC_{INF\_Obs}$(h*ng/ml) | 4624 | 1333 | 3620 | 885 | 1844 | 937 | 4543 | 506 |

*median values shown for $T_{max}$

TABLE 11

PK Parameters of Analyte AHU377 for Compounds I-1, I-2, and I-3

| LBQ657 | Compound I-1 | | Compound I-2 | | Compound I-3 | | AHU337 | |
|---|---|---|---|---|---|---|---|---|
| PK Parameter | Mean | Std | Mean | Std | Mean | Std | Mean | Std |
| $T_{1/2}$ (h) | 1.40 | N/A | 3.78 | 2.63 | 2.46 | 1.11 | 4.57 | 2.20 |
| $T_{max}$ (h)* | 2.00 | N/A | 0.250 | N/A | 0.250 | N/A | 0.250 | N/A |
| $C_{max}$ (ng/ml) | 15.4 | 6.52 | 23.9 | 17.9 | 5.66 | 4.84 | 19.1 | 6.55 |
| $AUC_{last}$ (h*ng/ml) | 61.6 | 15.6 | 32.3 | 8.58 | 12.8 | 11.7 | 27.8 | 9.91 |
| $AUC_{INF\_Obs}$(h*ng/ml) | 67.8 | 19.9 | 39.1 | 2.84 | 19.5 | 16.7 | 39.9 | 3.56 |

*median values shown for $T_{max}$

TABLE 12

PK Parameters for Compounds I-1, I-2, and I-3

| Prodrugs | Compound I-1 | | Compound I-2 | | Compound I-3 | |
|---|---|---|---|---|---|---|
| PK Parameter | Mean | Std | Mean | Std | Mean | Std |
| $T_{max}$ (h)* | 0.250 | N/A | 0.25 | N/A | 0.375 | N/A |
| $C_{max}$ (ng/ml) | 0.654 | N/A | 7.22 | 8.18 | 0.971 | 0.380 |
| $AUC_{last}$ (h*ng/ml) | 0.0818 | N/A | 5.68 | 7.47 | 0.190 | 0.0491 |

*median values shown for $T_{max}$

It is clear from an inspection of the LBQ657 concentration-time profiles that those of compound I-1, compound I-2, and compound I-3 are flattened relative to AHU377 itself (Table 10). The corresponding increase in the LBQ657 $T_{max}$ values of compound I-1, compound I-2, and compound I-3 relative to AHU377, rather than the $T_{1/2}$ values, indicates that the flattening of the profiles is due to a prolonged absorption and/or LBQ657 formation rather than a decreased LBQ657 elimination. This is to be expected since regardless of the source of the LBQ657, once formed, its elimination should not be dependent on the identity of its precursor. The flattening of the LBQ657 profiles is especially pronounced for derivative compound I-1. It should also be noted that the LBQ657 exposure for compound I-1 (based on AUC values) did not decrease relative to that of AHU377. Thus, compound I-1 may offer a therapeutic advantage over AHU377 because it could require less frequent dosing due to its more prolonged exposure while at the same time having a reduced potential for Cmax-driving adverse effects. Another desirable feature of compound I-1, compound I-2, and compound I-3 is their nearly complete conversion to LBQ657 (unchanged parent drug and AHU377 present at only trace levels compared to LBQ657 levels, Table 11).

Example 14: Pharmacokinetics of Compounds I-1, I-2, I-3, I-4, I-5, I-6, I-7, I-8, I-9, I-10, I-11 and I-12

In other studies, the pharmacokinetics of the compounds of the disclosure in male Sprague Dawley rats was analyzed as follows:

Experiment Procedures for Compounds I-1, I-2, I-3 and I-4:

Test compound was dissolved or suspended in 0.5% HPC to a concentration of 0.5 mg/mL and given to SD rats (Male, 180-220 g, n=3) by gavage administration (10 mL/kg). Blood samples were collected at 0.25, 0.5, 1, 2, 4, 8, and 24 h after administration (anticoagulant: EDTA-Na$_2$). 200 µL of methanol: acetonitrile (1:1, v/v) with internal standard was added to 40 µL of plasma and vortexed thoroughly. After centrifugation for 5 min, 30 µL of the supernatant was mixed with 30 µL of water for HPLC-MS analysis. Samples were analyzed for the presence of the test compound and LBQ657 with an AB6500 triple quadrupole mass spectrometer (AB Sciex, USA) coupled to an ACQUITY UPLC BEH C$_{18}$ (1.7 µm, 2.0 mm×50 mm, Waters, USA) HPLC column. Gradient elution was applied consisting of ultrapure water containing 0.1% formic acid and acetonitrile containing 0.1% formic acid. The value of $AUC_{last}$ was calculated from the time-concentration curves for each animal using WinNonlin (CERTARA, USA). $C_{max}$ (the maximum plasma concentration) and $T_{max}$ (the time to reach the maximum plasma concentration) were determined by manual inspection of the time-concentration curves.

Experiment procedures for compounds I-5, I-6, I-7, I-8, I-9, I-10, I-11 and I-12:

Test compound (5 mg/kg) was dissolved or suspended in 0.5% HPC to a concentration of 0.5 mg/mL and administered to SD rats (Male, 180-220 g, n=3) by gavage administration (10 mL/kg). Blood samples were collected at 0.25, 0.5, 1, 2, 4, 8, and 24 h after administration (anticoagulant: EDTA-K$_2$). 50 µL of acetonitrile with internal standard was added to 10 µL of plasma and vortexed thoroughly. After centrifugation for 10 min, 35 µL of the supernatant was mixed with 35 µL of water for HPLC-MS analysis. Samples were analyzed for the presence of the test compound and LBQ657 with an AB3500 triple quadrupole mass spectrometer (AB Sciex, USA) coupled to an ACE UltraCore 2.5 SuperC$_{18}$ (50 mm×2.1 mm) HPLC column. Gradient elution was applied consisting of ultrapure water containing 0.1% formic acid and acetonitrile. The value of $AUC_{last}$ was calculated from the time-concentration curves for each animal using PKSolver. $C_{max}$ (the maximum plasma concentration) and $T_{max}$ (the time to reach the maximum plasma concentration) were determined by manual inspection of the time-concentration curves.

Results:

For each of the test compounds analyzed, the concentration of the test compound in plasma was found to be negligible and/or below the limit of quantitation over the entire time course monitored. The mean LBQ657 plasma pharmacokinetic parameters for each of the test compounds are listed in Table 13.

TABLE 13

Mean LBQ657 Pharmacokinetic Parameters

| Compound | Tmax (h) | Cmax (ng/mL) | AUClast (h*ng/mL) |
|---|---|---|---|
| I-1 | 0.5 | 858 | 1519 |
| I-2 | 0.5 | 970 | 1448 |
| I-3 | 0.5 | 1016 | 1415 |
| I-4 | 0.667 | 123 | 302 |
| I-5 | 0.417 | 1793 | 3138 |
| I-6 | 4.3 | 181 | 1627 |
| I-7 | 8 | 98 | 478 |
| I-8 | 5.3 | 42 | 345 |
| I-9 | 3.3 | 82 | 650 |
| I-10 | 0.67 | 1667 | 2847 |
| I-11 | 1 | 541 | 1321 |
| I-12 | 1.2 | 103 | 616 |

Example 15: Pharmacokinetics of Compound I-1 in Male Cynomolgus Monkeys

A cross-over study design consisting of two groups with two animals per group was conducted to examine the pharmacokinetic properties of compound I-1 of the present disclosure.

Compound I-1 and AHU377 were administered to each group as follows: compound I-1 on Day 0 followed by AHU377 on Day 2 (Group 1), AHU377 on Day 0 followed by compound I-1 on Day 2 (Group 2). Each animal received a single 10 mg/kg (5 ml/kg) oral gavage dose of the specified study drug on the specified day. The animals were 2.5 to 3.5 years of age and weighed between 3.1 and 4.3 kg at the beginning of the study. Both compounds were formulated in 0.5% methylcellulose (400 cp) and 0.1% Tween 80 (w,v) in water. Blood samples for pharmacokinetics analysis were collected at t=0, 0.25, 0.5, 1, 2, 4, 8, 24 and 48 hours post dose on Day 0 and Day 2. Plasma was prepared by collecting whole blood samples into tubes containing K$_2$EDTA and NaF (final concentrations: ~1 mg/mL (K₂EDTA) and ~2 mg/mL (NaF)). These tubes were kept in an ice bath prior to centrifugation at approximately 2,000 rcf for 10 minutes at approximately 5° C. To each resultant plasma sample (target volume 200 μL), 4 μL of 50% phosphoric acid (v/v) was added. In instances where the plasma sample volume differed significantly from the 200 μL target, the amount of phosphoric acid added was adjusted to maintain the same plasma:phosphoric acid ratio.

Under the conditions of this study, Compound I-1 and AHU377 dosed orally at 10 mg/kg as a single dose were well tolerated and did not result in any adverse clinical observations.

Bioanalytics:

[$^{13}C_4$]-LBQ657 was added as an internal standard to the pharmacokinetic (PK) samples and calibration standards prior to analysis by LC-MS/MS. The LC-MS system consisted of an API6500+ mass spectrometer coupled to an Agilent 1290 HPLC system equipped with a CTC Pal autosampler. The mass spectrometer was operated in the positive ion mode. For the chromatographic separations, an Acquity BEH C$^{18}$, 50×2.1 mm LC column was used with the solvent gradients displayed in Table 14 below:

TABLE 14

Solvent gradients used for chromatographic separations
% Solvent B = 100 - % Solvent A

| Time (min) | Compound I-1, AHU377, LBQ657 | Flowrate (μL/min) |
|---|---|---|
| 0.0 | 55 | 800 |
| 0.2 | 55 | 800 |
| 1.0 | 100 | 800 |
| 1.1 | 100 | 800 |
| 1.5 | 100 | 800 |
| 1.6 | 55 | 800 |
| 1.7 | 55 | 800 |

Solvent A = 5:95:0.1 (v:v:v) acetonitrile:water:formic acid
Solvent B = 50:50:0.1 (v:v:v) methanol:acetonitrile:water:formic acid The MS/MS mass transitions monitored for each analyte are shown in Table 15 below:

TABLE 15

MS/MS mass transitions monitored for each analyte

| Analyte | Precursor m/z | Product m/z |
|---|---|---|
| Compound I-1 | 525.4 | 394.2 |
| AHU377 | 412.4 | 266.1 |
| LBQ657 | 384.2 | 266.1 |
| [$^{13}C_4$]LBQ657 | 388.2 | 266.1 |

Figure 15:
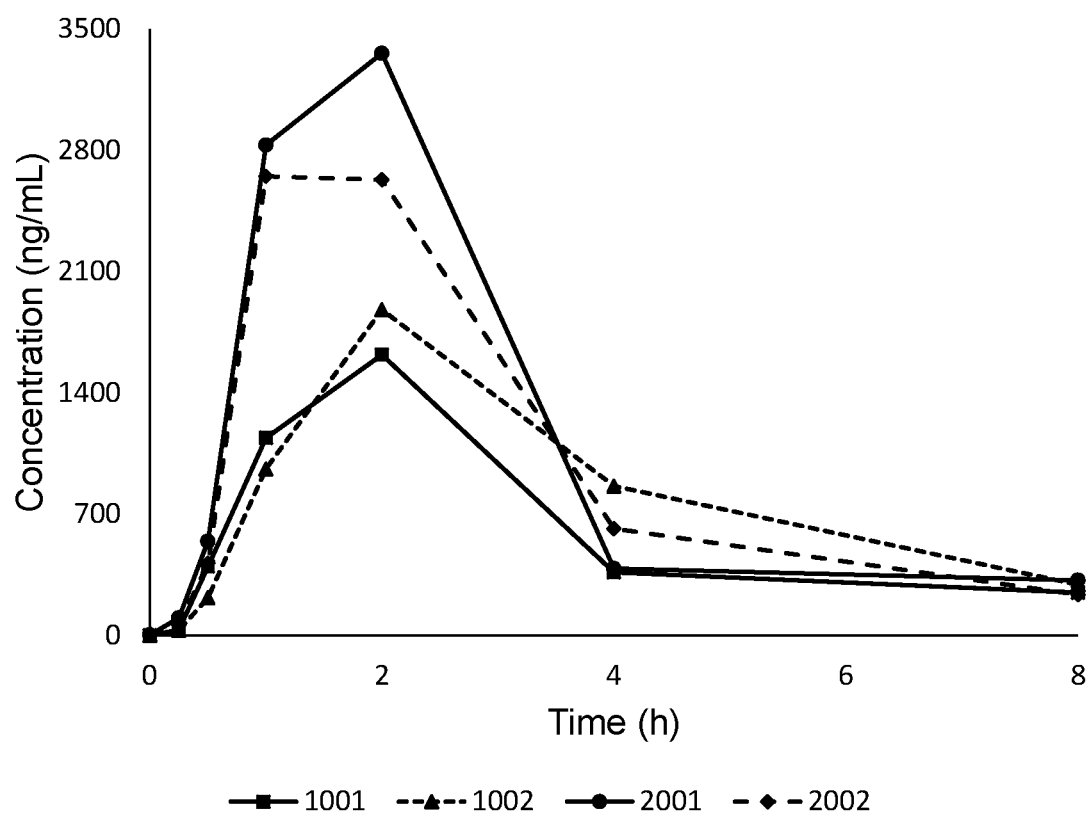
FIG. 15 is a graph showing the change in LBQ657 plasma concentration over 8 hours after dosing Monkeys with 10 mg/kg of compound I-1.

Pharmacokinetics:

The mean and individual pharmacokinetic concentration-time profiles of LBQ657 for dosing with compound I-1 over an 8 hour period from the total 24 hours collection period are displayed in FIG. 15.

Figure 16:
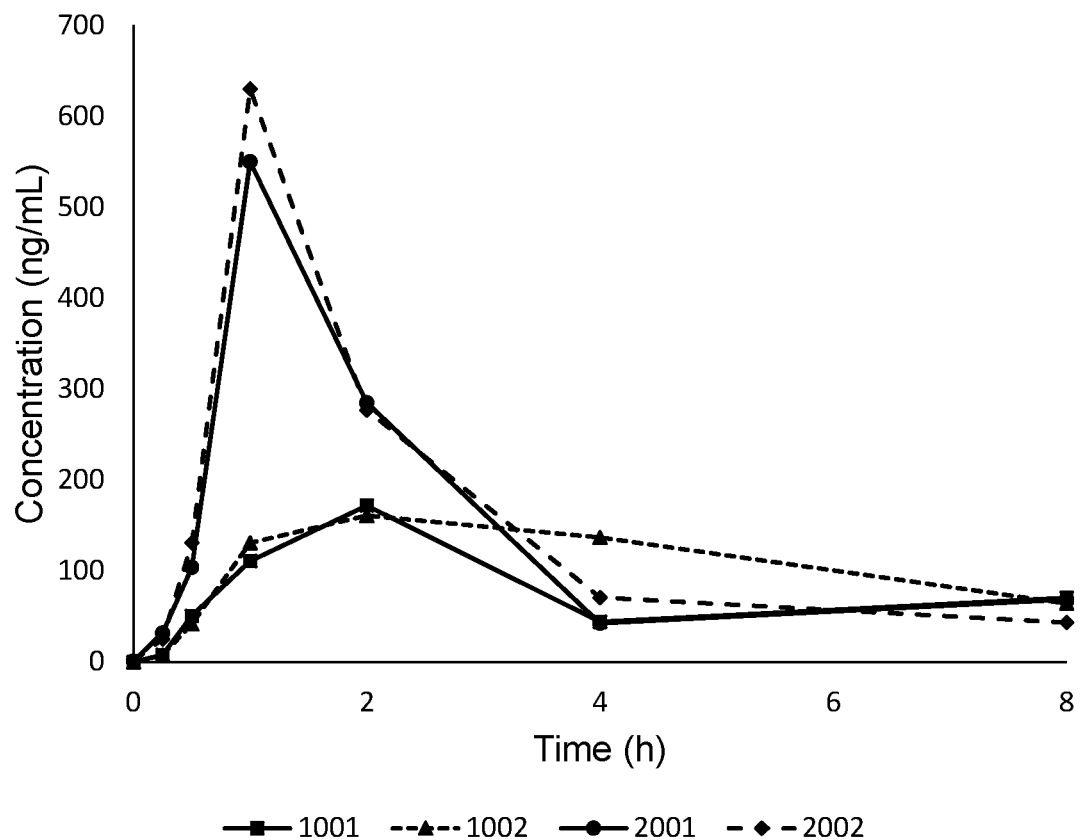
FIG. 16 is a graph showing the change in AHU377 plasma concentration over 8 hours after dosing Monkeys with 10 mg/kg of compound I-1.

The mean and individual pharmacokinetic concentration-time profiles of AHU377 for dosing with compound I-1 over an 8 hour period from the total 24 hours collection period are displayed in FIG. 16.

Figure 17:
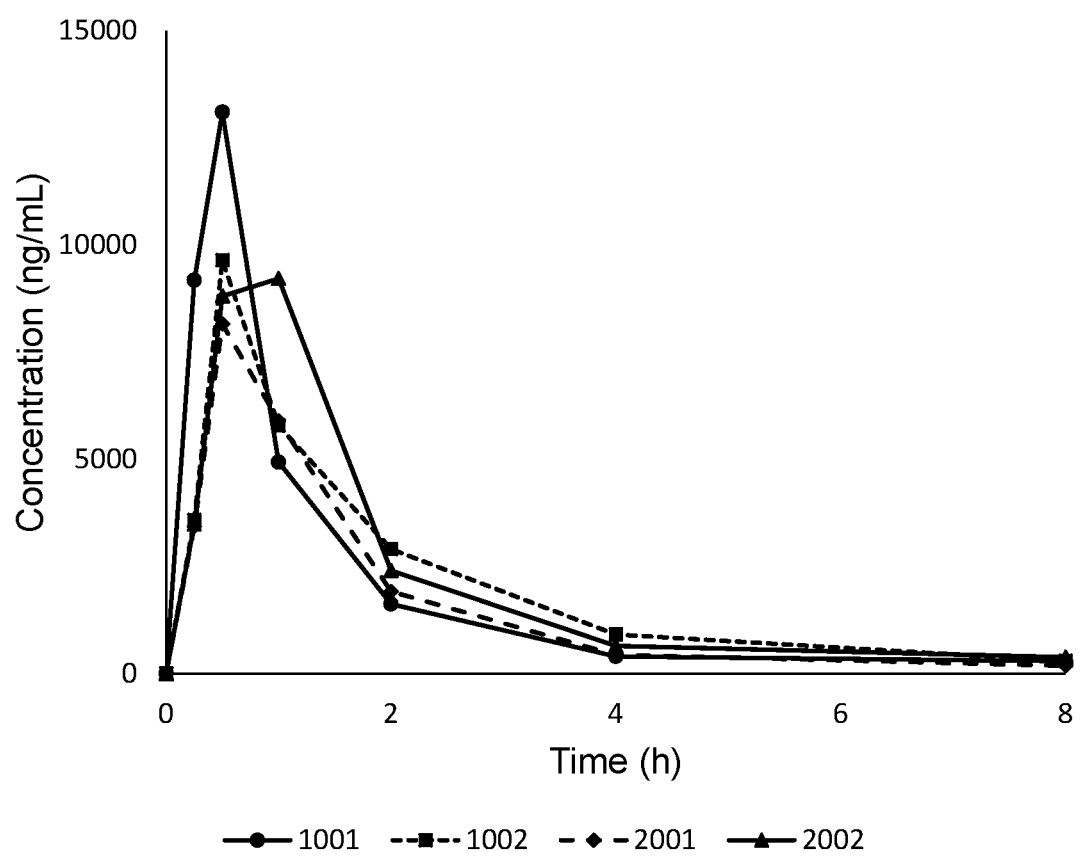
FIG. 17 is a graph showing the change in LBQ657 plasma concentration over 8 hours after dosing Monkeys with 10 mg/kg of AHU377.

The mean and individual pharmacokinetic concentration-time profiles of LBQ657 for dosing with AHU377 over an 8 hour period from the total 24 hours collection period are displayed in FIG. 17.

Figure 18:
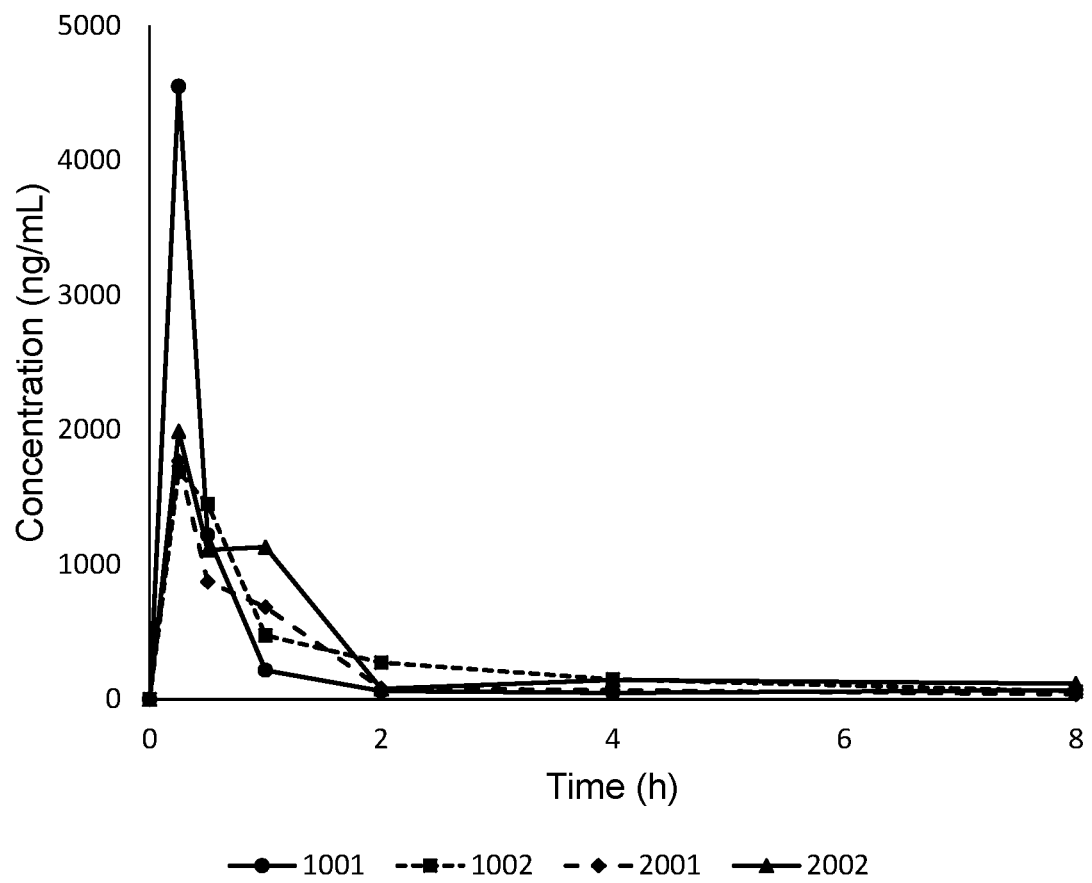
FIG. 18 is a graph showing the change in AHU377 plasma concentration over 8 hours after dosing Monkeys with 10 mg/kg of AHU377.

The mean and individual pharmacokinetic concentration-time profiles of AHU377 for dosing with AHU377 over an 8 hour period from the total 24 hours collection period are displayed in FIG. 18.

It should be noted that when dosing with compound I-1, the compound I-1 concentrations in plasma were below the lower limit of quantitation for all timepoints analyzed.

The pharmacokinetic parameters for AHU377 and LBQ657 following dosing with Compound I-1 and AHU377, estimated using non-compartmental analysis, are displayed in Tables 16 and 17.

TABLE 16

PK Parameters of LBQ657 and AHU377 following dosing with Compound I-1

| LBQ657 | Group 1 (Day 0) | | Group 2 (Day 2) | | | | |
|---|---|---|---|---|---|---|---|
| Monkey | 1001 | 1002 | 2001 | 2002 | mean | SD | % CV |
| 0 | 0 | 0 | 3.27 | 9.33 | 3.15 | 4.40 | 140 |
| 0.25 | 32.0 | 29.0 | 101 | 59.8 | 55.5 | 33.4 | 60.2 |
| 0.5 | 397 | 217 | 543 | 417 | 394 | 134 | 34.1 |
| 1 | 1140 | 961 | 2830 | 2650 | 1895 | 981 | 51.8 |
| 2 | 1620 | 1880 | 3360 | 2630 | 2373 | 785 | 33.1 |
| 4 | 364 | 862 | 386 | 616 | 557 | 233 | 41.8 |
| 8 | 247 | 293 | 318 | 235 | 273 | 38.9 | 14.2 |
| 24 | 66.8 | 23.5 | 18.6 | 69.8 | 44.7 | 27.4 | 61.3 |
| 48 | 7.90 | 12.3 | 1.33 | 13.0 | 8.63 | 5.37 | 62 |
| Cmax (ng/mL) | 1620 | 1880 | 3360 | 2650 | 2378 | 788 | 33.1 |
| Tmax (h) | 2 | 2 | 2 | 1 | 2 [1-2] | | |
| Tlast (h) | 48 | 48 | 48 | 48 | 48 [48-48] | | |
| AUClast (h*ng/mL) | 8435 | 9763 | 12120 | 11850 | 10542 | 1756 | 16.7 |
| AUCinf (h*ng/h) | 8526 | 9895 | 12130 | 12030 | 10645 | 175 | 16.4 |
| T1/2 (h) | 8.01 | 7.43 | 5.19 | 9.60 | 7.56 | 1.83 | 24.2 |
| T1/2 (range) | 4-48 | 4-48 | 4-48 | 8-48 | NA | NA | NA |
| Hydrolysis (%) | 87.1 | 87.1 | 87.5 | 87.2 | 87.2 | 0.173 | 0.198 |
| AHU377 | 1001 | 1002 | 2001 | 2002 | mean | SD | % CV |
| 0 | 0 | 0 | 1.03 | 1.35 | 0.595 | 0.699 | 118 |
| 0.25 | 7.92 | 7.61 | 31.8 | 25.2 | 18.1 | 12.3 | 67.7 |
| 0.5 | 50.8 | 41.9 | 104 | 131 | 81.9 | 42.7 | 52.1 |
| 1 | 111 | 131 | 550 | 630 | 356 | 273 | 76.8 |

TABLE 16-continued

PK Parameters of LBQ657 and AHU377 following dosing with Compound I-1

| 2 | 172 | 161 | 285 | 277 | 224 | 66.3 | 29.6 |
| --- | --- | --- | --- | --- | --- | --- | --- |
| 4 | 44.2 | 137 | 42.5 | 70.8 | 73.6 | 44.2 | 60.0 |
| 8 | 70.6 | 64.4 | 68.7 | 43.3 | 61.8 | 12.6 | 20.4 |
| 24 | 7.88 | 2.29 | 3.10 | 7.49 | 5.19 | 2.90 | 56.0 |
| 48 | 0 | 1.27 | 0 | 1.24 | 0.628 | 0.725 | 115 |
| Cmax (ng/mL) | 172 | 161 | 550 | 630 | 378 | 247 | 65.2 |
| Tmax (h) | 2 | 2 | 1 | 1 | 1.5 [1-2] | | |
| Tlast (h) | 24 | 48 | 24 | 48 | 36 [24-48] | | |
| AUClast (h*ng/mL) | 1260 | 1470 | 1730 | 1750 | 1553 | 233 | 15.0 |
| AUCinf (h*ng/h) | 1340 | 1490 | 1740 | 1770 | 1585 | 206 | 13.0 |
| T1/2 (h) | 6.88 | 6.43 | 3.91 | 7.57 | 6.20 | 1.60 | 25.7 |
| T1/2 (range) | 4-24 | 4-48 | 2-24 | 4-48 | NA | NA | NA |

TABLE 17

PK Parameters of LBQ657 and AHU377 following dosing with AHU377

| LBQ657 | Group 1 (Day 0) | | Group 2 (Day 2) | | | | |
| --- | --- | --- | --- | --- | --- | --- | --- |
| Monkey | 1001 | 1002 | 2001 | 2002 | mean | SD | %CV |
| 0 | 7.90 | 12.3 | 0 | 4.01 | 6.05 | 5.27 | 87.0 |
| 0.25 | 9180 | 3590 | 3440 | 3490 | 4925 | 2837 | 57.6 |
| 0.5 | 13100 | 9650 | 8160 | 8810 | 9930 | 2200 | 22.2 |
| 1 | 4940 | 5790 | 5900 | 9220 | 6463 | 1888 | 29.2 |
| 2 | 1630 | 2910 | 1920 | 2410 | 2218 | 563 | 25.4 |
| 4 | 408 | 920 | 443 | 654 | 606 | 236 | 38.9 |
| 8 | 298 | 305 | 191 | 391 | 296 | 81.9 | 27.7 |
| 24 | 57.9 | 33.8 | 13.8 | 54.4 | 40.0 | 20.4 | 51.1 |
| 48 | 7.11 | 1.86 | 3.27 | 9.33 | 5.39 | 3.44 | 63.7 |
| Cmax (ng/mL) | 13100 | 9650 | 8160 | 9220 | 10033 | 2139 | 21.3 |
| Tmax (h) | 0.5 | 0.5 | 0.5 | 1 | 0.5 [0.5-1] | | |
| Tlast (h) | 48 | 48 | 48 | 48 | 48 [48-48] | | |
| AUClast (h*ng/mL) | 18810 | 19730 | 14780 | 21780 | 18775 | 2938 | 15.7 |
| AUCinf (h*ng/h) | 18880 | 19750 | 14810 | 21880 | 18830 | 2962 | 15.7 |
| T1/2 (h) | 7.46 | 5.46 | 6.28 | 7.18 | 6.59 | 0.909 | 13.8 |
| T1/2 (range) | 4-48 | 8-48 | 4-48 | 4-48 | NA | NA | NA |
| Hydrolysis (%) | 86.7 | 87.4 | 87.8 | 85.7 | 86.9 | 0.907 | 1.04 |
| AHU377 | 1001 | 1002 | 2001 | 2002 | mean | SD | % CV |
| 0 | 0 | 1.27 | 0 | 0 | 0.318 | 0.635 | 200 |
| 0.25 | 4550 | 1690 | 1770 | 1990 | 2500 | 1373 | 54.9 |
| 0.5 | 1220 | 1450 | 874 | 1110 | 1164 | 239 | 20.6 |
| 1 | 216 | 475 | 685 | 1130 | 627 | 387 | 61.7 |
| 2 | 62.0 | 274 | 82.8 | 78.1 | 124 | 100 | 80.7 |
| 4 | 48.7 | 149 | 68.1 | 144 | 102 | 51.5 | 50.3 |
| 8 | 69.5 | 58.3 | 37.4 | 117 | 70.6 | 33.7 | 47.8 |
| 24 | 8.93 | 5.09 | 2.37 | 7.04 | 5.86 | 2.80 | 47.9 |
| 48 | 1.16 | 0 | 1.03 | 1.35 | 0.885 | 0.604 | 68.3 |
| Cmax (ng/mL) | 4550 | 1690 | 1770 | 1990 | 2500 | 1373 | 54.9 |
| Tmax (h) | 0.25 | 0.25 | 0.25 | 0.25 | 0.25 [0.25-0.25] | | |
| Tlast (h) | 48 | 24 | 24 | 48 | 36 [24-48] | | |
| AUClast (h*ng/mL) | 2880 | 2800 | 2050 | 3640 | 2843 | 650 | 22.9 |
| AUCinf (h*ng/h) | 2900 | 2840 | 2060 | 3650 | 2863 | 650 | 22.7 |
| T1/2 (h) | 6.87 | 4.22 | 6.89 | 6.26 | 6.06 | 1.26 | 20.8 |
| T1/2 (range) | 8-48 | 4-24 | 2-48 | 4-48 | NA | NA | NA |

The mean AUC of LBQ657 following dosing with compound I-1 and AHU377 was 10,542 h*ng/mL and 18,775 h*ng/mL; respectively. Additionally, the mean Cmax of LBQ657 following dosing with compound I-1 and AHU377 was 2,378 ng/mL and 10,033 ng/mL; respectively. Accounting for the differences in molecular weight between compound I-1 (524.7 amu) and AHU375 (411.5), the relative bioavailability of compound I-1 compared to AHU377 was 72% based on AUC values and 30% based on Cmax values; when compared on an equimolar dosing basis. The decreased LBQ657 Cmax/AUC ratio for compound I-1 compared to AHU377 suggests a flattening of the LBQ657 concentration-time profile for compound I-1 compared to AHU377. This conclusion is further supported by the observation that the median Tmax of LBQ657 following dosing with compound I-1 (2 h) occurred later than the median Tmax of LBQ657 following dosing with AHU377 (0.5 h). Thus, compound I-1 may offer a therapeutic advantage over AHU377 since its flatter profiles may reduce the potential for Cmax-driven adverse effects.

Example 16: In Vivo Efficacy Study on Blood Pressure in DSS Rats

An in vivo study ascertains the effects on blood pressure in DSS (Dahl Salt Sensitive) rats. The DSS hypertensive rat model is a model of hypertension that is sensitive to dietary salt (NaCl), see for example Rapp (1982) Hypertension 4:753-763 and Hegde et al. BMC Pharmacology 2011, 11 (Suppl 1):P33. Under pentobarbital sodium anesthesia, a DSI (Data Sciences International, St. Paul, Minn.) telemetric probe is implanted. The transducer is inserted into abdominal aorta, and the transmitter is implanted into abdominal cavity.

During postoperative recovery period, close observation is performed. Analgesics (Buprenorphine, 0.1-0.5 mg/kg, once per day for 1 day) and preventive antibiotics (Cephradine, 10~15 mg/kg, ip., once per day for 3 days) are administered on a daily basis.

Before the treatment period, all animals are fed with 8% high salt food for about 2 weeks. Test compound is formulated in 0.5% HPC and administered by oral gavage.

Five groups of animals are treated as follows:
1. Vehicle, 0.5% HPC, QD, PO, N=5
2. Valsartan, 30 mg/kg, QD, PO, N=5
3. Compound I-1, 50 mg/kg, QD, PO, N=6
4. Compound I-1, 15 mg/kg+Valsartan, 30 mg/kg, QD, PO, N=5
5. Compound I-1, 50 mg/kg+Valsartan, 30 mg/kg, QD, PO, N=5

N is the number of animals. The mean arterial pressure, systolic pressure, diastolic pressure and heart rate after administration for each animal are measured.

Interim results obtained before full study completion are shown in Tables 18 and 19 (full cohort of animals beyond day 7 were reduced due to some loss). Mean measurements of the systolic (Table 18) and diastolic (Table 19) blood pressures, for the baseline day prior to first treatment and for treatment days 1 and 7 only, in each treatment group, are shown. Measurements obtained every other hour only are shown.

TABLE 18

| | Systolic blood pressure measurements at specified time points | | | | | | | | | |
|---|---|---|---|---|---|---|---|---|---|---|
| | Vehicle | | Valsartan 30 mg/kg | | Compound I-1 50 mg/kg | | Compound I-1 15 mg/kg + Valsartan 30 mg/kg | | Compound I-1 50 mg/kg + Valsartan 30 mg/kg | |
| | Mean (N = 5) | SEM | Mean (N = 5) | SEM | Mean (N = 6) | SEM | Mean (N = 5) | SEM | Mean (N = 5) | SEM |
| Baseline day | | | | | | | | | | |
| Hour 1 | 162.75 | 4.47 | 157.31 | 2.83 | 163.63 | 3.00 | 154.84 | 3.90 | 168.11 | 6.27 |
| Hour 3 | 156.53 | 6.05 | 154.77 | 5.11 | 159.24 | 4.32 | 153.45 | 5.29 | 167.17 | 6.26 |
| Hour 5 | 157.16 | 4.38 | 151.17 | 3.13 | 155.66 | 3.93 | 153.43 | 5.33 | 166.06 | 6.26 |
| Hour 7 | 154.49 | 5.32 | 154.26 | 4.77 | 154.92 | 4.42 | 156.22 | 5.00 | 165.97 | 6.25 |
| Hour 9 | 159.95 | 4.26 | 160.88 | 4.78 | 157.92 | 2.33 | 156.83 | 4.71 | 164.27 | 5.58 |
| Hour 11 | 164.87 | 4.62 | 163.83 | 4.73 | 162.87 | 2.38 | 161.36 | 4.86 | 168.16 | 6.66 |
| Hour 13 | 167.16 | 3.76 | 164.35 | 4.72 | 167.91 | 2.31 | 165.68 | 3.92 | 172.66 | 7.44 |
| Hour 15 | 168.30 | 4.58 | 163.94 | 5.90 | 167.33 | 3.96 | 166.98 | 3.74 | 175.29 | 8.10 |
| Hour 17 | 169.88 | 3.04 | 164.12 | 6.12 | 167.09 | 2.55 | 167.77 | 4.95 | 172.83 | 7.76 |
| Hour 19 | 171.94 | 2.63 | 166.66 | 5.38 | 169.48 | 4.22 | 168.20 | 3.22 | 174.15 | 7.93 |
| Hour 21 | 169.41 | 3.87 | 166.05 | 5.46 | 169.41 | 1.84 | 164.88 | 2.53 | 175.54 | 8.00 |
| Hour 23 | 166.59 | 2.74 | 162.95 | 5.13 | 161.71 | 1.16 | 163.23 | 5.40 | 171.99 | 6.67 |

TABLE 18-continued

Systolic blood pressure measurements at specified time points

| | Vehicle | | Valsartan 30 mg/kg | | Compound I-1 50 mg/kg | | Compound I-1 15 mg/kg + Valsartan 30 mg/kg | | Compound I-1 50 mg/kg + Valsartan 30 mg/kg | |
|---|---|---|---|---|---|---|---|---|---|---|
| | Mean (N = 5) | SEM | Mean (N = 5) | SEM | Mean (N = 6) | SEM | Mean (N = 5) | SEM | Mean (N = 5) | SEM |
| Dosing day 1 | | | | | | | | | | |
| Hour 1 | 169.33 | 3.74 | 159.22 | 5.73 | 164.94 | 2.54 | 160.52 | 4.60 | 166.84 | 8.25 |
| Hour 3 | 159.51 | 4.07 | 149.24 | 5.87 | 152.46 | 3.53 | 140.97 | 6.09 | 152.72 | 7.49 |
| Hour 5 | 160.69 | 5.68 | 152.75 | 5.21 | 155.79 | 4.00 | 146.02 | 4.34 | 156.32 | 6.39 |
| Hour 7 | 166.14 | 4.72 | 160.54 | 5.33 | 159.33 | 4.51 | 155.46 | 4.22 | 162.61 | 7.77 |
| Hour 9 | 172.89 | 4.86 | 165.09 | 4.98 | 166.16 | 4.45 | 162.88 | 4.23 | 166.61 | 9.09 |
| Hour 11 | 176.77 | 4.94 | 166.16 | 5.70 | 168.46 | 4.30 | 164.59 | 4.60 | 170.98 | 9.28 |
| Hour 13 | 179.12 | 4.81 | 162.84 | 5.13 | 169.35 | 5.76 | 167.29 | 4.93 | 171.70 | 10.27 |
| Hour 15 | 177.98 | 3.87 | 162.88 | 4.92 | 169.78 | 4.96 | 170.79 | 5.88 | 168.57 | 6.70 |
| Hour 17 | 181.01 | 3.77 | 169.80 | 5.36 | 174.28 | 4.28 | 168.34 | 3.11 | 172.72 | 8.09 |
| Hour 19 | 169.56 | 4.73 | 162.27 | 6.59 | 166.11 | 2.60 | 157.47 | 3.31 | 166.26 | 7.82 |
| Hour 21 | 174.77 | 4.35 | 163.01 | 4.38 | 162.24 | 3.27 | 151.99 | 6.61 | 166.23 | 7.04 |
| Hour 23 | 167.43 | 5.44 | 155.05 | 4.64 | 158.31 | 3.38 | 146.72 | 6.10 | 161.22 | 9.09 |
| Dosing day 7 | | | | | | | | | | |
| Hour 1 | 175.28 | 4.37 | 165.60 | 3.56 | 167.78 | 6.52 | 146.72 | 6.10 | 161.22 | 9.09 |
| Hour 3 | 165.49 | 4.17 | 143.04 | 6.53 | 158.75 | 5.60 | 159.41 | 8.46 | 148.38 | 5.08 |
| Hour 5 | 168.41 | 4.84 | 142.52 | 9.79 | 156.95 | 6.02 | 142.45 | 9.25 | 129.39 | 3.34 |
| Hour 7 | 177.07 | 4.78 | 153.17 | 7.12 | 165.23 | 6.69 | 144.11 | 8.79 | 137.33 | 3.87 |
| Hour 9 | 183.79 | 6.02 | 170.26 | 2.84 | 176.77 | 4.62 | 148.96 | 10.32 | 150.04 | 4.80 |
| Hour 11 | 191.11 | 6.05 | 173.95 | 3.84 | 182.56 | 4.29 | 170.65 | 5.87 | 154.49 | 5.07 |
| Hour 13 | 192.89 | 6.32 | 175.24 | 6.46 | 182.29 | 7.11 | 174.44 | 7.03 | 144.73 | 5.24 |
| Hour 15 | 191.00 | 5.50 | 177.02 | 3.78 | 175.64 | 7.36 | 176.47 | 7.02 | 153.05 | 4.34 |
| Hour 17 | 192.05 | 7.24 | 176.02 | 5.84 | 179.39 | 5.05 | 176.33 | 5.28 | 160.87 | 7.39 |
| Hour 19 | 191.09 | 7.54 | 176.83 | 4.92 | 175.46 | 7.18 | 175.78 | 6.68 | 152.54 | 4.29 |
| Hour 21 | 182.61 | 6.94 | 164.22 | 4.46 | 165.83 | 8.95 | 176.88 | 7.19 | 151.80 | 2.78 |
| Hour 23 | 181.34 | 5.25 | 163.41 | 4.20 | 170.13 | 6.40 | 156.55 | 7.80 | 145.54 | 7.49 |

TABLE 19

| | Diastolic blood pressure measurements at specified time points | | | | | | | | | |
|---|---|---|---|---|---|---|---|---|---|---|
| | Vehicle | | Valsartan 30 mg/kg | | Compound I-1 50 mg/kg | | Compound I-1 15 mg/kg + Valsartan 30 mg/kg | | Compound I-1 50 mg/kg + Valsartan 30 mg/kg | |
| | Mean (N = 5) | SEM | Mean (N = 5) | SEM | Mean (N = 6) | SEM | Mean (N = 5) | SEM | Mean (N = 5) | SEM |
| Baseline day | | | | | | | | | | |
| Hour 1 | 109.32 | 4.25 | 106.03 | 3.51 | 111.95 | 2.69 | 105.32 | 3.26 | 115.12 | 6.60 |
| Hour 3 | 102.25 | 5.40 | 102.82 | 5.86 | 107.76 | 4.20 | 102.94 | 4.06 | 112.69 | 6.96 |
| Hour 5 | 102.40 | 3.97 | 100.19 | 3.25 | 104.17 | 3.75 | 102.58 | 4.46 | 112.26 | 7.46 |
| Hour 7 | 99.19 | 4.98 | 103.02 | 5.37 | 102.18 | 4.82 | 104.66 | 4.85 | 111.80 | 7.39 |
| Hour 9 | 105.31 | 3.36 | 110.48 | 5.50 | 105.63 | 2.11 | 106.44 | 4.24 | 110.27 | 5.55 |
| Hour 11 | 110.76 | 3.80 | 114.29 | 5.57 | 111.89 | 1.68 | 112.32 | 3.54 | 114.81 | 5.76 |
| Hour 13 | 114.49 | 3.15 | 115.22 | 5.77 | 116.86 | 2.06 | 115.48 | 3.58 | 118.68 | 7.24 |
| Hour 15 | 115.51 | 4.03 | 113.98 | 6.65 | 115.85 | 2.34 | 116.25 | 3.73 | 120.91 | 7.92 |
| Hour 17 | 116.46 | 2.79 | 114.14 | 6.14 | 116.42 | 1.08 | 116.69 | 4.59 | 119.00 | 7.29 |
| Hour 19 | 117.94 | 2.43 | 116.35 | 5.80 | 117.36 | 1.63 | 117.28 | 3.31 | 119.58 | 7.31 |
| Hour 21 | 115.57 | 3.62 | 116.78 | 5.33 | 116.95 | 1.90 | 115.53 | 2.82 | 120.55 | 7.93 |
| Hour 23 | 111.38 | 2.69 | 111.79 | 6.13 | 109.93 | 2.27 | 113.08 | 5.25 | 117.35 | 7.18 |
| Dosing day 1 | | | | | | | | | | |
| Hour 1 | 114.34 | 3.51 | 107.73 | 4.65 | 115.05 | 0.88 | 112.73 | 4.76 | 114.10 | 7.25 |
| Hour 3 | 104.82 | 4.32 | 101.25 | 5.48 | 106.99 | 1.79 | 101.48 | 2.75 | 103.46 | 5.65 |
| Hour 5 | 102.90 | 4.44 | 98.63 | 5.61 | 104.66 | 1.86 | 98.20 | 4.91 | 101.51 | 6.67 |
| Hour 7 | 104.40 | 5.13 | 100.29 | 5.00 | 106.82 | 2.19 | 96.89 | 3.13 | 101.72 | 6.41 |
| Hour 9 | 109.50 | 4.69 | 109.35 | 4.47 | 108.88 | 2.25 | 106.00 | 4.12 | 108.76 | 6.65 |
| Hour 11 | 118.18 | 4.28 | 115.04 | 4.30 | 114.90 | 2.60 | 112.33 | 3.39 | 112.72 | 7.52 |
| Hour 13 | 121.99 | 4.52 | 116.06 | 4.18 | 116.00 | 2.85 | 114.05 | 4.04 | 115.58 | 8.24 |
| Hour 15 | 123.82 | 4.52 | 113.61 | 3.85 | 117.42 | 3.62 | 117.38 | 4.42 | 117.20 | 8.72 |
| Hour 17 | 122.77 | 3.13 | 112.82 | 3.84 | 118.42 | 2.76 | 121.33 | 4.80 | 113.92 | 6.74 |
| Hour 19 | 125.81 | 3.40 | 119.69 | 4.70 | 122.21 | 2.55 | 118.26 | 3.06 | 119.09 | 7.89 |
| Hour 21 | 115.11 | 4.46 | 112.65 | 5.30 | 115.68 | 2.55 | 108.43 | 3.94 | 112.25 | 8.51 |
| Hour 23 | 119.64 | 3.74 | 112.26 | 4.36 | 111.09 | 2.19 | 103.20 | 6.56 | 111.57 | 7.21 |
| Dosing day 7 | | | | | | | | | | |
| Hour 1 | 120.26 | 4.77 | 113.86 | 3.43 | 118.61 | 4.65 | 110.26 | 5.78 | 98.14 | 5.60 |
| Hour 3 | 109.01 | 5.02 | 94.17 | 4.68 | 109.11 | 4.43 | 97.10 | 5.92 | 81.46 | 3.21 |
| Hour 5 | 112.21 | 5.28 | 93.33 | 7.40 | 108.96 | 5.68 | 97.69 | 5.77 | 88.43 | 4.38 |
| Hour 7 | 119.29 | 4.79 | 102.69 | 5.83 | 114.22 | 6.67 | 100.63 | 7.42 | 98.29 | 5.37 |
| Hour 9 | 127.12 | 5.79 | 117.65 | 3.13 | 126.44 | 4.24 | 121.17 | 4.82 | 102.23 | 3.50 |
| Hour 11 | 133.89 | 5.91 | 123.73 | 3.81 | 129.02 | 4.63 | 125.71 | 5.82 | 95.34 | 4.04 |
| Hour 13 | 135.27 | 6.50 | 125.63 | 5.01 | 131.34 | 6.70 | 127.14 | 5.61 | 102.16 | 4.60 |
| Hour 15 | 133.86 | 5.59 | 126.20 | 4.43 | 126.20 | 5.02 | 127.80 | 4.86 | 109.11 | 8.75 |

TABLE 19-continued

Diastolic blood pressure measurements at specified time points

|  | Vehicle | | Valsartan 30 mg/kg | | Compound I-1 50 mg/kg | | Compound I-1 15 mg/kg + Valsartan 30 mg/kg | | Compound I-1 50 mg/kg + Valsartan 30 mg/kg | |
| --- | --- | --- | --- | --- | --- | --- | --- | --- | --- | --- |
|  | Mean (N = 5) | SEM | Mean (N = 5) | SEM | Mean (N = 6) | SEM | Mean (N = 5) | SEM | Mean (N = 5) | SEM |
| Hour 17 | 134.85 | 7.52 | 124.23 | 5.26 | 127.80 | 4.54 | 127.33 | 6.00 | 100.05 | 4.85 |
| Hour 19 | 136.16 | 7.79 | 127.67 | 4.55 | 124.88 | 5.59 | 129.04 | 5.87 | 102.11 | 4.52 |
| Hour 21 | 126.12 | 7.63 | 112.77 | 4.47 | 116.93 | 8.17 | 107.32 | 5.87 | 94.76 | 7.21 |
| Hour 23 | 126.51 | 4.99 | 112.12 | 2.95 | 120.18 | 5.86 | 108.50 | 6.17 | 88.98 | 7.82 |

The results show a trend for lower blood pressure in the animals treated with compound I-1 alone, valsartan alone or compound I-1 in combination with valsartan, as compared to animals treated with vehicle alone.

In the group treated with compound I-1 50 mg/kg in combination with Valsartan 30 mg/kg, the blood pressure lowering trend was observed to generally be more profound than in the groups dosed with compound I-1 alone or valsartan alone.

Thus, the results demonstrate the blood pressure lowering (antihypertensive) effects of compound I-1 of the present disclosure alone and when in combination with valsartan.

Advantageous Properties of Compound I-1

The free form of AHU377 is amorphous, and typically obtained as an oil. Compound I-1 is highly crystalline as free form possessing improved stability, hygroscopicity and pharmaceutical processability as compared to AHU377. The crystalline free form of compound I-1 showed significantly improved bulk stability. Negligible degradation of compound I-1 was observed after 1 week of exposure at stress conditions (50° C., 80° C. and 50° C./75% RH), whereas AHU377-NX showed 0.29%, 26.59% and 4.07% of degradation when exposed to 50° C., 80° C. and 50° C./75% RH respectively for the same time period.

Compound I-1 also showed significantly improved solution stability. It was stable at pH of 4.7 and pH of 6.8 up to 70° C. for 3 days. On the other hand, significantly degradation of AHU377 was observed at a pH of 4.7 at day 1 (2.63% at 70° C.). Both compound I-1 and AHU377 were unstable under acidic conditions (i.e., pH of 2.0), but compound I-1 appeared to be more stable than AHU377. For example, compound I-1 showed 18.27% degradation at 70° C. at day 1, while AHU377 showed 21.49% degradation under the same conditions.

Compound I-1 also demonstrated significantly improved hygroscopicity compared to AHU377. The weight gain of compound I-1 after exposure to 90% RH (relatively humidity) was 0.34%, while that of AHU377 under the same conditions was 3.4%. Moreover, compound I-1 showed powder-like appearance and good flowability, which is favorable for pharmaceutical processing. On the other hand, AHU377 is a wax-like solid, which needs to be properly processed before further pharmaceutical processing such as weighing, dispensing and filling.

Advantageous Properties of Compound I-2

Compound I-2 showed medium to high crystallinity (both forms), which offers improved stability and pharmaceutical processability. The crystalline free form of compound I-2 showed significantly improved bulk stability. Both crystalline forms of compound I-2 were stable after 1 week of exposure to stress conditions (50° C., 80° C. and 50° C./75% RH), whereas AHU377 showed 0.29%, 26.59% and 4.07% degradation when exposed to 50° C., 80° C. and 50° C./75% RH respectively for the same time period. Moreover, both crystalline forms of compound I-2 showed powder-like appearance and good flowability, property that is highly favorable for pharmaceutical processing. By comparison, AHU377 is a wax-like solid, which needs to be properly processed before further pharmaceutical processing such as weighing, dispensing and filling.

An additional advantage observed is that compound I-2 demonstrated extremely high aqueous solubility, possibly due to its zwitterionic nature. The solubility value was more than about 500 mg/ml based on visual observation.

Advantageous Properties of Compound I-3

Even though the free form of compound I-3 was amorphous oil, the fumarate, succinate and malonate salts of compound I-3 were crystalline. All three salts of Compound I-3 (e.g., fumarate, succinate and malonate) showed powder-like appearance and good flowability. The crystalline fumarate salt of compound I-3 showed improved stability compared to AHU377. The crystalline fumarate salt of compound I-3 was stable after 1 week of exposure to various stress conditions (i.e., 50° C., 80° C. and 50° C./75% RH).

It can be seen that the compounds of the disclosure are useful as inhibitors of Neutral endopeptidase activity and therefore useful in the treatment of diseases and conditions associated with Neutral endopeptidase activity such as the diseases disclosed herein.

Additionally, the compounds of the disclosure provide prolonged exposure requiring less frequent dosing and reduced potential for Cmax-driving adverse effects.

It will be understood that the disclosure has been described by way of example only and modifications may be made whilst remaining within the scope and spirit of the disclosure.

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A method of inhibiting neutral endopeptidase activity in a subject in need thereof, comprising: administering to the subject a therapeutically effective amount of a compound of the Formula (I):

(I)

wherein:
- $R^1$ is H or $(C_1-C_4)$alkyl;
- $R^2$ is H, $(C_1-C_4)$alkyl, $(C_6-C_{10})$ aryl, or 5- or 6-membered heteroaryl comprising 1-3 heteroatoms selected from N, S, and O, wherein the alkyl is optionally substituted with one or more $R^3$, and wherein the aryl and heteroaryl are optionally substituted with one or more $R^4$;
- each $R^3$ is independently at each occurrence —$NH_2$, $(C_1-C_4)$alkylamino, $(C_1-C_4)$dialkylamino, —OH, —SH, —S$(C_1-C_4)$alkyl, —$CO_2H$, —$CONH_2$, —NHC(NH)$NH_2$, $(C_6-C_{10})$ aryl, or 5- to 10-membered monocyclic or bicyclic heteroaryl comprising 1-3 heteroatoms selected from N, O, and S, wherein the aryl and heteroaryl are optionally substituted with one or more $R^5$;
- each $R^4$ is independently at each occurrence $(C_1-C_4)$ alkyl, $(C_1-C_4)$haloalkyl, $(C_1-C_4)$alkoxy, $(C_1-C_4)$haloalkoxy, halogen, —$NH_2$, —OH, or CN; and
- each $R^5$ is independently at each occurrence $(C_1-C_4)$ alkyl, $(C_1-C_4)$haloalkyl, $(C_1-C_4)$alkoxy, $(C_1-C_4)$haloalkoxy, halogen, —$NH_2$, —OH, or CN;

or a pharmaceutically acceptable salt thereof;

wherein the compound of Formula (I), or a pharmaceutically acceptable salt thereof, is administered together, concomitantly or sequentially with an Angiotensin Receptor Blocker selected from candesartan, losartan, irbesartan, telmisartan, olmesartan, eprosartan, fimasartan, and azilsartan, or a pharmaceutically acceptable salt thereof.

2. The method according to claim 1, wherein the compound is of Formula (II):

(II)

or a pharmaceutically acceptable salt thereof.

3. The method according to claim 1, wherein $R^1$ is H, ethyl, or t-butyl.

4. The method according to claim 1, wherein $R^2$ is H or $(C_1-C_4)$alkyl optionally substituted with one to two $R^3$.

5. The method according to claim 1, wherein $R^2$ is H or $(C_1-C_4)$alkyl optionally substituted with —$NH_2$.

6. The method according to claim 1, wherein $R^1$ is H, ethyl, or t-butyl, and $R^2$ is H or $(C_4)$alkyl optionally substituted with —$NH_2$.

7. The method according to claim 1, wherein the compound is selected from:
- (4-(((2S,4R)-1-([1,1'-biphenyl]-4-yl)-5-ethoxy-4-methyl-5-oxopentan-2-yl)amino)-4-oxobutanoyl)-L-leucine;
- (4-(((2S,4R)-1-([1,1'-biphenyl]-4-yl)-5-ethoxy-4-methyl-5-oxopentan-2-yl)amino)-4-oxobutanoyl)-L-lysine; and
- tert-butyl (4-(((2S,4R)-1-([1,1'-biphenyl]-4-yl)-5-ethoxy-4-methyl-5-oxopentan-2-yl)amino)-4-oxobutanoyl)-L-lysinate;
- ethyl (2R,4S)-5-([1,1'-biphenyl]-4-yl)-4-(4-(((S)-1-ethoxy-4-methyl-1-oxopentan-2-yl)amino)-4-oxobutanamido)-2-methylpentanoate;
- (4-(((2S,4R)-1-([1,1'-biphenyl]-4-yl)-5-ethoxy-4-methyl-5-oxopentan-2-yl)amino)-4-oxobutanoyl)-L-arginine;
- (4-(((2S,4R)-1-([1,1'-biphenyl]-4-yl)-5-ethoxy-4-methyl-5-oxopentan-2-yl)amino)-4-oxobutanoyl)-L-histidine;
- (4-(((2S,4R)-1-([1,1'-biphenyl]-4-yl)-5-ethoxy-4-methyl-5-oxopentan-2-yl)amino)-4-oxobutanoyl)glycine;
- (4-(((2S,4R)-1-([1,1'-biphenyl]-4-yl)-5-ethoxy-4-methyl-5-oxopentan-2-yl)amino)-4-oxobutanoyl)-L-alanine;
- (4-(((2S,4R)-1-([1,1'-biphenyl]-4-yl)-5-ethoxy-4-methyl-5-oxopentan-2-yl)amino)-4-oxobutanoyl)-L-valine;
- (4-(((2S, 4R)-1-([1,1'-biphenyl]-4-yl)-5-ethoxy-4-methyl-5-oxopentan-2-yl)amino)-4-oxobutanoyl)-L-phenylalanine;
- (4-(((2S,4R)-1-([1,1'-biphenyl]-4-yl)-5-ethoxy-4-methyl-5-oxopentan-2-yl)amino)-4-oxobutanoyl)-L-tryptophan; and
- (4-(((2S,4R)-1-([1,1'-biphenyl]-4-yl)-5-ethoxy-4-methyl-5-oxopentan-2-yl)amino)-4-oxobutanoyl)-L-isoleucine;

or a pharmaceutically acceptable salt thereof.

8. The method according to claim 1, wherein the compound is (4-(((2S,4R)-1-([1,1'-biphenyl]-4-yl)-5-ethoxy-4- methyl-5-oxopentan-2-yl)amino)-4-oxobutanoyl)-L-leucine or a pharmaceutically acceptable salt thereof.

9. The method according to claim 1, wherein the compound is (4-(((2S,4R)-1-([1,1'-biphenyl]-4-yl)-5-ethoxy-4-methyl-5-oxopentan-2-yl)amino)-4-oxobutanoyl)-L-histidine or a pharmaceutically acceptable salt thereof.

10. A method of treating a disorder or a disease associated with neutral endopeptidase activity in a subject in need thereof, comprising: administering to the subject a therapeutically effective amount of a compound of the Formula (I):

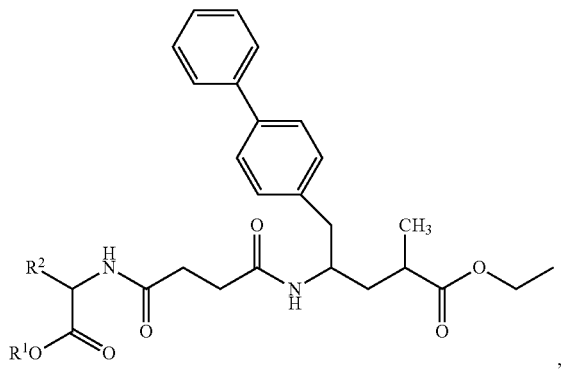

(I)

wherein:
- $R^1$ is H or $(C_1-C_4)$alkyl;
- $R^2$ is H, $(C_1-C_4)$alkyl, $(C_6-C_{10})$ aryl, or 5- or 6-membered heteroaryl comprising 1-3 heteroatoms selected from N, S, and O, wherein the alkyl is optionally substituted with one or more $R^3$, and wherein the aryl and heteroaryl are optionally substituted with one or more $R^4$;
- each $R^3$ is independently at each occurrence —$NH_2$, $(C_1-C_4)$alkylamino, $(C_1-C_4)$dialkylamino, —OH, —SH, —S($C_1-C_4$)alkyl, —$CO_2H$, —$CONH_2$, —NHC(NH)$NH_2$, $(C_6-C_{10})$ aryl, or 5- to 10-membered monocyclic or bicyclic heteroaryl comprising 1-3 heteroatoms selected from N, O, and S, wherein the aryl and heteroaryl are optionally substituted with one or more $R^5$;
- each $R^4$ is independently at each occurrence $(C_1-C_4)$ alkyl, $(C_1-C_4)$haloalkyl, $(C_1-C_4)$alkoxy, $(C_1-C_4)$haloalkoxy, halogen, —$NH_2$, —OH, or CN; and
- each $R^5$ is independently at each occurrence $(C_1-C_4)$ alkyl, $(C_1-C_4)$haloalkyl, $(C_1-C_4)$alkoxy, $(C_1-C_4)$haloalkoxy, halogen, —$NH_2$, —OH, or CN;

or a pharmaceutically acceptable salt thereof;
wherein the compound of Formula (I), or a pharmaceutically acceptable salt thereof, is administered together, concomitantly or sequentially with an Angiotensin Receptor Blocker selected from candesartan, losartan, irbesartan, telmisartan, olmesartan, eprosartan, fimasartan, and azilsartan, or a pharmaceutically acceptable salt thereof.

11. The method according to claim 10, wherein the compound is of Formula (II):

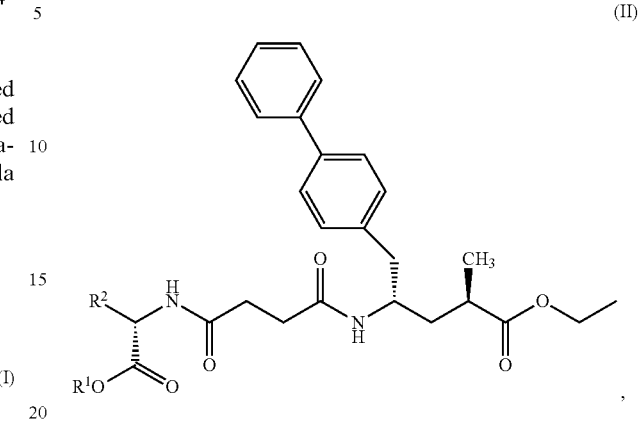

(II)

or a pharmaceutically acceptable salt thereof.

12. The method according to claim 10, wherein $R^1$ is H, ethyl, or t-butyl.

13. The method according to claim 10, wherein $R^2$ is H or $(C_1-C_4)$alkyl optionally substituted with one to two $R^3$.

14. The method according to claim 10, wherein $R^2$ is H or $(C_1-C_4)$alkyl optionally substituted with —$NH_2$.

15. The method according to claim 10, wherein $R^1$ is H, ethyl, or t-butyl, and $R^2$ is H or $(C_4)$alkyl optionally substituted with —$NH_2$.

16. The method according to claim 10, wherein the compound is selected from:
- (4-(((2S,4R)-1-([1,1'-biphenyl]-4-yl)-5-ethoxy-4-methyl-5-oxopentan-2-yl)amino)-4-oxobutanoyl)-L-leucine;
- (4-(((2S,4R)-1-([1,1'-biphenyl]-4-yl)-5-ethoxy-4-methyl-5-oxopentan-2-yl)amino)-4-oxobutanoyl)-L-lysine; and
- tert-butyl (4-(((2S,4R)-1-([1,1'-biphenyl]-4-yl)-5-ethoxy-4-methyl-5-oxopentan-2-yl)amino)-4-oxobutanoyl)-L-lysinate;
- ethyl (2R,4S)-5-([1,1'-biphenyl]-4-yl)-4-(4-(((S)-1-ethoxy-4-methyl-1-oxopentan-2-yl)amino)-4-oxobutanamido)-2-methylpentanoate;
- (4-(((2S,4R)-1-([1,1'-biphenyl]-4-yl)-5-ethoxy-4-methyl-5-oxopentan-2-yl)amino)-4-oxobutanoyl)-L-arginine;
- (4-(((2S,4R)-1-([1,1'-biphenyl]-4-yl)-5-ethoxy-4-methyl-5-oxopentan-2-yl)amino)-4-oxobutanoyl)-L-histidine;
- (4-(((2S,4R)-1-([1,1'-biphenyl]-4-yl)-5-ethoxy-4-methyl-5-oxopentan-2-yl)amino)-4-oxobutanoyl)glycine;
- (4-(((2S,4R)-1-([1,1'-biphenyl]-4-yl)-5-ethoxy-4-methyl-5-oxopentan-2-yl)amino)-4-oxobutanoyl)-L-alanine;
- (4-(((2S,4R)-1-([1,1'-biphenyl]-4-yl)-5-ethoxy-4-methyl-5-oxopentan-2-yl)amino)-4-oxobutanoyl)-L-valine;
- (4-(((2S, 4R)-1-([1,1'-biphenyl]-4-yl)-5-ethoxy-4-methyl-5-oxopentan-2-yl)amino)-4-oxobutanoyl)-L-phenylalanine;
- (4-(((2S,4R)-1-([1,1'-biphenyl]-4-yl)-5-ethoxy-4-methyl-5-oxopentan-2-yl)amino)-4-oxobutanoyl)-L-tryptophan; and
- (4-(((2S,4R)-1-([1,1'-biphenyl]-4-yl)-5-ethoxy-4-methyl-5-oxopentan-2-yl)amino)-4-oxobutanoyl)-L-isoleucine;

or a pharmaceutically acceptable salt thereof.

17. The method according to claim 10, wherein the compound is (4-(((2S,4R)-1-([1,1'-biphenyl]-4-yl)-5- ethoxy-4-methyl-5-oxopentan-2-yl)amino)-4-oxobutanoyl)-L-leucine or a pharmaceutically acceptable salt thereof.

18. The method according to claim 10, wherein the compound is (4-(((2S,4R)-1-([1,1'-biphenyl]-4-yl)-5-ethoxy-4-methyl-5-oxopentan-2-yl)amino)-4-oxobutanoyl)-L-histidine or a pharmaceutically acceptable salt thereof.

19. The method according to claim 10, wherein the disorder or the disease is selected from hypertension, resistant hypertension, pulmonary heart disease, pulmonary hypertension, pulmonary arterial hypertension, isolated systolic hypertension, peripheral vascular disease, heart failure, heart failure with preserved ejection fraction (HF-PEF), heart failure with reduced ejection fraction (HF-REF), mitral stenosis and regurgitation, left ventricular hypertrophy, angina, renal insufficiency, renal failure, diabetic nephropathy, non-diabetic nephropathy, contrast-induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, cardiomyopathy, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, myocardial infarction (MI), renal fibrosis, polycystic kidney disease (PKD), renal failure, cyclical oedema, Menière's disease, hyperaldosteronism, hypercalciuria, ascites, glaucoma, menstrual disorders, preterm labor, pre-eclampsia, endometriosis, and reproductive disorders, asthma, obstructive sleep apnea, inflammation, leukemia, pain, epilepsy, affective disorders, depression, psychotic condition, obesity, gastrointestinal disorders, wound healing, septic shock, gastric acid secretion dysfunction, hyperreninemia, cystic fibrosis, restenosis, type-2 diabetes, metabolic syndrome, diabetic complications, atherosclerosis, and male and female sexual dysfunction.

20. The method according to claim 19, wherein the disorder or the disease is selected from hypertension, pulmonary hypertension, isolated systolic hypertension, resistant hypertension, peripheral vascular disease, heart failure, heart failure with preserved ejection fraction (HF-PEF), heart failure with reduced ejection fraction (HF-REF), and pulmonary arterial hypertension.

21. The method according to claim 16, wherein the disorder or the disease is selected from hypertension, resistant hypertension, pulmonary heart disease, pulmonary hypertension, pulmonary arterial hypertension, isolated systolic hypertension, peripheral vascular disease, heart failure, heart failure with preserved ejection fraction (HF-PEF), heart failure with reduced ejection fraction (HF-REF), mitral stenosis and regurgitation, left ventricular hypertrophy, angina, renal insufficiency, renal failure, diabetic nephropathy, non-diabetic nephropathy, contrast-induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, cardiomyopathy, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, myocardial infarction (MI), renal fibrosis, polycystic kidney disease (PKD), renal failure, cyclical oedema, Menière's disease, hyperaldosteronism, hypercalciuria, ascites, glaucoma, menstrual disorders, preterm labor, pre-eclampsia, endometriosis, and reproductive disorders, asthma, obstructive sleep apnea, inflammation, leukemia, pain, epilepsy, affective disorders, depression, psychotic condition, obesity, gastrointestinal disorders, wound healing, septic shock, gastric acid secretion dysfunction, hyperreninemia, cystic fibrosis, restenosis, type-2 diabetes, metabolic syndrome, diabetic complications, atherosclerosis, and male and female sexual dysfunction.

22. The method according to claim 21, wherein the disorder or the disease is selected from hypertension, pulmonary hypertension, isolated systolic hypertension, resistant hypertension, peripheral vascular disease, heart failure, heart failure with preserved ejection fraction (HF-PEF), heart failure with reduced ejection fraction (HF-REF), and pulmonary arterial hypertension.

23. The method according to claim 17, wherein the disorder or the disease is selected from hypertension, resistant hypertension, pulmonary heart disease, pulmonary hypertension, pulmonary arterial hypertension, isolated systolic hypertension, peripheral vascular disease, heart failure, heart failure with preserved ejection fraction (HF-PEF), heart failure with reduced ejection fraction (HF-REF), mitral stenosis and regurgitation, left ventricular hypertrophy, angina, renal insufficiency, renal failure, diabetic nephropathy, non-diabetic nephropathy, contrast-induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, cardiomyopathy, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, myocardial infarction (MI), renal fibrosis, polycystic kidney disease (PKD), renal failure, cyclical oedema, Menière's disease, hyperaldosteronism, hypercalciuria, ascites, glaucoma, menstrual disorders, preterm labor, pre-eclampsia, endometriosis, and reproductive disorders, asthma, obstructive sleep apnea, inflammation, leukemia, pain, epilepsy, affective disorders, depression, psychotic condition, obesity, gastrointestinal disorders, wound healing, septic shock, gastric acid secretion dysfunction, hyperreninemia, cystic fibrosis, restenosis, type-2 diabetes, metabolic syndrome, diabetic complications, atherosclerosis, and male and female sexual dysfunction.

24. The method according to claim 23, wherein the disorder or the disease is selected from hypertension, pulmonary hypertension, isolated systolic hypertension, resistant hypertension, peripheral vascular disease, heart failure, heart failure with preserved ejection fraction (HF-PEF), heart failure with reduced ejection fraction (HF-REF), and pulmonary arterial hypertension.

25. The method according to claim 18, wherein the disorder or the disease is selected from hypertension, resistant hypertension, pulmonary heart disease, pulmonary hypertension, pulmonary arterial hypertension, isolated systolic hypertension, peripheral vascular disease, heart failure, heart failure with preserved ejection fraction (HF-PEF), heart failure with reduced ejection fraction (HF-REF), mitral stenosis and regurgitation, left ventricular hypertrophy, angina, renal insufficiency, renal failure, diabetic nephropathy, non-diabetic nephropathy, contrast-induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, cardiomyopathy, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, myocardial infarction (MI), renal fibrosis, polycystic kidney disease (PKD), renal failure, cyclical oedema, Menière's disease, hyperaldosteronism, hypercalciuria, ascites, glaucoma, menstrual disorders, preterm labor, pre-eclampsia, endometriosis, and reproductive disorders, asthma, obstructive sleep apnea, inflammation, leukemia, pain, epilepsy, affective disorders, depression, psychotic condition, obesity, gastrointestinal disorders, wound healing, septic shock, gastric acid secretion dysfunction, hyperreninemia, cystic fibrosis, restenosis, type-2 diabetes, metabolic syndrome, diabetic complications, atherosclerosis, and male and female sexual dysfunction.

26. The method according to claim 25, wherein the disorder or the disease is selected from hypertension, pulmonary hypertension, isolated systolic hypertension, resistant hypertension, peripheral vascular disease, heart failure, heart failure with preserved ejection fraction (HF-PEF), heart failure with reduced ejection fraction (HF-REF), and pulmonary arterial hypertension.

\* \* \* \* \*